United States Patent
Rieck et al.

(10) Patent No.: US 10,420,803 B2
(45) Date of Patent: Sep. 24, 2019

(54) DIFFERENTIATION OF PLURIPOTENT STEM CELLS TO INTESTINAL MIDGUT ENDODERM CELLS

(71) Applicant: Janssen Biotech, Inc., Horsham, PA (US)

(72) Inventors: Sebastian Rieck, San Diego, CA (US); Alireza Rezania, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 56 days.

(21) Appl. No.: 15/478,881

(22) Filed: Apr. 4, 2017

(65) Prior Publication Data

US 2017/0296594 A1    Oct. 19, 2017

Related U.S. Application Data

(60) Provisional application No. 62/322,636, filed on Apr. 14, 2016.

(51) Int. Cl.
*A61K 35/38* (2015.01)
*A61K 35/545* (2015.01)
*C12N 5/00* (2006.01)
*C12N 5/071* (2010.01)

(52) U.S. Cl.
CPC ............ *A61K 35/38* (2013.01); *A61K 35/545* (2013.01); *C12N 5/0679* (2013.01); *C12N 2500/38* (2013.01); *C12N 2501/119* (2013.01); *C12N 2501/155* (2013.01); *C12N 2501/19* (2013.01); *C12N 2501/385* (2013.01); *C12N 2501/415* (2013.01); *C12N 2501/727* (2013.01); *C12N 2506/02* (2013.01)

(58) Field of Classification Search
CPC .......... C12N 5/00; C12N 5/04; C12N 5/0606; C12N 5/0018
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshak et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

Abe; et al., Evidence That PI3K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.

Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.

Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

(Continued)

*Primary Examiner* — Ruth A Davis

(74) *Attorney, Agent, or Firm* — Klarquist Sparkman, LLP

(57) ABSTRACT

Cell populations of intestinal midgut endoderm cells and methods of generating the cells expressing markers characteristic of intestinal endoderm lineage are disclosed. Methods of treating conditions such as diabetes are also disclosed.

9 Claims, 45 Drawing Sheets

(56) References Cited

U.S. PATENT DOCUMENTS

| | | |
|---|---|---|
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,460 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomson et al. |
| 7,510,873 B2 | 3/2009 | Mistry et al. |
| 7,510,876 B2 | 3/2009 | D Amour et al. |
| 7,534,608 B2 | 5/2009 | Martinson et al. |
| 7,541,185 B2 * | 6/2009 | D'Amour ............ C12N 5/0018 435/377 |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 9,528,090 B2 | 12/2016 | Rezania |
| 2002/0072117 A1 | 7/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Saiituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0148070 A1 | 7/2005 | Thomson et al. |
| 2005/0158852 A1 | 7/2005 | D'Amour et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003313 A1 | 1/2006 | D'Amour et al. |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania et al. |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2012/0276624 A1 | 11/2012 | D'Amour et al. |
| 2013/0189777 A1 | 7/2013 | Rezania |
| 2013/0224156 A1 | 8/2013 | Takahashi et al. |
| 2014/0186953 A1 | 7/2014 | Rezania |
| 2014/0329321 A1 | 11/2014 | Rajesh et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2005537803 A2 | 12/2005 |
| JP | 2006-500003 A2 | 1/2006 |
| JP | 2008500809 A2 | 1/2008 |

(56) References Cited

FOREIGN PATENT DOCUMENTS

| | | |
|---|---|---|
| JP | 2009513143 A2 | 4/2009 |
| KR | 10-2008-0020098 A | 3/2008 |
| RU | 1767433 A1 | 10/1992 |
| RU | 2342427 C2 | 12/2008 |
| RU | 2359030 C1 | 6/2009 |
| RU | 2359671 C2 | 6/2009 |
| WO | WO199219759 A2 | 2/1992 |
| WO | 1996040172 A1 | 12/1996 |
| WO | 199830679 A1 | 7/1998 |
| WO | 199847892 A1 | 10/1998 |
| WO | WO199920741 A1 | 4/1999 |
| WO | 200029549 A1 | 5/2000 |
| WO | 200123528 A1 | 4/2001 |
| WO | WO200151616 A2 | 7/2001 |
| WO | WO200181549 A3 | 11/2001 |
| WO | 200246183 A2 | 6/2002 |
| WO | 200246197 A1 | 6/2002 |
| WO | 02092756 A2 | 11/2002 |
| WO | WO200305049 A1 | 1/2003 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | 2002086107 A3 | 7/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | WO2003102134 A2 | 12/2003 |
| WO | 2004016747 A2 | 2/2004 |
| WO | WO2004011621 A2 | 2/2004 |
| WO | 2004044158 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006073911 A1 | 7/2006 |
| WO | 2006080952 A2 | 8/2006 |
| WO | 2006083782 A2 | 8/2006 |
| WO | 2006088867 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127927 A2 | 11/2007 |
| WO | 2007136673 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008015418 A2 | 2/2008 |
| WO | 2008015682 A2 | 2/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2008094597 A1 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011096223 A1 | 8/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055397 A1 | 4/2013 |
| WO | 2013055834 A2 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Ackermann, et al., Molecular Regulation of Pancreatic B-Cell Mass Development, Maintenance, and Expansion, Journal of Molecular Endocrinology, 2007, pp. 193-206, vol. 38.
Adams, et al., Proteasome Inhibition in Cancer: Development of PS-341, Seminars in Oncology, 2001, pp. 613-619, vol. 28, No. 6.
Age-Related Eye Disease Study Research Group, A Randomized, Placebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Ali, et al., Exploitation of Protein Kinase C: A Useful Target for Cancer Therapy, Cancer Treatment Reviews, 2009, pp. 1-8, vol. 35.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Ameri, et al., Embryonic Stem Cells/INDUFGF2 Specifies hESC-Derived Definitive Endoderm into Foregut/Midgut Cell Lineages in

(56) References Cited

OTHER PUBLICATIONS a Concentration-Dependent Manner, Stem Cells, 2010, pp. 45-56, vol. 28.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Amit, et al., Feeder Layer-and Serum-Free Culture of Human Embryonic Stem Cells, Biology of Reproduction, 2004, pp. 837-845, vol. 70.
Arai, et al., Purification of Recombinant Activin a Using the Second Follistatin Domain of Follistatin-Related Gene (FLRG), Protein Expression & Purification, 2006, pp. 78-82, vol. 49.
Armstrong, et al., The Role of PI3K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baertschiger, et al., Mesenchymal Stem Cells Derived From Human Exocrine Pancrea Express Transcription Factors Implicated in Beta-Cell Development, Pancreas, 2008, pp. 75-84, vol. 37, No. 1.
Baetge, Production of B-Cells from Human Embryonic Stem Cells, Diabetes, Obesity, Metabolism, 2008, pp. 186-194, vol. 10, Supplement 4.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Balajthy, et al., Molecular therapies., Molecular therapies, 2011, pp. 1-6.
Balsam, et al., Haematopoeitic Stem Cells Adopt Mature Haematopoeitic Fates in Ischemic Myocardiurn, Nature, Apr. 8, 2004, pp. 668-673, vol. 428, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Barclay, et al., The Leucocyte Antigen Facts Book, The Leucocyte Antigen Facts Book, 1997, Textbook, 2[sup] edition, Academic Press.
Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Beltrami, et al., Adult Cardiac Stem Cells are Multipotent and Support Myocardial Regeneration, Cell, Sep. 19, 2003, pp. 763-776, vol. 114, Cell Press.
Best, et al., Embryonic Stem Cells to Beta-Cells by Understanding Pancreas Development, Molecular and Cellular Endocrinology, 2008, pp. 86-94, vol. 288.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bo, et al., Research Progress of Pancreatic Islet Development and Pancreatic Stem Cells, Journal of Clinical Surgery, 2009, pp. 208-210, vol. 17, No. 3.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., In vitro cultivation of human islets from expanded ductal tissue, Proceedings of the National Academy of Sciences, Jul. 5, 2000, pp. 7999-8004, vol. 97-14, National Academy of Sciences.
Borowiak, et al., How to Make AB Cells, Current Opinion Cell Biology, 2009, pp. 727-732, vol. 21, Issue 6.
Borowitz, et al., Prognostic Significance of Fluorescence Intensity of Surface Marker. . . , Blood, Jun. 1, 1997, 3960-3966, vol. 89-11, American Society of Hematology, Washington, D.C., US.
Braam, et al., Improved Genetic Manipulation of Human Embryonic Stem Cells, Nature Methods, May. 2008, pp. 389-392, vol. 5, No. 5.
Brakenhoff et al., Development of a Human Interleukin-6 Receptor Antagonist, Journal of Biological Chemistry, Jan. 7, 1994, pp. 86-93, vol. 269-1, US.
Brambrink, et al., Sequential Expression of Pluripotency Markers During Direct Reprogramming of Mouse Somatic Cells, Cell Stem Cell, 2008, pp. 151-159, vol. 2.
Brevig, et al, The Recognition of Adsorbed and Denatured Proteins of Different Topographies by β2 Integrins and Effects on Leukocyte Adhesion and Activation, Biomaterials, 2005, pp. 3039-3053, vol. 26.
Brevini, et al., No Shortcuts to Pig Embryonic Stem Cells, Theriogenology, 2010, pp. 544-550, vol. 74.
Brimble, S., et al., The Cell Surface Glycosphingolipids SSEA-3 and SSEA-4 Are Not Essential for Human ESC Pluripotency, Stem Cells, Jan. 2007, pp. 54-62, vol. 25.
Bross, et al., Approval Summary for Bortezomib for Injection in the Treatment of Multiple Myeloma, Clinical Cancer Research, Jun. 15, 2004, pp. 3954-3964, vol. 10.
Brown, et al., Optimal Control of Blood Glucose: The Diabetic Patient or the Machine?, Science Translation Medicine, Apr. 14, 2010, pp. 1-5, vol. 2 Issue 27.
Burkard et al, Conditional Neuronal Nitric Oxide Synthase Overexpression Impairs Myocardial Contractility, Circulation Research Jan. 18, 2007, pp. e32-e44, vol. 100.
Buta, et al., Reconsidering pluripotency tests: Do we still need teratoma assays?, Stem Cell Research, Mar. 26, 2013, pp. 552-562, vol. 11.
Buzzard et al., Karyotype of human ES cells during extended culture, Nature Biotechnology, Apr. 1, 2004, 381-382, 22-4, Nature Publishing Group.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Cao, et al., High Glucose is Necessary for Complete Maturation of Pdx1-VP16-Expressing Hepatic Cells into Functional Insulin-Producing Cells, Diabetes, 2004, pp. 3168-3176, vol. 53.
Castaing, et al., Blood Glucose Normalization Upon Transplantation of Human Embryonic Pancreas into Beta-Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecular Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.
Chen, et al., Chemically Defined Conditions for Human iPSC Derivation and Culture, Nature Methods, 2011, pp. 424-429, vol. 8, Issue 5.

(56) References Cited

OTHER PUBLICATIONS

Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chen, et al., Differentiation of Rat Marrow Mesenchymal Stem Cells in Pancreatic Islet Beta-Cells, World Journal of Gastroenterology, Oct. 15, 2004, 3016-3020, 10.
Chen, et al., Retinoic acid signaling is essential for pancreas development and promotes endocrine at the expense of exocrine cell differentiation in Xenopus, Developmental Biology, May 4, 2004, pp. 144-160, vol. 271.
Chen, et al., Scalable GMP Compliant Suspension Culture System for Human ES Cells, Stem Cell Research, 2012, pp. 388-402, vol. 8.
Cheon et al., Secretory Leukocyte Protease Inhibitor (SLPI) Regulate the Embryonic Differentiation During periimplantation Stage, Biology of Reproduction, 2007, 64, 77, Society for the Study of Reproduction, Inc.
Cheon, et al., Defined Feeder-Free Culture System of Human Embryonic Stem Cells, Biol Reprod, 2005, 105.046870, DOI10/1095.
Chetty, et al., A Simple Tool ti improve Pluripotent Stem Cell Differentiation, Nature Methods, 2013, pp. 553-558, vol. 10, No. 6.
Choi, et al., Effect of ascorbic acid on bone marrow-derived mesenchymal stem cell proliferation and differentiation, J Biosci Bioeng, Jun. 2008, pp. 586-594, vol. 105 Issue 6.
Choi, et al., In Vitro Trans-Differentiation of Rat Mesenchymal Cells into Insulin-Producing Cells by Rat Pancreatic Extract, Biochemical and Biophysical Research Communications, 2005, pp. 1299-1305, vol. 330.
Chung, et al., Human Embryonic Stem Cell Lines Generated without Embryo Destruction, Cell Stem Cell, 2008, pp. 113-117, vol. 2.
Cirulli, et al., Netrins: beyond the brain, Molecular Cell Biology, Apr. 2007, pp. 296-306, vol. 8.
Cohick, et al., The Insulin-Like Growth Factors, Annual Reviews Physiol, 1993, pp. 131-153, vol. 55, Annual Reviews Inc.
Condic, et al., Alternative Sources of Pluripotent Stem Cells: Ethical and Scientific Issues Revisited, Stem Cells and Development, 2010, pp. 1121-1129, vol. 19 issue 8, Mary Ann Liebert, Inc.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al., Efficient differentiation of human embryonic stem cells to definitive endoderm, Nature Biotechnology, Oct. 28, 2005, pp. 1534-1540, vol. 23.
D'Amour et al., Production of pancreatic hormone-expressing endocrine cells from human embryonic stem cells, Nature Biotechnology, Oct. 19, 2006, pp. 1392-1401, vol. 24 Issue 11, Nature Publishing Group, US.
Daheron, et al., LIF/STAT3 Signaling Fails to Maintain Self-Renewal of Human Embryonic Stem Cells, Stem Cells, 2004, pp. 770-778, vol. 22.
Damy, et al., Increased Neuronal Nitric Oxide Synthase-Derived NO Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Coppi, et al., Isolation of Amniotic Stem Cell Lines with Potential for Therapy, Nature Biotechnology, 2007, pp. 100-106, vol. 25, No. 1.
De Rosa, 11-color, 13-parameter flow cytometry: Identification of . . . , Nature, Feb. 1, 2001, 245-248, 7-2, Nature Publishing Group, US.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, John Wiley & Sons, Chichester, 1995, pp. 1-3, page number, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331 XP002699177, vol. 11, No. 9/10.
Dupont-Gillain, et al., Plasma-Oxidized Polystyrene: Wetting Properties and Surface Reconstruction, Langmuir, 2000, pp. 8194-8200, vol. 16.
Eguizabal, et al., Embryonic Stem Cells/Induced Pluripotent Stem Complete Meiosis from Human Induced Pluripotent Stem Cells, Stem Cells, 2011, pp. 1186-1195, vol. 29.
Ellerstrom, et al., Derivation of a Xeno-free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodeling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripotent Neural Stem Cells Engrafted into the Adult Rat Subretinal Space, Ophthamology & Visual Science, Dec. 2003, pp. 5417-5422, vol. 44 No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Findikli, et al., Establishment and characterization of new human embryonic stem cell lines, Reproductive BioMedicine Online, Mar. 3, 2005, pp. 617-627, vol. 10 Issue 5.

(56) References Cited

OTHER PUBLICATIONS

Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.

Florio, et al., Activin A Stimulates Insulin Secretion in Cultured Human Pancreatic Islets, J. Endocrinol. Invest., 2000, pp. 231-234, vol. 23.

Fok, et al., Shear-Controlled Single-Step Mouse Embryonic Stem Cell Expansion and Embryoid Body-Based Differentiation, Stem Cells, 2005, pp. 1333-1342, vol. 23.

Foster, et al., Differentiation of Transplanted Microencapsulated Fetal Pancreatic Cells, Experimental Transplantation, Jun. 15, 2007, pp. 1440-1448, vol. 83, No. 11.

Frandsen et al., Activin B mediated induction of Pdx1 in human embryonic stem cell derived embryoid bodies, Biochemical and Biophysical Research Communications, Aug. 15, 2007, 568-574, 362, Elsevier Inc.

Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.

Fung, et al., The Effect of Medical Therapy and Islet Cell Transplantation on Diabetic Nephropathy: An Interim Report, Transplantation, Jul. 15, 2007, pp. 17-22, vol. 84, No. 1.

Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.

Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, pp. 16806-16811, 103-45, National Academy of Sciences, US.

Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.

Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.

Gershengorn et al., Epithelial-to-Mesenchymal Transition Generates Proliferative Human Islet Precursor Cells, Science, Dec. 24, 2004, 2261-2264, 306, US.

Gibco, Insulin-Transferin-Selenium-X 100X, Invitrogen Cell Culture, Apr. 2005, pp. 1, Form No. 3032.

Gibco, Solutions for Life Science Research and Drug Discovery, Catalogue Cell Culture Products, 2004-2005, pp. 1-4E, 281406 26 5 27.

Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.

Ginis, et al., Differences Between Human and Mouse Embryonic Stem Cells, Developmental Biology, 2004, pp. 360-380, vol. 269.

Gittes, Developmental Biology of the Pancreas: A comprehensive Review, Developmental Biology, 2009, pp. 4-35, vol. 326, No. 1.

Gomez, et al., Derivation of cat embryonic stem-like cells from in vitro-produced blastocysts on homologous and heterologous feeder cells, Theriogenology, May 11, 2010, pp. 498-515, vol. 74.

Gordon Weir, Do stem cells hold the key to creation of a cure for diabetes?, Diabetes Voice, 2008, pp. 29-31, Edition 53, No. 2.

Gosden, et al., Amniotic Fluid Cell Types and Culture, British Medical Bulletin, 1983, pp. 348-354, vol. 39, No. 4.

Graham, et al., Characteristics of a Human Cell Line Transformed by DNA from Human Adenovirus Type 5, Journal General Virology, 1977, pp. 59-72, vol. 36.

Gregg Duester, Retinoic Acid Synthesis and Signaling During Early Organogenesis, Cell, 2008, pp. 921-931, vol. 134.

Guillemain, et al., Glucose Is Necessary for Embryonic Pancreatic Endocrine Cell Differentiation*, The Journal of Biological Chemistry, May 18 2007, pp. 15228-15237, vol. 282 Issue 20.

Guo, et al., Efficient differentiation of insulin-producing cells from skin-derived stem cells, Cell Proliferation, 2009, pp. 49-62, vol. 42.

Guo, et al., Stem Cells to Pancreatic B-Cells: New Sources for Diabetes Cell Therapy, Endocrine Reviews, May 2009, pp. 214-227, vol. 30, No. 3, The Endocrine Society.

Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.

Hainsworth, et al., Retinal Capillar Basement Membrane Thickening in a Porcine Model of Diabetes Mellitus, Comp Med, 2002, pp. 523-529, vol. 52.

Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.

Harb, et al., The Rho-Rock-Myosin Signaling Axis Determines Cell-Cell Integrity of Self-Renewing Pluripotent Stem Cells, Plos One, 2008, Article e3001, vol. 3, Issue 8.

Harmon, et al., GDF11 Modulates NGN3+ Islet Progenitor Cell Number and Promotes B-Cell Differentiation in Pancreas Development, Development, 2004, pp. 6163-6174, vol. 131.

Haruta, et al., In Vitro and In Vivo Characterization of Pigment Epthelieal Cells Differentiated from Primate Embryonic Stem Cells, Investigative Ophthalmology & Visual Science, Mar. 2004, pp. 1020-1025, vol. 45 Issue 3, Association for Research in Vision and Ophthalmology.

Hasegawa, et al., A Method for the Selection of Human Embryonic Stem Cell Sublines with High Replating Efficiency After Single-Cell Dissociation, Stem Cells, 2006, pp. 2649-2660, vol. 24.

Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.

Hay, et al., Highly Efficient Differentiation of hESCs to Functional Hepatic Endoderm Requires Activin A and Wnt3a Signaling, PNAS, 2008, pp. 12301-12306, vol. 105, No. 34.

Hebrok, et al., Notochord repression of endodermal Sonic hedgehog permits pancreas development, Genes & Development, Apr. 2, 1998, pp. 1705-1713, vol. 12, Issue 11, Cold Spring Harbor Laboratory Press.

Heinis, et al., HIF1a and Pancreatic Beta-Cell Development, The FASEB Journal, 2012, pp. 2734-2742, vol. 26.

Heinis, et al., Oxygen Tension Regulates Pancreatic Beta-Cell Differentiation Through Hypoxia-Inducible Factor 1x, Diabetes, 2010, pp. 662-669, vol. 59.

Heit, et al., Embryonic Stem Cells and Islet Replacement in Diabetes Mellitus, Pediatric Diabetes, 2004, pp. 5-15, vol. 5.

Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

Helena Edlund, Pancreatic Organogenisis—Pancreatic Mechanisms and Implications for Therapy; Nature, Jul. 1, 2002, pp. 524-532, vol. 3, Nature Publishing Group, US.

Henderson, et al., Preimplantation Human Embryos and Embryonic Stem Cells Show Comparable Expression of Stage-Specific Embryonic Antigens, Stem Cells, 2002, pp. 329-337, vol. 20.

Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.

Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.

Herrera, Adult-Insulin-and Glucagon-Producing Cells Differentiate from Two Independent Cell Lineages, Development, 2000, pp. 2317-2322, vol. 127, No. 11.

(56) References Cited

OTHER PUBLICATIONS

Herzenberg, et al., Fluorescence-activated Cell Sorting, Scientific American, 1976, pp. 108-117, vol. 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Hiemisch, H., et al., Transcriptional Regulation in Endoderm Development: Characterization of an Enhancer Controlling Hnf3g Expression by Transgenesis and Targeted Mutagenesis, The EMBO Journal, 1997, 3995-4006, vol. 16(13).
Ho, et al., Animal Cell Bioreactors, Animal Cell Bioreactors, 1991, pp. 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hori, et al., Growth inhibitors promote differentiation of insulin-producing tissue from embryonic stem cells, Proceedings of the National Academy of Sciences, Dec. 10, 2002, pp. 16105-16110, vol. 99-25, National Academy of Sciences.
Hosoya, et al., Induction of Differentiation of Undifferentiated Cells into Pancreatic Beta-Cells in Vertebrates, Int. J. Dev. Biol., 2012, pp. 313-323, vol. 56.
Hou, et al., A regulatory network controls nephrocan expression and midgut patterning, Development, Aug. 8, 2014, pp. 3772-3781, vol. 141.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of induced Pluripotent Stem Cells to Thymic Epithelial Cells by Phenotype, Immunology and Cell Biology, Jun. 24, 2010, pp. 1-8, doi:10.1038/icb.2010.96.
Inman, et al., SB-431542 is a Potent and Specific Inhibitor of Transforming Growth Factor-B Superfamily Type I Activin Receptor-Like Kinase (ALK) Receptors ALK4, ALK5, and ALK7, Molecular Pharmacology, 2002, pp. 65-74, vol. 62, No. 1.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, pp. 544-549, vol. 23, AlphaMed Press.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jaenisch, et al., Stem Cells, the Molecular Circuitry of Pluripotency and Nuclear Reprogramming, cell, Feb. 22, 2008, pp. 567-582, vol. 132, Elsevier Inc.
Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.
Jean, et al., Pluripotent genes in avian stem cells, Development Growth & Differentiation, 2013, pp. 41-51, vol. 55.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Jiang, et al., In Vitro Derivation of Functional Insulin-Producing Cells from Human Embryonic Stem Cells, Cell Research, 2007, pp. 333-344, vol. 17.
Johansson, et al., Temporal Control of Neurogenin 3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Kang, et al., Plasma treatment of textiles—Synthetic Polymer-Based Textiles, AATCC Review, 2004, pp. 29-33, Page number.
Karvonen, et al., Incidence of Childhood Type 1 Diabetes Worldwide, Diabetes Care, 2000, pp. 1516-1526, vol. 23, No. 10.
Kehoe, et al., Scalable Stirred-Suspension Bioreactor Culture of Human Pluripotent Stem Cells, Tissue Eng Part A, 2010, pp. 405-421, vol. 16 Issue 2.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, The Journal of Neuroscience, Aug. 27, 2003, pp. 7742-7749, vol. 23, Issue 21.
Kim, et al., Reprogrammed Pluripotent Stem Cells from Somatic Cells, International Journal of Stem Cells, 2011, pp. 1-8, vol. 4 Issue 1.
King, et al., Bioreactor development for stem cell expansion and controlled differentiation, Current Opinion in Chemical Biology, Jul. 25, 2007, pp. 394-398, vol. 11, Elsevier Ltd.
Kingsley, The TGF-B Superfamily: New Members, New Receptors, and New Genetic Tests of Function in Different Organisms, Genes & Development, 1994, pp. 133-146, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Klajnert, et al., Fluorescence studies on PAMAM dendrimers interactions with bovine serum albumin, Bioelectrochernistry, 2002, pp. 33-35, vol. 55.
Kleinman et al., Basement Membrane Complexes with Biological Activity, Biochemistry, 1986, pp. 312-318, vol. 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Konstantinova, et al., EphA-Ephrin-A-Mediated Beta Cell Communication Regulates Insulin Secretion from Pancreatic Islets, Cell, Apr. 20, 2007, pp. 359-370, vol. 129.
Koyangi, et al., Inhibition of the Rho/ROCK Pathway Reduces Apoptosis During Transplantation of Embryonic Stem Cell-Derived Neural Precursors, Journal of Neurosciene Research, Sep. 7, 2007, 270-280, 86, Wiley-Liss, Inc.
Kozikowski, et al., New Amide-Bearing Benzolactam-Based Protein Kinase C Modulators Induce Enhanced Secretion of the Amyloid Precursor Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9, 10-diones, Journal of Medical Chemistry, 1985, 1124-1126, 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

(56) References Cited

OTHER PUBLICATIONS

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.

Ku et al., Committing Embryonic Stem Cells to Early Endocrine Pancreas In Vitro, Stem Cells, 2004, 1205-1217, 22, AlphaMed Press.

Kubo et al., Development of definitive endoderm from embryonic stem cells in culture, Development, 2004, 1651-1662, 131, The Company of Biologists.

Kubota, et al., Growth factors essential for self-renewal and expansion of mouse spermatogonial stem cells, cell Biology, Nov. 23, 2004, pp. 16489-16494, vol. 101, Issue 47.

Kumar, et al., Recent Developments in β-Cell Differentiation of Pluripotent Stem Cells Induced by Small and Large Molecules, International Journal of Molecular Sciences, Dec. 17, 2014, pp. 23418-23447, vol. 15.

Kunisada, et al., Small molecules induce efficient differentiation into insulin-producing cells from human induced pluripotent stem cells, Stem Cell Research, Oct. 11, 2011, pp. 274-284, vol. 8.

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Lanza, et al., Characteristics and Characterization of Human Pluripotent Stem Cells, Stem Cell Anthology, 2010, pp. 141, 142, 144 and 146; 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity arid Metabolism, 2007, pp. 170-179, vol. 9, Supplement 2, Blackwell Publishing Ltd.

Larsen, et al., Use of the Gottingen Minipig as a Model of Diabetes, with Special Focus on Type 1 Diabetes Research, ILAR Journal, 2004, pp. 303-313, vol. 45, No. 3.

Lavial, et al., Chicken Embryonic Stem Cells as a Non-Mammalian Embryonic Stem Cell Model, Development Growth Differentiation, Jan. 2010, pp. 101-114, vol. 52(1).

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Available human feeder cells for the maintenance of human embryonic stem cells, Reproduction, 2004, pp. 727-735, vol. 128.

Lee, et al., Human B-cell Precursors Mature into Functional Insulin-Producing Cells in an Immunoisolation Device: Implications for Diabetes Cell Therapies, Transplantation, Apr. 15, 2009, pp. 983-991, vol. 87, No. 7.

Lee, et al., PKC-Inhibitors Sustain Self-Renewal of Mouse Embryonic Stem Cells Under Hypoxia in Vitro; Experimental and Molecular Medicine, Apr. 2010, pp. 294-301, vol. 42, No. 4.

Lee, et al., Protein Kinase A- and C- Induced Insulin Release from Ca2+-Insensitive Pools, Cellular Signalling, 2003, pp. 529-537, vol. 15.

Lee, et al., Retinoic Acid-Induced Human Secretin Gene Expression in Neuronal Cells is Mediated by Cyclin-Dependent Kinase 1, Annals of the New York Academy of Sciences, 2006, pp. 393-398, vol. 1070.

Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.

Leon-Quinto, et al., In Vitro Directed Differentiation of Mouse Embryonic Stem Cells into Insulin-Producing Cells, Diabetologia, 2004, pp. 1442-1451 XP002699175, vol. 47, No. 8.

Levenstein et al., Basic Fibroblast Growth Factor Support of Human Embryonic Stem Cell Self-Renewal, Stem Cells, Nov. 10, 2005, 568-574, 24, AlphaMed Press.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Li, et al., Pluripotency Can be Rapidly and Efficiently Induced in Human Amniotic Fluid-Derived Cells, Human Molecular Genetics, 2009, pp. 4340-4349, vol. 18, No. 22.

Lilja et al., Cyclin-dependent Kinase 5 Promotes Insulin Exocytosis, Journal of Biological Chemistry, Jul. 6, 2001, 34199-34205, 36-7, JBC Papers in Press.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Lin, C., et al., Coagulation Dysregulatin as a Barrier to Xenotransplantation n the Primate, Transplant Immunology, 2009, pp. 75-80, vol. 21.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Pluripotency, Annu Rev Genomics Hum Genet, 2011, pp. 165-185, vol. 12.

Ludwig, et al., Defined, Feeder-Independent Medium for human Embryonic Stem Cell Culture, Current Protocols in Stem Cell Biology, 2007, pp. 1C.2.1-1C.2.16, vol. 1, John Wiley & Sons. Inc.

Ludwig, et al., Defined Culture Media for Human Embryonic Stem Cells, Embryonic Stem Cells, 2007, pp. 1-16, Springer.

Ludwig, et al., Derivation of Human Embryonic Stem Cells in Defined Conditions, Nature Biotechnology, Feb. 2006, pp. 185-187, vol. 24 No. 2.

Lumelsky, et al., Differentiation of Embryonic Stem Cells to Insulin-Secreting Structures Similar to Pancreatic Islets, Science, 2001, 1389-1394, 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, J. Lsukoc. Biol, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Maimets, et al., Activation of p53 by nutlin leads to rapid differentiation of human embryonic stem cells, Oncogene, Jun. 2, 2008, pp. 5277-5287, vol. 27.

Mao, et al., The Reversal of Hyperglycemia in Diabetic Mice Using PLGA Scaffolds Seeded with Islet-like Cells Derived from Human Embryonic Stem Cells, Biomaterials, 2009, pp. 1706-1714, vol. 30.

Maria-Jesus Obregon, Thyroid hormone and adipocyte differentiation, Thyroid, 2008, pp. 185-195, vol. 18 Issue 2.

(56) References Cited

OTHER PUBLICATIONS

Marshall, et al., Early Micro-and Macro-Angiopathy in the Streptozotocin, Research in Experimental Medicine, 1980, pp. 145-158, vol. 177, Springer-Verlag.
Marshall, et al., Isolation and Maintenance of Primate Embryonic Stem Cells, Methods in Molecular Biology, 2001, pp. 11-18, vol. 158.
Martin, et al., Bioreactors for Tissue Mass Culture: Design, Characterization, and Recent Advances, Biomaterials, Jul. 14, 2005, pp. 7481-7503, vol. 26.
Marzo, et al., Pancreatic islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic. . . , Diabetologia, 2004, pp. 686-694, vol. 47.
Mathis, et al., B-Cell Death During Progression to Diabetes, Nature, 2001, pp. 792-798, vol. 414.
Matveyenko, et al., Inconsistent Formation and Nonfunction of Insulin-Positive Cells from Pancreatic Endoderm Derived from Human Embryonic Stem Cells in Athymic Nude Rats, American Journal of Physiol Endocrinol Metab, 2010, pp. E713-E720, vol. 299.
McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.
McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.
McLin, et al., Repression of WNT/(szligbeta)-6atenin Signaling in the Anterior Endoderm is Essential for Liver and Pancreas Development, Development, 2007, pp. 2207-2217, vol. 134, Issue 12.
McMahon, et al., Noggin-mediated antagonism of BMP signaling is required for growth and patterning of the neural tube and somite, Genes & Development, Mar. 16, 1998, pp. 1438-1452, vol. 12.
Meijer, et al., Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, 301-305, 54, American Diabetes Association.
Micallef, et al., Pancreas Differentiation of Mouse ES Cells, Current Protocols in Stem Cell Biology, 2007, pp. 1G.1.1-1.2.8, John Wiley & Sons, Inc.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Misiti, et al., 3,5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204.
Mitalipova, et al., Preserving the Genetic Integrity of Human Embryonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moore, et al., The Corneal Epithelial Stem Cell, DNA and Cell Biology, 2002, pp. 443-451, vol. 21, No. 5/6.
Moran, et al., Bidirectional-Barbed Sutured Knotless Running Anastomosis v Classic van Velthoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, An Oral Inhibitor of the 20s Proteasorne, Blood, Nov. 16, 2008, p. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780; vol. 117, No. 6.
Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, pp. S75-S80, vol. 22, Supplement 1.
Nakanishi, et al., Pancreatic tissue formation from murine embryonic stem cells in vitro, Differentiation, 2007, pp. 1-11, vol. 75.
Nakase, et al., Myeliod Antigen, CD13, CD14, and/ or CD33 Expression Is Restricted to Certain Lymphoid Neoplasms, Hematopathology, Jun. 1996, pp. 761-768, vol. 105 Issue 6.
Narang, A., et al., Biological and Biomaterial Approaches for Improved Islet Transplantation, Pharmacological Review, Jun. 2006, pp. 194-243, vol. 58(2).
Nekrasov, et al., Induced pluripotent stem cells as a model for studying human diseases, Cellular Transplantology and Tissue Engineering, 2011, pp. 32-37, vol. 6 Issue 2 (English Abstract).
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nie, et al., Scalable Passaging of Adherent Human Pluripotent Stem Cells, PLOS One, 2014, pp. 1-9, vol. 9, Issue 1.
Nishimura, et al., Expression of MafA in Pancreatic Progenitors is Detrimental for Pancreatic Development, Developmental Biology, 2009, pp. 108-120, vol. 333.
Nostro, et al., Generation of Beta Cells from Human Pluripotent Stem Cells: Potential for Regenerative Medicine, Seminars in Cell & Developmental Biology, 2012, pp. 701-710, vol. 23.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Olmer, et al., Long Term Expansion of Undifferentiated Human iPS and ES Cells in Suspension Culture Using Defined Medium, Stem Cell Research, 2010, pp. 51-64, vol. 5.

(56) References Cited

OTHER PUBLICATIONS

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

Osafune, et al., Marked differences in differentiation propensity among human embryonic stem cell lines, Nature Biotechnology, Feb. 17, 2008, pp. 313-315, vol. 26 Issue 3.

Osborne, et al., Some Current Ideas on the Pathogenesis and the Role of Neuroprotection in Glaucomatous Optic Neuropathy, European Journal of Ophthalmology, 2003, pp. S19-S26, vol. 13, Supplement 3, Wichtig Editore.

Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.

Ouziel-Yahalom, et al., Expansion and redifferentiation of adult human pancreatic islet cells, Biochemical and Biophysical Research Communications, Jan. 19, 2006, pp. 291-298, vol. 341.

Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.

Panchision, et al., Optimized Flow Cytometric Analysis of Central Nervous System Tissue Reveals Novel Functional Relationships Among Cells Expressing CD133, CD15, and CD24, Stem Cells, 2007; pp. 1560-1570, vol. 25.

Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.

Pangas, et al., Production and Purification of Recombinant Human Inhibin and Activin, Journal of Endocrinology, 2002, pp. 199-210, vol. 172.

Pardo, et al., Corning CellBIND Surface: An Improved Surface for Enhanced Cell Attachment, Corning Technical Report, 2005, 8 page report.

Paris, et al, Embryonic Stem Cells in Domestic Animals, Embryonic Stem Cells in Domestic Animals, Feb. 7, 2014, 516-524, 74.

Paris, et al., Equine Embryos and Embryonic Stem Cells: Defining Reliable Markers of Pluripotency, Theriogenology, 2010, pp. 516-524, vol. 74.

Park, et al., Effects of Activin A on Pancreatic Ductal Cells in Streptozotocin-Induced Diabetic Rats, Experimental Transplantation, 2007, pp. 925-930, vol. 83.

Peerani, et al., Niche-Mediated Control of Human Embryonic Stem Cell Self-Renewal and Differentiation, The EMBO Journal, 2007, pp. 4744-4755, vol. 26.

Perrier, et al., Derivation of Midbrain Dopamine Neurons from Human Embryonic Stem Cells, PNAS, Aug. 24, 2004, pp. 12543-12548, vol. 101, No. 34.

Petitte, J., et al., Avian Pluripotent Stem Cells, Mechanisms of Development, 2004, pp. 1159-1168, vol. 121.

Phillips, et al., Attachment and Growth of Human Embryonic Stem Cells on Microcarriers, Journal of Biotechnology, 2008, pp. 24-32, vol. 138.

Phillips, et al., Directed Differentiation of Human Embryonic Stem Cells into the Pancreatic Endocrine Lineage, Stem Cells and Development, 2007, pp. 561-578, vol. 16, No. 4.

Pouton, et al., Embryonic Stem Cells as a Source of Models for Drug Discovery, Nature Reviews Drug Discovery, Aug. 2007, pp. 1474-1776, vol. 6, No. 8.

Prichard, et al., Adult Adipose Derived Stem Cell Attachment to Biomaterials, Biomaterials, 2006, pp. 936-946, vol. 28, No. 6.

Prowse, et al., A Proteome Analysis of Conditioned Media from Human Neonatal Fibroblasts Used in the Maintenance of Human Embryonic Stem Cells, Proteomics, 2005, pp. 978-989, vol. 5.

Prusa, et al., Oct-4-Expressing Cells in Human Amniotic Fluid: a New Source for Stem Cell Research?, Human Reproduction, 2003, pp. 1489-1493, vol. 18, No. 7.

Ptasznik, et al., Phosphatidylinositol 3-Kinase is a Negative Regulator of Cellular Differentiation, The Journal of Cell Biology, 1997, pp. 1127-1136, vol. 137, No. 5.

R&D Systems, Embryonic & Induced Pluripotent Stem Cell Transcription Factors, Embryonic & Induced Pluripotent Stem Cell Transcription Factors, 2013, http://www.rndsystems.com/molecule_group.aspx?r=1&g-3041, 2 page web printout.

R&D Systems, Pancreatic Endoderm, Pancreatic Endoderm, Jun. 24, 2013, http://www.rndsystems.com/molecule_group.aspx?g=801&r, 1 page web printout.

Rajagopal, et al., Insulin Staining of ES Cell Progeny from Insulin Uptake, Science, Jan. 17, 2003, pp. 363, vol. 299.

Rajala, et al., Testing of Nine Different Xeno-free Culture Media for Human Embryonic Stem Cell Cultures, Human Reproduction, Jan. 24, 2007, pp. 1231-1238, vol. 22, No. 5.

Ramiya, et al., Reversal of insulin-dependent diabetes using islets generated in vitro from pancreatic stem cells, Nature Medicine, Mar. 2000, pp. 278-282, vol. 6 Issue 3.

Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.

Ratanasavanh, et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytochemistry, 1986, pp. 527-533, vol. 34, Issue 4.

Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.

Rebollar, et al., Proliferation of Aligned Mammalian Cells on Laser-Nanostructured Polystyrene, Biomaterials, 2008, pp. 1796-1806, vol. 29.

Reisner, Growing Organs for Transplantation form Embryonic Precursor Tissues, Immunol. Res., 2007, pp. 261-273, vol. 38.

Reubinoff et al., Embryonic stem cell lines from human blastocysts: somatic differentiation in vitro, Nature Biotech, Apr. 18, 2000, 399-404, 18, Nature America Inc.

Rezania, E al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

Rezania, et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.

Rezania, et al., Reversal of Diabetes with Insulin-Producing Cells Derived in vitro from Human Pluripotent Stem Cells, Nature Biotechnology, 2014, pp. 1121-1133, vol. 32, No. 11.

Rezania, Production of Functional Glucagon-Secreting-Cells from Human Embryonic Stem Cells, Diabetes, 2011, pp. 239-247, vol. 60, Issue 1.

Richards et al., Comparative Evaluation of Various Human Feeders for Prolonged Undifferentiated Growth of Human Embryonic Stem Cells, Stem Cells, 2003, 546-556, 21, AlphaMed Publishing.

Richards, et al., Development of Defined Media for the Serum-Free Expansion of Primary Keratinocytes and Human Embryonic Stem Cells, Tissue Engineering, 2008, pp. 221-232, vol. 14, No. 3.

Richardson, et al., Bortezomid (PS-341): A Novel, First-in-Class Proteasome Inhibitor for the Treatment of Multiple Myeloma and Other Cancers, Cancer Control, 2003, pp. 361-369, vol. 10, No. 5.

Ricordi et al., Automated Method for Isolation of Human Pancreatic Islets, Diabetes, Apr. 1988, 413-420, 37, American Diabetes Association.

Ross, et al., Cytochrome P450s in the Regulation of Cellular Retinoic Acid Metabolism, Annu. Rev. Nutr., 2011, pp. 65-87, vol. 31.

Rother, et al., Challenges facing islet transplantation for the treatment of type 1 diabetes mellitus, The Journal of Clinical Investigation, 2004, pp. 877-883, vol. 114 Issue 7.

Rowely, et al., Meeting Lot-size Challenges of Manufacturing Adherent Cells for Therapy, Bio Process International, Mar. 2012, pp. 16-22, vol. 10 Issue 3.

(56) References Cited

OTHER PUBLICATIONS

Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adult mesenchymal Stem Cells in the CNS, Society for Neuroscience Abstract Viewer and Itinerary Planner, 2002, XP002519394, Program 237.18.
Sander, et al., Horneobox Gene Nkk6.1 Lies Downstream of Nkx2.2 in the Major Pathway of Betta-Cell Formation in the Pancreats, Development, 2000, pp. 5533-5540, vol. 127.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182 , Issue 2.
Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.
Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Schulz, et al., A Scalable System for Production of Functional Pancreatic Progenitors from Human Embryonic Stem Cells, PLOS One, 2012, pp. 1-17, vol. 7, Issue 5.
Scullica, et al., Diagnosis and Classification of Macular Degenerations: an Approach Based on Retinal Function Testing, Documenta Ophthalmologica, 2001, pp. 237-250, vol. 102.
Seaberg et al., Clonal identification of multipotent precursors from adult ~ mouse pancreas that generate neural and pancreatic lineages, Nature Biotechnology, Sep. 2004, pp. 1115-1124, vol. 22, No. 9, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88,vol. 439.
Shamblott et al., Derivation of pluripotent stem cells from cultured human primordial germ cells, Developmental Biology, Nov. 1998, pp. 13726-13731, vol. 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Shim, et al., Directed Differentiation of Human Embryonic Stem Cells Towards a Pancreatic Cell Fate, Diabetologia, 2007, pp. 1228-1238, vol. 50.
Schindler et al., A synthetic nanofibrillar matrix promotes in vivo-like organization and morphogenesis for cells in culture, Biomaterials, Apr. 18, 2005, 5624-5631, 26, Elsevier.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, 61-69, 15, Mary Ann Liebert, Inc.
Sigma-Aldrich, Product Description of MCDB-131, Sigma-Aldrich, 2007, pp. 1-2.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Sjogren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monoclonal Antibody Induces Regression of Human Prostate Cancer Xenografts in Nude Mice, The Prostate, Mar. 2, 2001, 47-53, 48, Wiley-Liss, Inc.
Sneddon, et al., Self-Renewal of Embryonic-Stem-Cell-Derived Progenitors by Organ-Matched Mesenchyme, Nature, Nov. 29, 2012, pp. 765-770, vol. 491.
Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.
Soria, et al., From Stem Cells to Beta Cells: New Strategies in Cell Therapy of Diabetes Mellitus, Diabetologia, 2001, pp. 407-415, vol. 44.
Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stacpoole, et al., Efficient Derivation of Neural Precursor Cells, Spinal Motor Neurons and Midbr, Nat Protoc, 2012, pp. 1-26, vol. 6, Issue 8.
Stadtfeld, et al., Defining Molecular Cornerstones During Fibroblast to iPS Cell Reprogramming in Mouse, Cell Stem Cell, Mar. 2008, pp. 230-240, vol. 2.

(56) References Cited

OTHER PUBLICATIONS

Stafford, et al., Retinoic Acid Signaling is Required for a Critical Early Step in Zebrafish Pancreatic Development, Current Biology, 2002, pp. 1215-1220, vol. 12, Issue 14.
Stafford, et al., Retinoids Signal Directly to Zebrafish Endoderm to Specify Insuilin-Expressing B-cells, Development, 2005, pp. 949-956, vol. 133 Issue 5.
Stoffel, et al., Navigating the Pathway from Embryonic Stem Cells to Beta Cells, Seminars in Cell & Developmental Biology, 2004, pp. 327-336, vol. 15.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells; Research Papers of the Suzuken Memorial Foundation, 2007, pp. 193-197, vol. 24.
Swindle, et al., Swine in Biomedical Research: Management and Models, ILAR News, 1994, pp. 1-5, vol. 36, No. 1.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associated Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the Internet.
Thomson et al., Embryonic Stem Cell Lines Derived from Human Blastocysts, Science, Nov. 6, 1998, pp. 1145-1147, vol. 282, HighWire Press.
Thomson et al., Isolation of a primate embryonic stem cell line, Developmental Biology, Aug. 1995, pp. 7844-7848, vol. 92, Proc. Natl. Acad. Sci, US.
Thomson et al., Primate Embryonic Stem Cells, Currenl Topics in Developmental Biology, 1998, pp. 133-154, vol. 38, Academic Press, US.
Thomson, Bioprocessing of Embryonic Stem Cells for Drug Discovery, Trends in Biotechnology, 2007, pp. 224-230, vol. 25, No. 5.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 877-886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tsuchida, et al., Activin Isoforms Signal Through Type I Receptor Serine/Threonin Kinase ALK7, Molecular and Cellular Endocrinology, 2004, pp. 59-65, vol. 22.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediatric Surgery, Jan. 1988, 3-9, 23-1.
Valet, et al., Pretherapeutic Identification of High-Risk Acute Myeliod Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Choice of Anatomical Site for Islet Transplantation, Cell Transplantation, 2008, pp. 1005-1014, vol. 17.
Van Kooten, et al., Plasma-Treated Polystyrene Surfaces: Mode Surfaces for Studying Celi-Biomaterial Interactions, Biomaterials, 2004, pp. 1735-1747, vol. 25.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.
Verkhovskaya, et al., Effect of alkoxy-substituted of glycerin on the morphofunctional properties of continuous cell culture, Cryobiology, 1990, pp. 30-33, vol. 1 (English Abstract).
Vieira, et al., Modulation of Neuronal Stem Cell Differentiation by Hypoxia and Reactive Oxygen Species, Progress in Neurobiology, 2011, pp. 444-455, vol. 93.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.

(56) References Cited

OTHER PUBLICATIONS

Wachs, et al., High Efficacy of Clonal Growth and Expansion of Adult Neural Stem Cells, Laboratory Investigation, 2003, pp. 949-962, vol. 83, No. 7.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structures of Anthraquinones with their Effects on the Suppression of Immune Responses, International Journal of Immunopharmacology, 1987, 733-739, 9-6, International Society for Immunopharmacology, GB.
Wang, et al., Cultivation and identification of pancreatic endocrine progenitor cells, National Medical Journal of China, 2006, pp. 1850-1853, vol. 86 Issue 26 (English Abstract).
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Wang, et al., Scalable expansion of human induced pluripotent stem cells in the defined xeno-free E8 medium under adherent and suspension culture conditions, Stem Cell Research, Nov. 2013, pp. 1103-1116, vol. 11 Issue 3.
Wang, et al., Three-Dimensional Differentiation of Embryonic Stem Cells into Islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., C-Myc is Dispensable for Direct Reprogramming of Mouse Fibroblasts, Cell Stem Cell, Jan. 2008, pp. 10-12, vol. 2.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wiles et al., Embryonic Stem Cell Development in a Chemically Defined Medium, Experimental Cell Research, 1999, 241-248, 247, Academic Press.
Wong, et al., Directed Differentiation of Human Pluripotent Stem Cells into Mature Airway Epithelial Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, pp. 972-980, vol. 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Xudong, et al., Research Progress in Inducing Stem Cells to Differentiate toward the B-like Cells of Pancreatic Islet, Chinese Bulletin of Life Sciences, 2007, pp. 526-530, vol. 19, No. 5 (English Abstract).
Yadlin, et al., Small-molecule inducers of insulin expression in pancreatic α-cells, PNAS, Aug. 24, 2010, pp. 15099-15104, vol. 107 Issue 34.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Evaluation of Human MSCs Cell Cycle, Viability and Differentiation in Micromass Culture, Biorheology, 2006, p. 489-496, vol. 43.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yim, et al., Proliferation and differentiation of human embryonic germ cell derivatives in bioactive polymeric fibrous scaffold, J.Biomater. Sci.Polymer Edn,, Jan. 19, 2005, pp. 1193-1217, vol. 16 Issue 10.
Yoneda, et al., The Rho Kinases I and II Regulate Different Aspects of Myosin II Activity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zalzman, et al., Differentiation of Human Liver-Derived, Insulin-Producing Cells Toward the B-Cell Phenotype, Diabetes, 2005, pp. 2568-2575, vol. 54.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese PLA Academy of Military Medical Sciences, 2003, 1-127, 1-127 (English Abstract).
Zhang, et al., Highly Efficient Differentiation of Human ES Cells and iPS Cells into Mature Pancreatic Insulin-Producing Cells, Cell Research, 2009, pp. 429-438, vol. 19, Issue 4.
Zhao et al., The Islet B Cell-enriched MafA Activator is a Key Regulator of Insulin Gene Transcription, Journal of Biological Chemistry, Mar. 25, 2005, 11887-11894, 280-12, The American Society for Biochemistry and molecular Biology, Inc.
Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.
Zhu, et al., A Small Molecule Primes Embryonic Stern Cells for Differentiation, Cell Stem Cell, May 8, 2009, pp. 416-426, vol. 4.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.

(56) References Cited

OTHER PUBLICATIONS

Zulewski, et al., Multipotentital Nestin-Positive Stem Cells Isolated From Adult Pancreatic Islets Differentiate Ex Vivo Into Pancreatic Endocrine, Exocrine, and Hepatic Phenotypes, Diabetes, 2001, pp. 521-533, vol. 50.
Zuscik, et al., Regulation of Chondrogenesis and Chondrocyte Differentiation by Stress, J Clin Invest, 2008, pp. 429-438, vol. 118, Issue 2.
Kaufmann, et al., Alternative functional in vitro models of human intestinal epithelia, Front. Pharmacol., 2013, vol. 4, Article 79.
Spence, et al., Directed differentiation of human pluripotent stem cells into intestinal tissue in vitro, Nature, 2011, pp. 105-109, vol. 470(7332).
Watson, et al., An in vivo model of human small intestine using pluripotent stem cells, Nature Medicine, 2014, pp. 1310-1316, vol. 20.

* cited by examiner

FIG. 1A

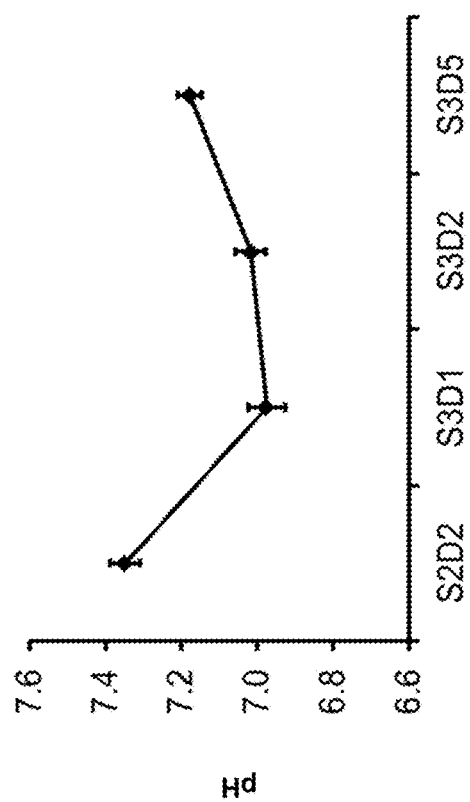

| H1-hESC [cells/cm$^2$] | 337969 ± 156017 |
| --- | --- |
| S3D5 [cells/cm$^2$] | 905208 ± 184586 |
| hESC::S3D5 | 4.56 ± 2.60 |

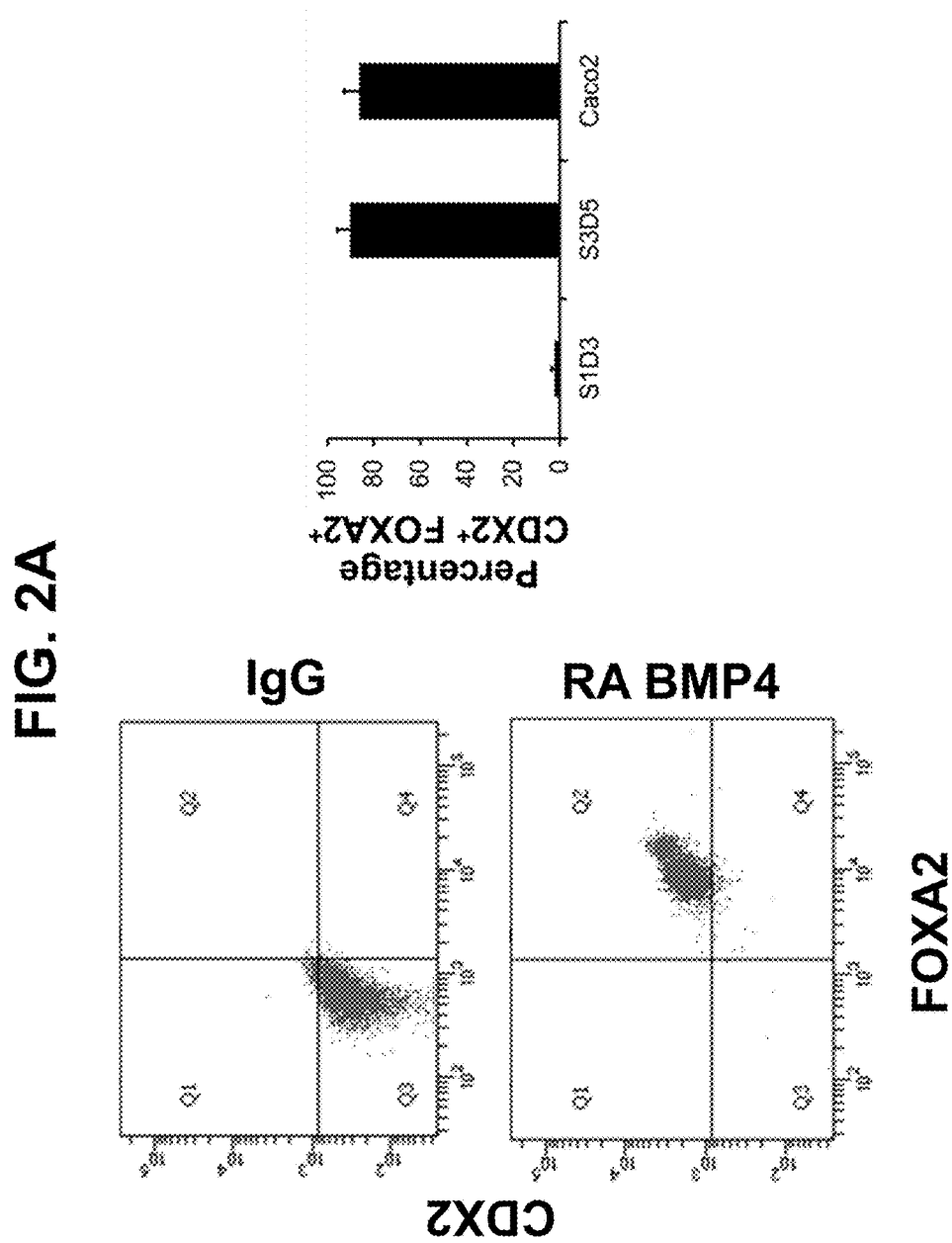

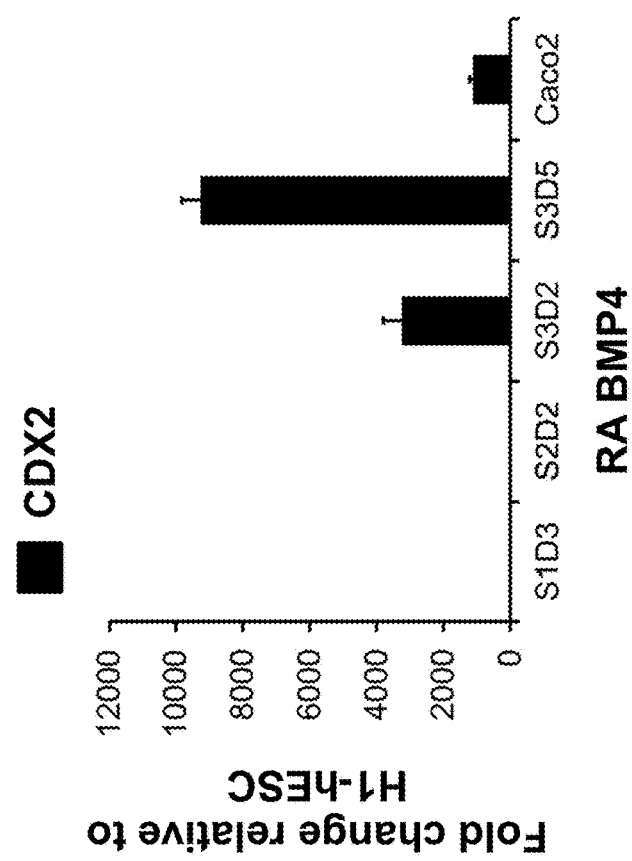

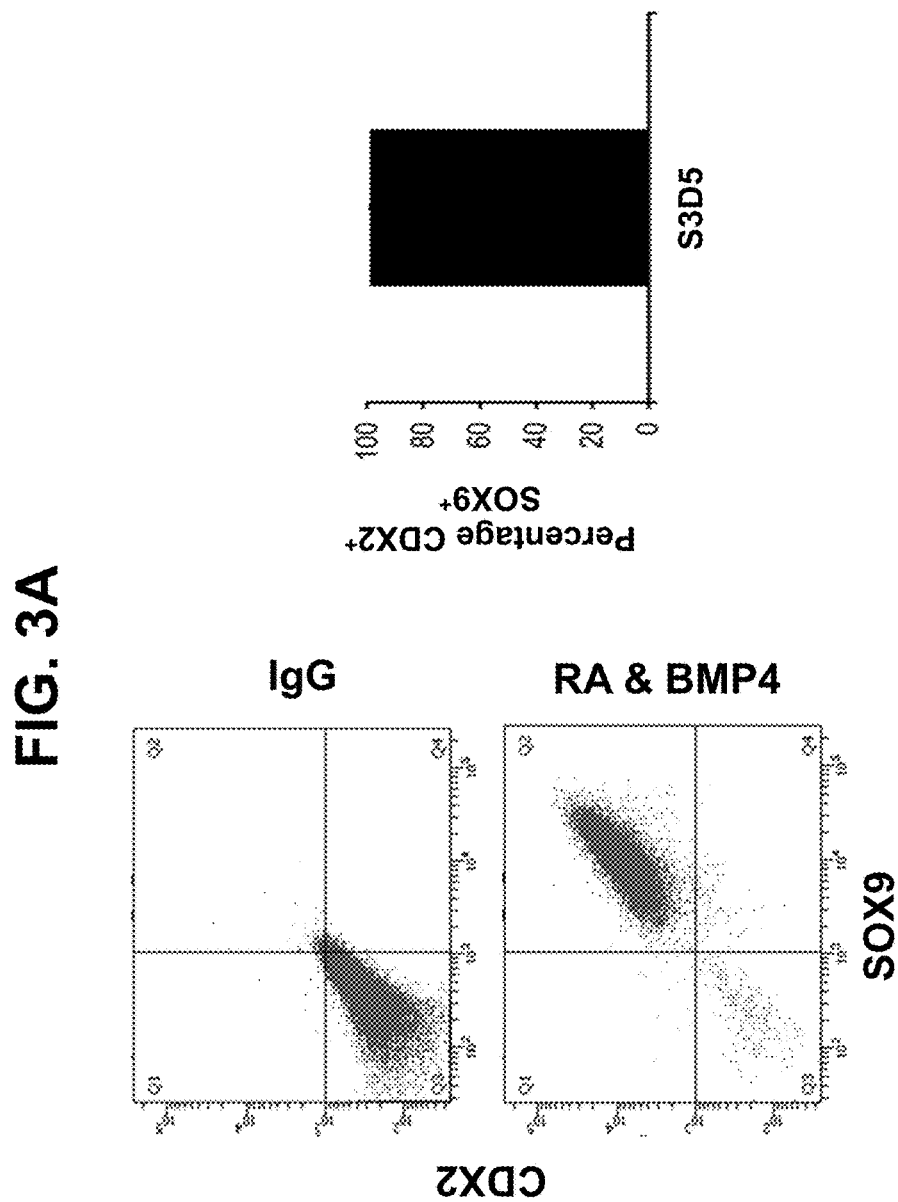

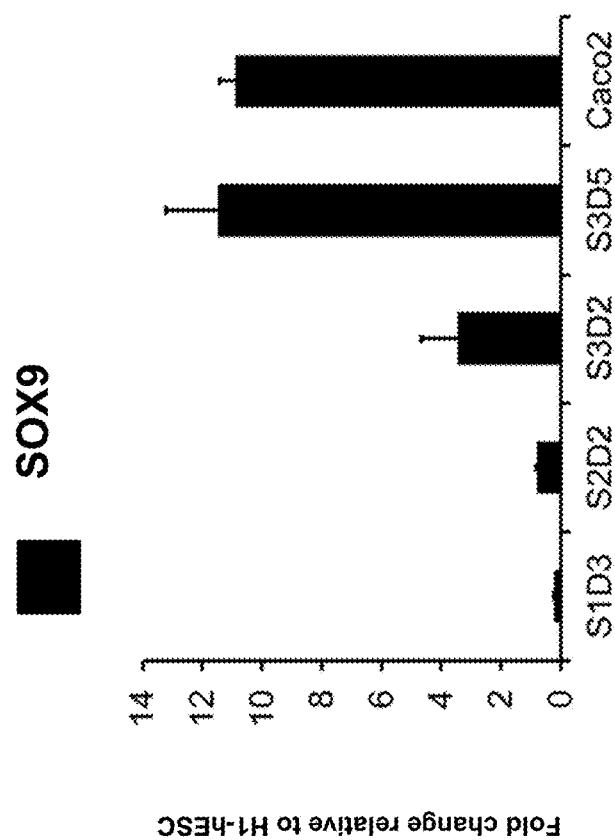

FIG. 3C
RA BMP4
S3D5
SOX6
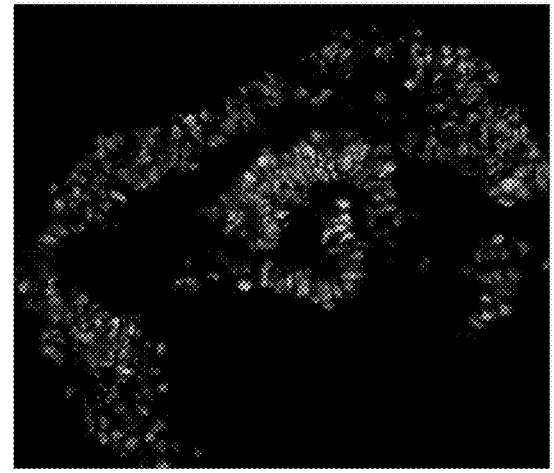
SOX9   CDX2

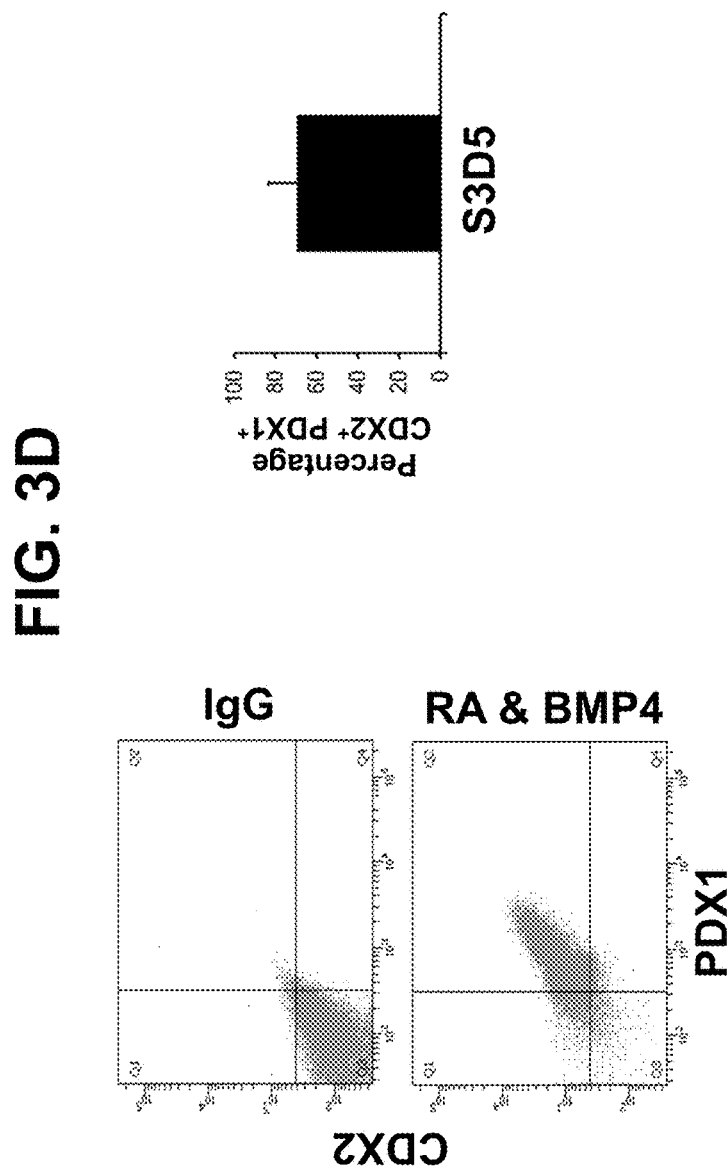

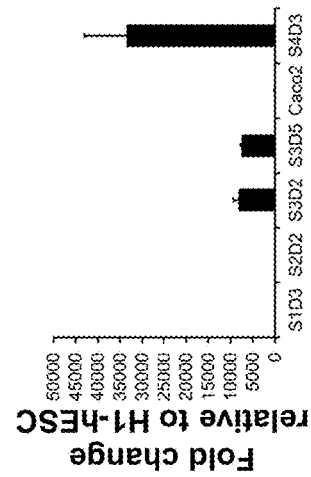
FIG. 3E
FIG. 3F

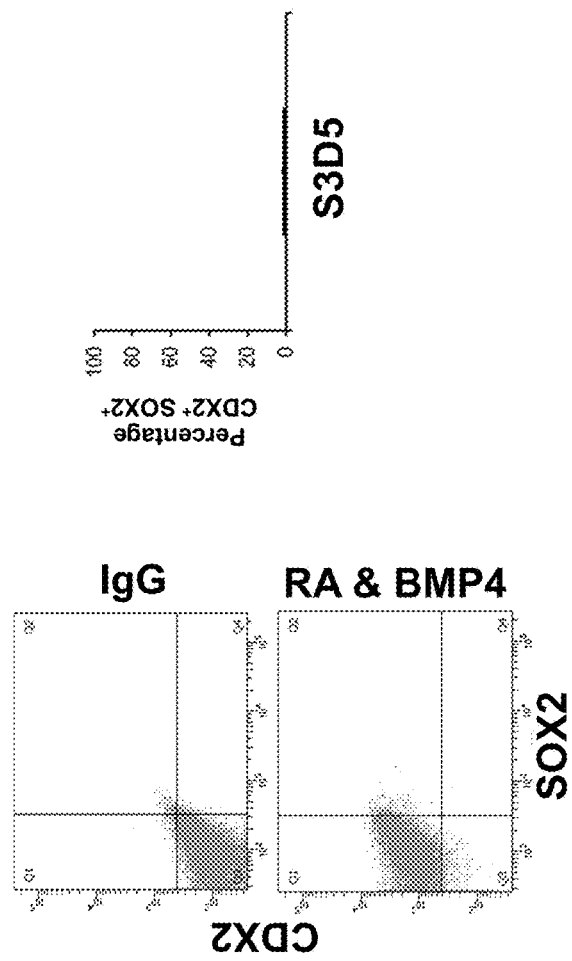

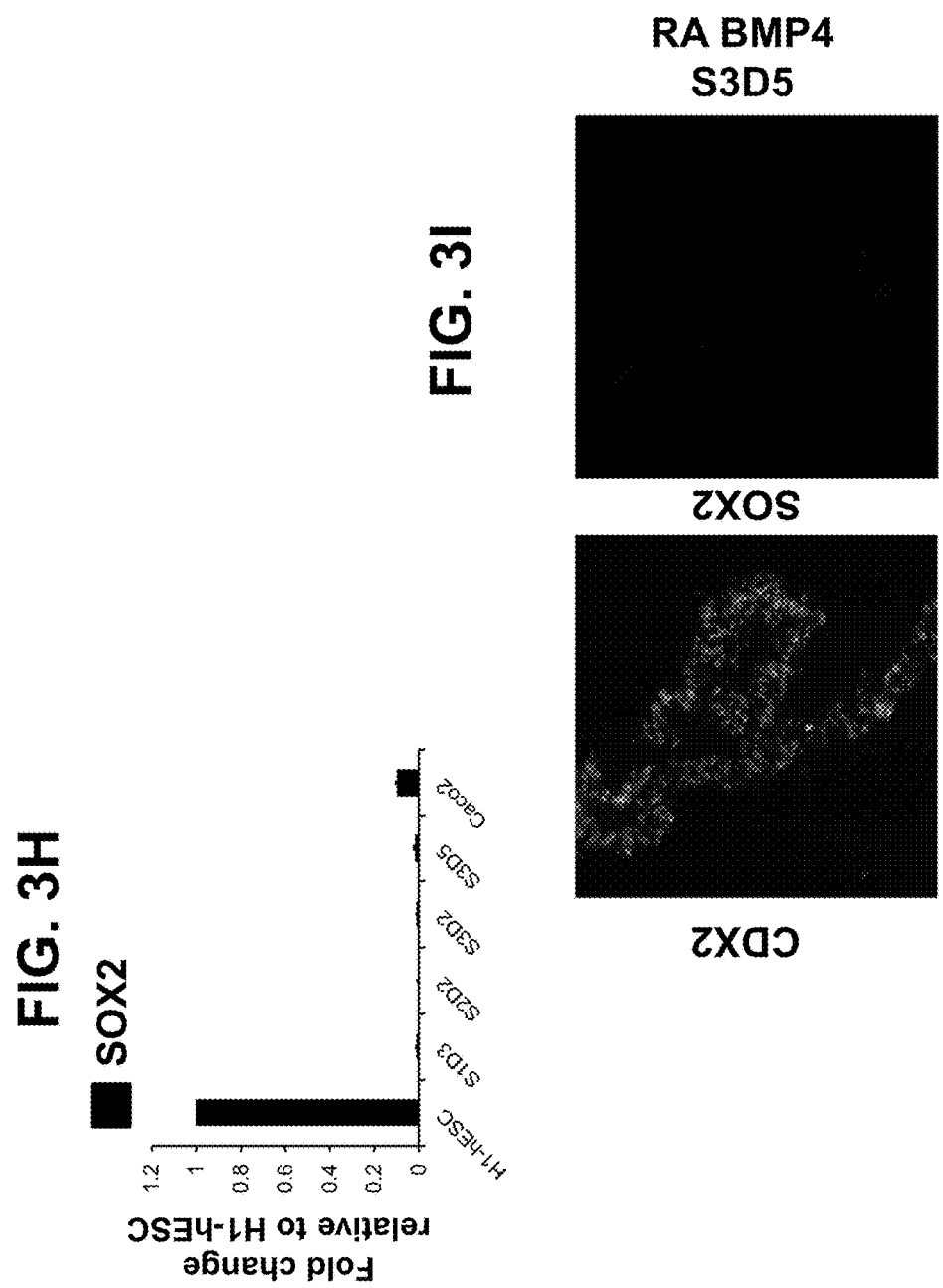

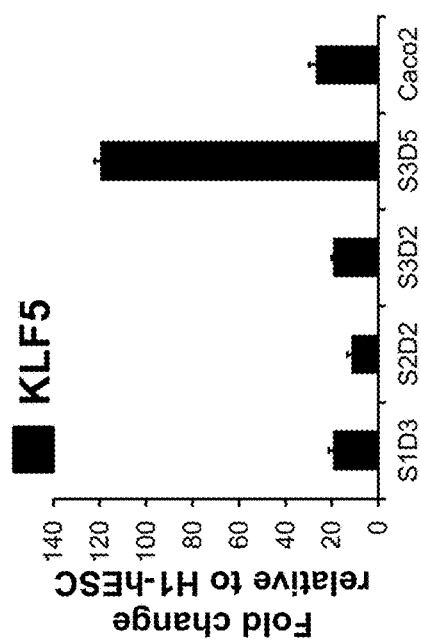
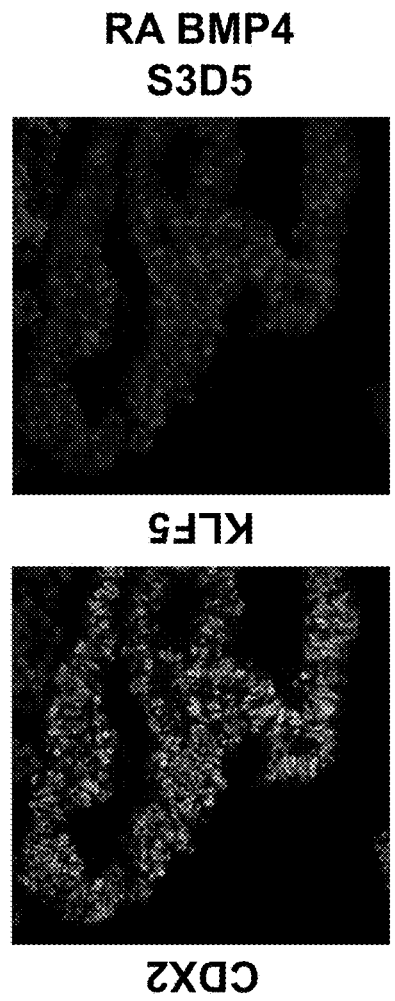

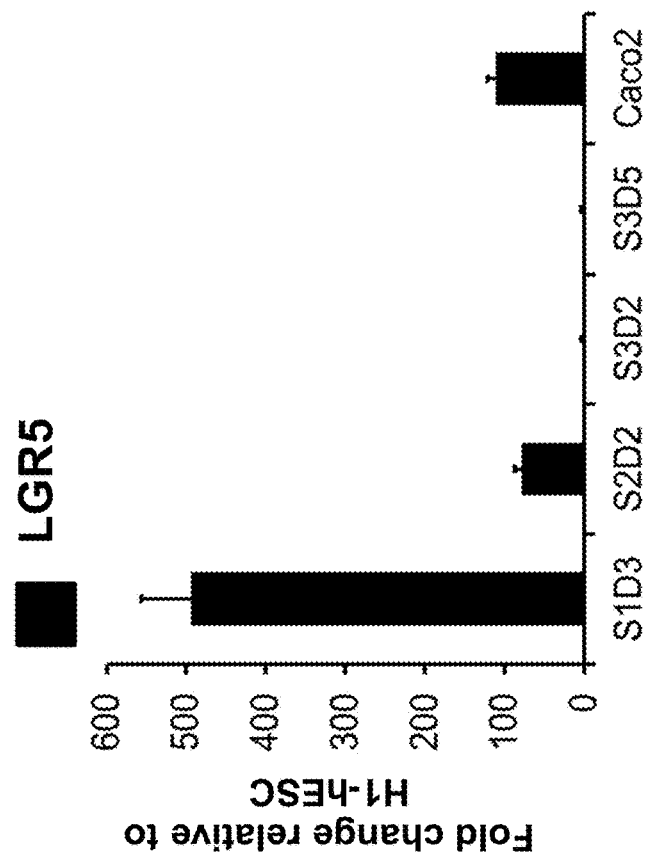

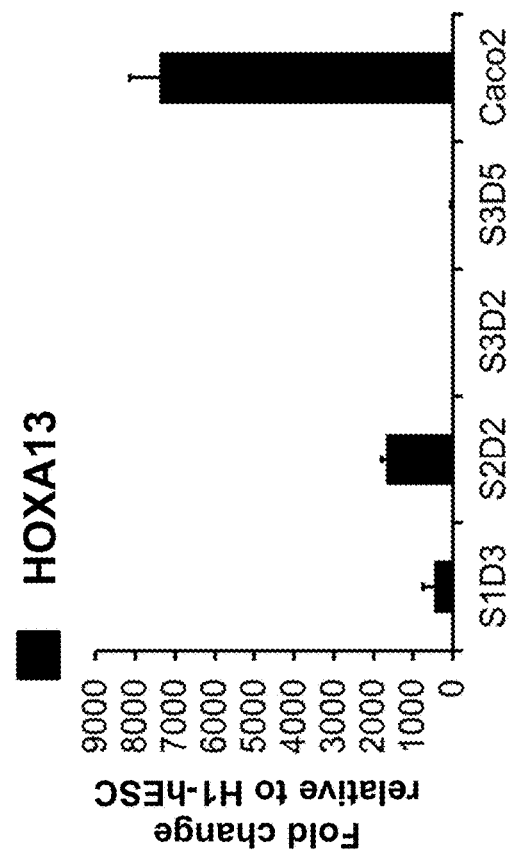

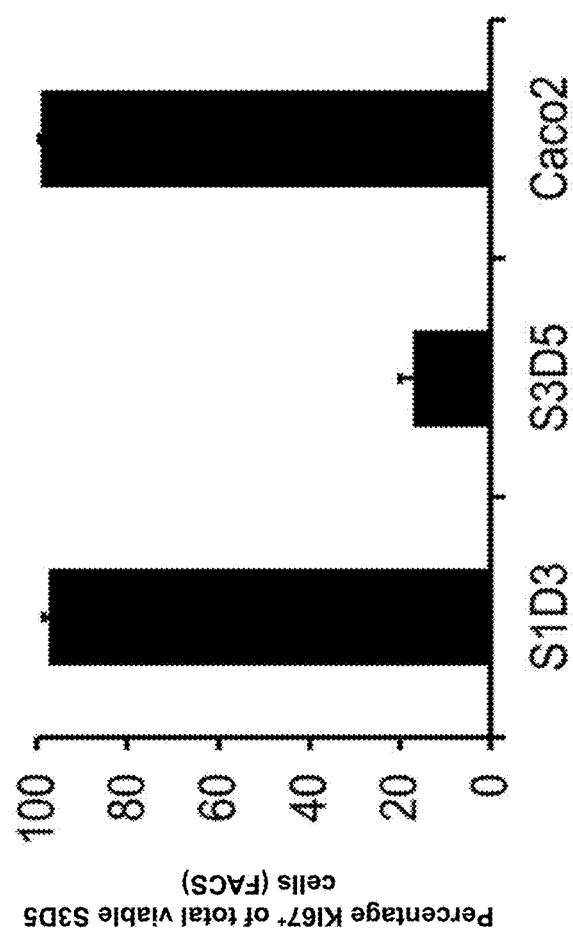

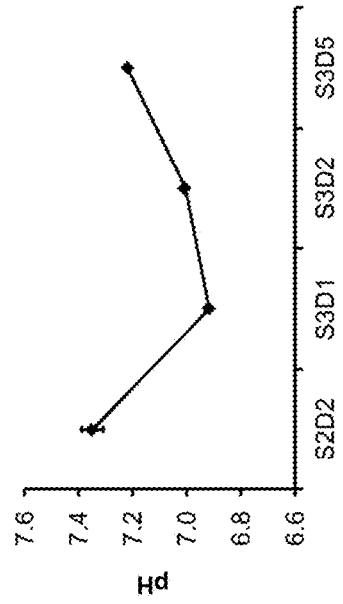

S3D5 hES cell monolayer
RA BMP2

Caco2 cells

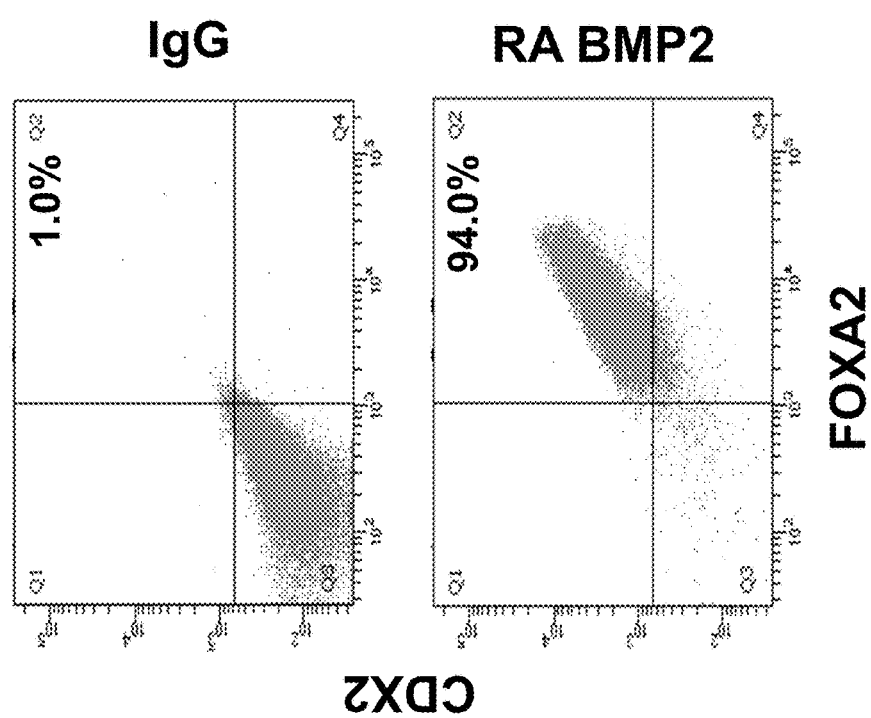

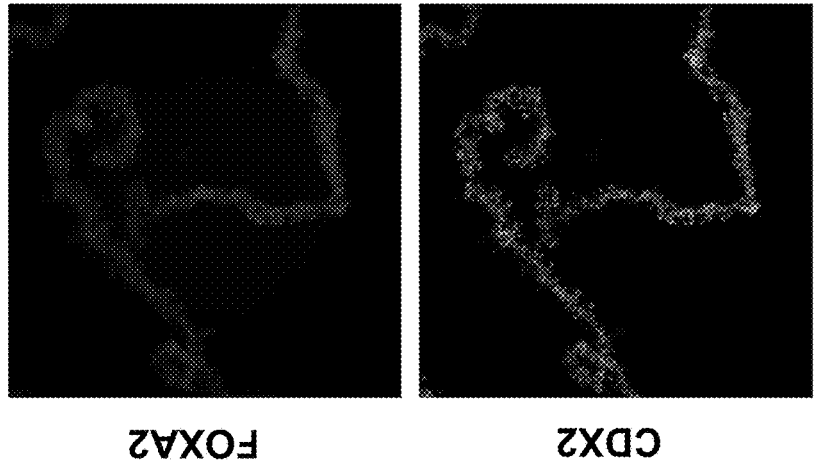

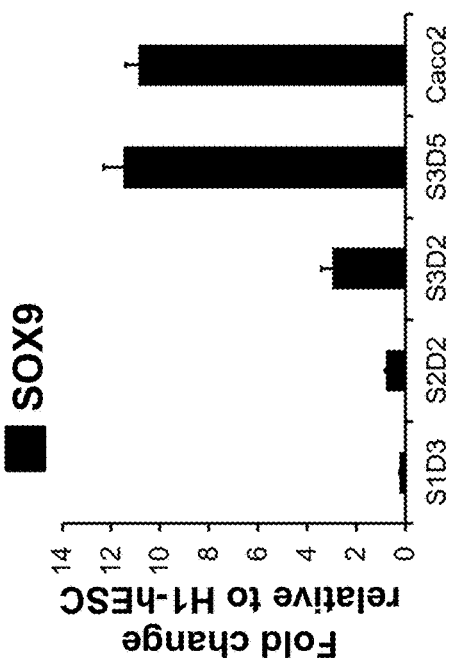
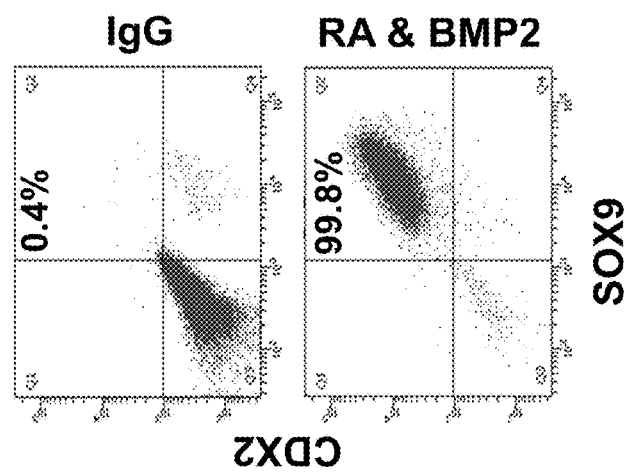
FIG. 6F
FIG. 6E

FIG. 6G
RA BMP2
S3D5
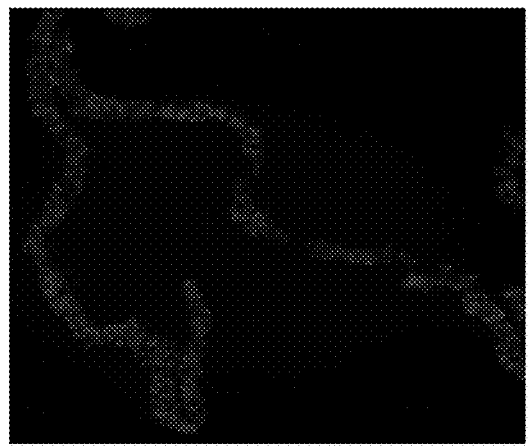
SOX6
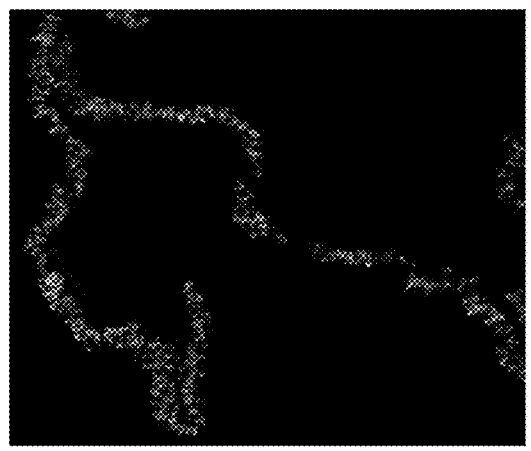
CDX2

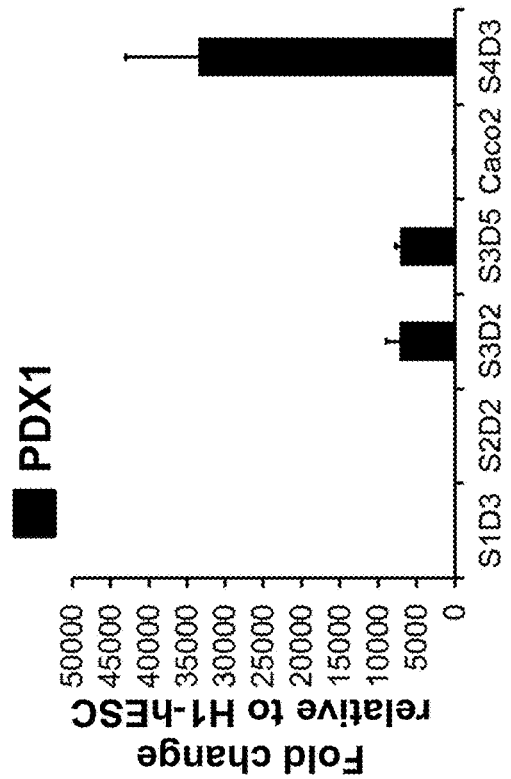
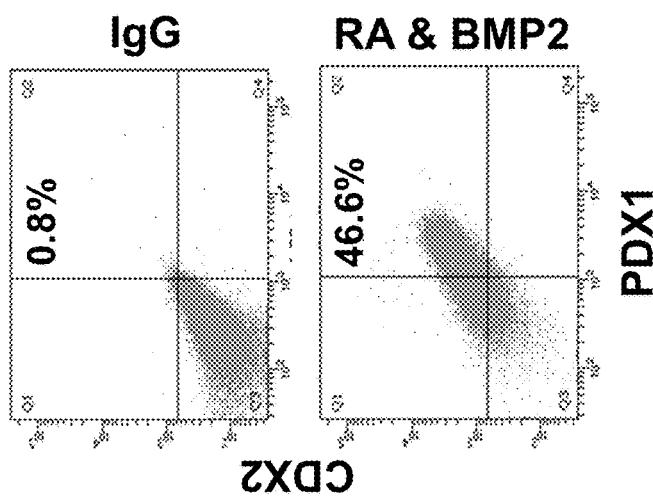

FIG. 6J
RA BMP2
S3D5
PDX1
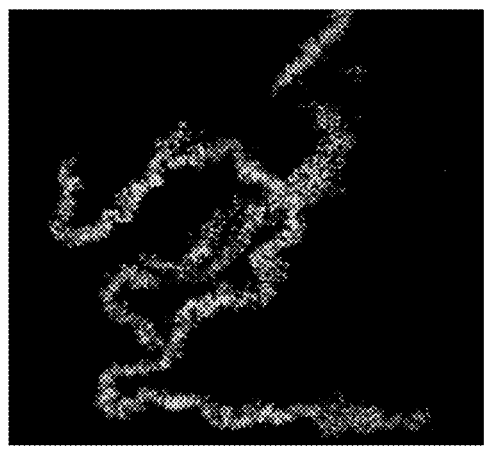
CDX2

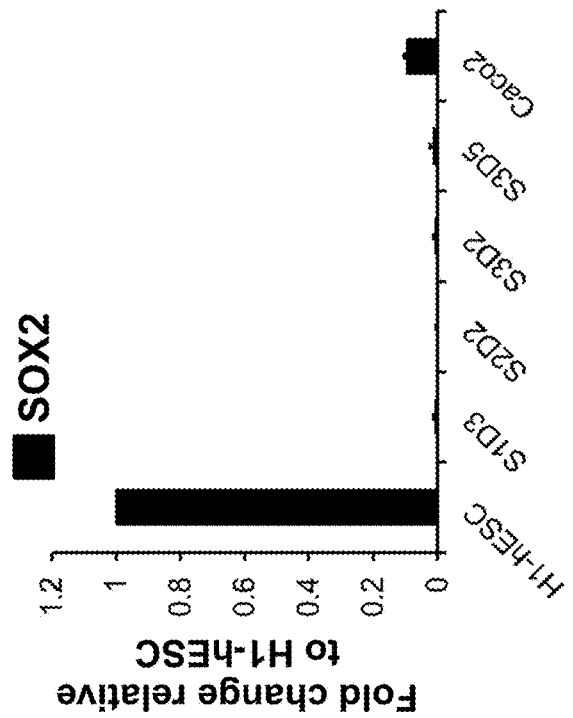
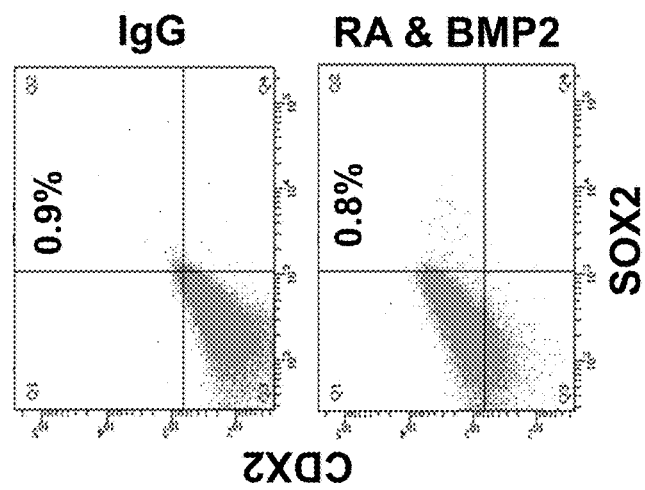

FIG. 6M
RA BMP2
S3D5
SOX2
CDX2
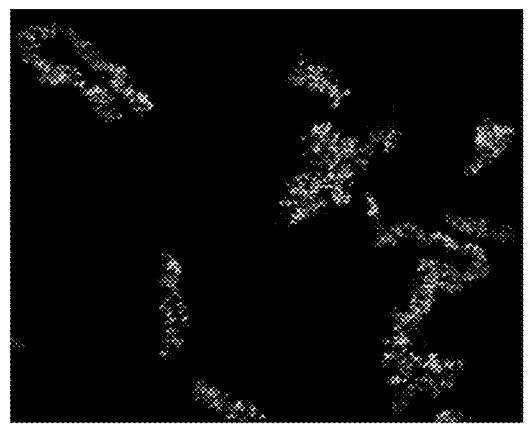

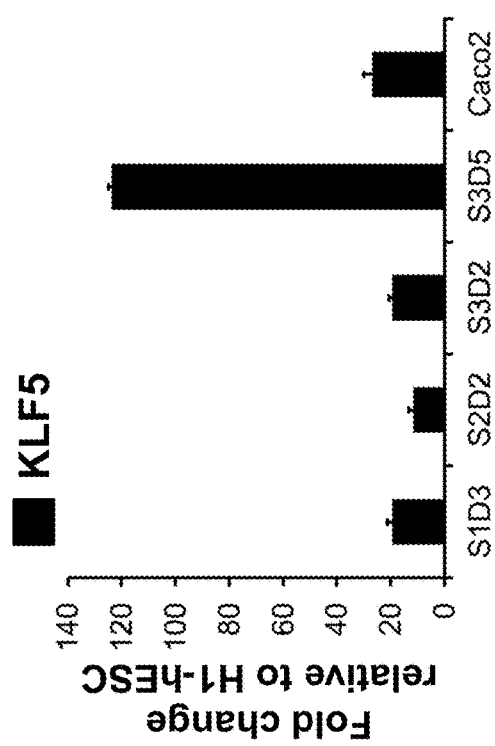
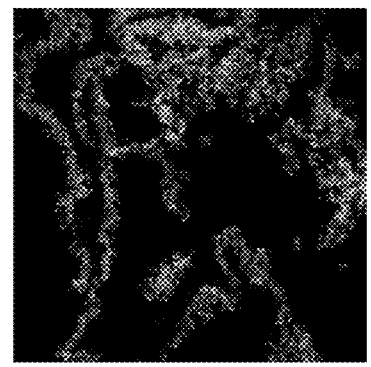

RA BMP2
S3D5

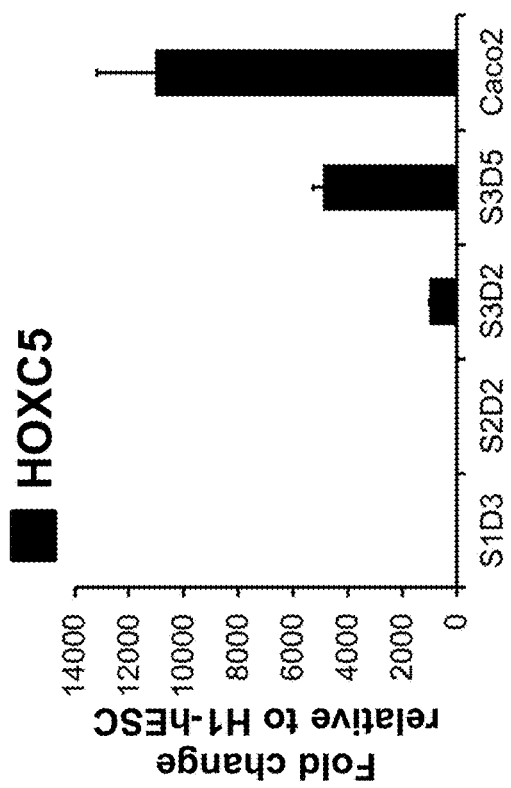

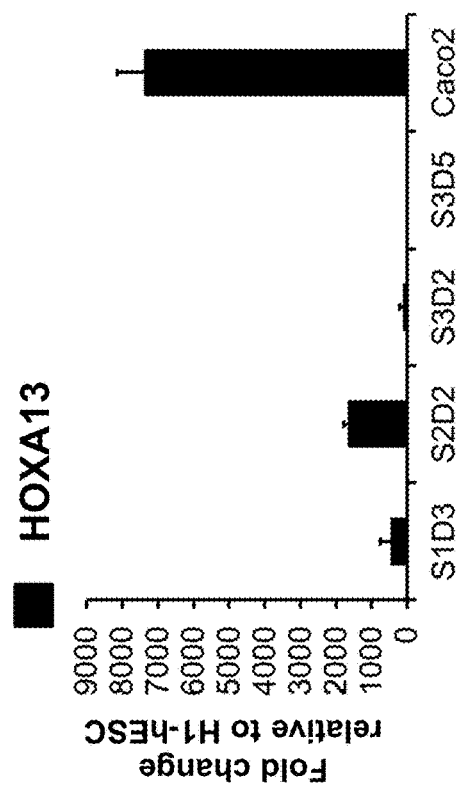

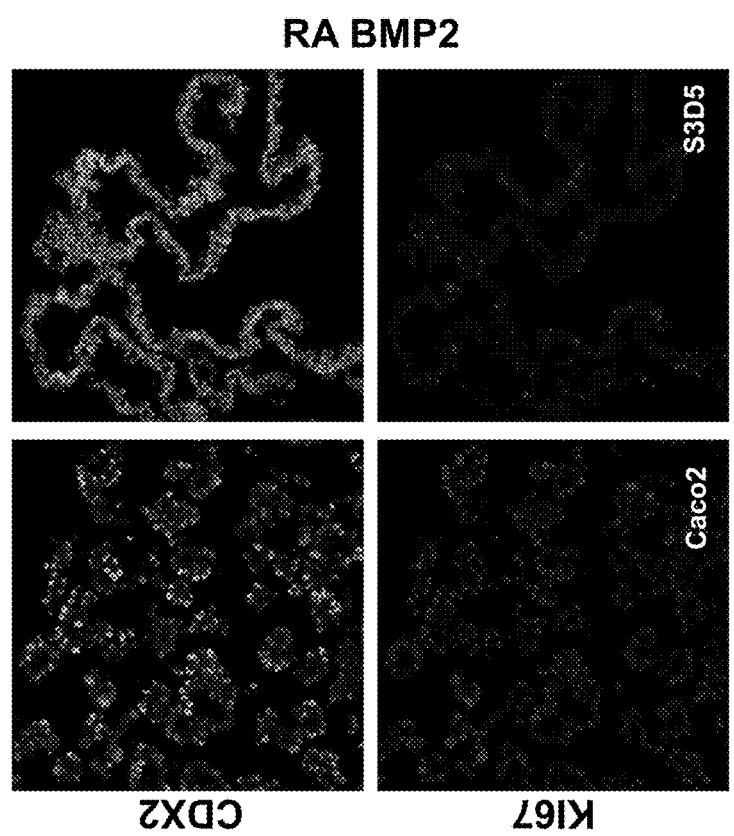

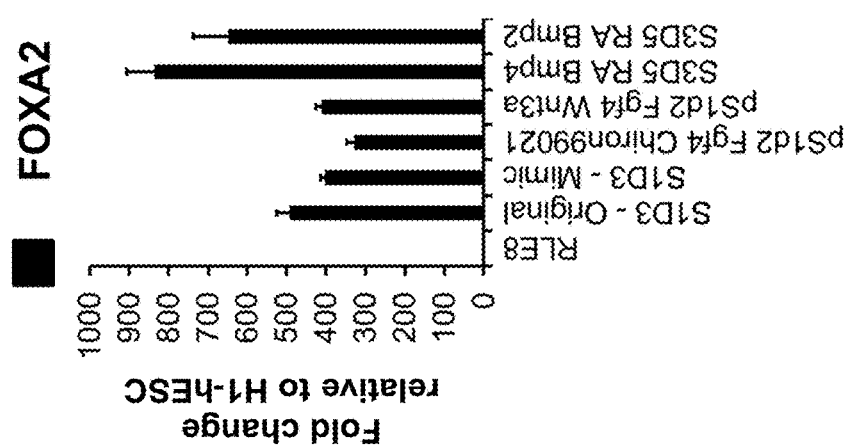

DIFFERENTIATION OF PLURIPOTENT STEM CELLS TO INTESTINAL MIDGUT ENDODERM CELLS

CROSS REFERENCE TO RELATED APPLICATION

This application is a non-provisional application of U.S. patent application No. 62/322,636 filed on Apr. 14, 2016, the contents of which are herein incorporated by reference.

FIELD OF INVENTION

The invention relates to the field of cell-based therapy for conditions such as diabetes. In particular, the invention relates to cell differentiation, including directing differentiation of human pluripotent stem cells to generate a population of intestinal midgut endoderm cells. The invention provides cells or a cell population and methods of producing the cells that express markers characteristic of intestinal midgut endoderm.

BACKGROUND

Advances in the knowledge of incretin hormone mechanism of action coupled with advancements in the understanding of intestinal differentiation, both at the stem cell and endocrine cell stages, have led to interest in developing sources of incretin hormone producing cells, appropriate for engraftment. One approach is the generation of functional enteroendocrine L- or K-cells from pluripotent stem cells, such as human embryonic stem cells ("hESC") or induced pluripotent stem cells ("iPS").

The production/secretion of glucagon-like peptide 1 (GLP-1) from intestinal L-cells or glucose-dependent insulinotropic polypeptide (GIP) from intestinal K-cells has beneficial effects for the treatment of diabetes mellitus. Incretin hormones have systemic effects beneficial for the treatment of diabetes mellitus (Type 1 and Type 2) (Unger, J., Curr Diab Rep., 2013; 13(5):663-668). Benefits may include augmentation of many aspects of beta ((β) cell function and number, suppression of glucagon secretion, increases in the insulin sensitivity of peripheral metabolic tissues, reduction of hepatic gluconeogenesis, and reduction of appetite. Two classes of incretin-based therapeutic agents have been identified for the treatment of diabetes mellitus (GLP-1 receptor agonists and dipeptidyl peptidase 4 (DPP-4) inhibitors). However, there is currently no incretin-based cell therapy option that would encompass an endogenous and cellular barometer for improved and efficient GLP1-based diabetes treatment. Furthermore, current incretin-based therapies are not regulated by circulating blood glucose levels and thus provide non-physiologically regulated GLP production.

In vertebrate embryonic development, a pluripotent cell gives rise to a group of cells comprising three germ layers (ectoderm, mesoderm, and endoderm) in a process known as gastrulation. The mesenchyme tissue is derived from the mesoderm, and is marked by the genes heart and neural crest derivatives expressed 1 (HAND1), and forkhead box F1 (FOXF1), among others. Tissues such as, thyroid, thymus, pancreas, gut and liver, will develop from the endoderm, via an intermediate stage. The intermediate stage in this process is the formation of the definitive endoderm. By the end of gastrulation, the endoderm is partitioned into anterior-posterior domains that can be recognized by the expression of a panel of factors that uniquely mark anterior foregut, posterior foregut, midgut, and hindgut regions of the endoderm.

The level of expression of specific transcription factors ("TFs") may be used to designate the identity of a tissue, as described in Grapin-Botten et al., Trends Genet, 2000; 16(3): 124-130. FOXA2 marks the entire endoderm along the anterior-posterior axis. During transformation of the definitive endoderm into a primitive gut tube, the gut tube becomes regionalized into broad domains that can be observed at the molecular level by restricted gene expression patterns. The anterior foregut is marked broadly by the high expression of SOX2, and encompasses organ domains such as the thyroid, lung, and esophagus. The midgut (includes the duodenum, ileum, jejunum) and hindgut (includes the colon) are marked by high expression of caudal type homeobox 2 (CDX2). The SOX2-CDX2 boundary occurs within the posterior foregut, within which additional TFs mark specific organ domains. The regionalized pancreas domain within the posterior foregut shows a very high expression of PDX1 and very low expression of CDX2 and SOX2. PTF1A is highly expressed in pancreatic tissue. Low PDX1 expression, together with high CDX2 expression marks the duodenum domain. The intestinal endoderm is patterned by specific homeobox (HOX) genes. For example, HOXC5 is preferentially expressed in midgut endoderm cells. In addition, the expression of HOXA13 and HOXD13 are restricted to hindgut endoderm cells. The ALB gene, or albumin 1 protein, marks the earliest liver progenitors in the posterior foregut endoderm (Zaret et al., Curr Top Dev Biol, 2016; 117:647-669).

Strides have been made in improving protocols to generate intestinal endoderm cells from human pluripotent stem cells. For example, the following publications (Spence et al., Nature, 2011; 470(7332):105-109; Watson et al., Nature Medicine, 2014; 20(11):1310-1314; and Kauffman et al., Front Pharmacol, 2013; 4(79):1-18) outline differentiation protocols using either fibroblast growth factor (FGF)-4, Wingless-type MMTV integration site family, member 3A (WNT3A), Chiron 99021, or retinoic acid (RA) and FGF7 starting at the definitive endoderm stage, that generate mid-/hindgut spheroids, containing not only a $CDX2^+$/$FOXA2^+$ endodermal population, but also a significant mesenchymal $CDX2^+$ cell population. The process of differentiating enteroendocrine cells from these hESC-derived mid-/hindgut spheroids is very inefficient, requiring a long time period, and is directed non-discriminately towards the generation of all intestinal cell types of the intervillus and villus regions. A need still exists for technology to generate intestinal midgut endoderm cells, without substantial contaminating mesenchyme, so as to be able to produce with high efficiency intestinal enteroendocrine cells for cell therapeutics.

SUMMARY OF THE INVENTION

As embodied and fully described, the invention provides cells, cell populations and methods of generating the cells by differentiating human pluripotent stem cells. In particular, the invention features methods of directed differentiation of human pluripotent stem cells, to generate intestinal midgut endoderm cells, more particularly an endodermal monolayer of intestinal midgut endoderm cells.

One aspect of the invention is a method of producing a population of intestinal midgut endoderm cells comprising culturing human pluripotent stem cells in culture media. In embodiments, the method comprises inducing differentiation of human pluripotent stem cells to intestinal midgut endoderm cells. In some embodiments, a population of intestinal midgut endoderm cells is produced. In some embodiments, a population of substantially intestinal midgut endoderm cells is produced. In embodiments of the invention, the intestinal midgut endoderm cells form and are stable as a monolayer in culture. In embodiments, greater than 50% of the differentiated cells express markers characteristic of intestinal midgut endoderm, preferably greater than 60% of the differentiated cells express markers characteristic of intestinal midgut endoderm, more preferably greater than 70%, greater than 80%, and greater than 90% express markers characteristic of intestinal midgut endoderm. In embodiments, differentiated cells express markers characteristic of intestinal midgut endoderm are intestinal midgut endoderm cells. In embodiments, the intestinal midgut endoderm cells express CDX2 and FOXA2. In all embodiments, the intestinal midgut endoderm cells express transcription factors selected from SOX9, PDX1, KLF5 and HOXC5. In embodiments, the intestinal midgut endoderm cells do not express transcription factors selected from SOX2, ALB, PTF1A, HOXA13 and LGR5.

In embodiments of the invention, human pluripotent stem cells are differentiated to intestinal midgut endoderm cells by steps including: a) culturing the human pluripotent stem cells in a first culture media containing GDF-8 and a GSK3β inhibitor, such as MCX compound, to induce differentiation into definitive endoderm cells; b) culturing the definitive endoderm cells in a second culture media containing ascorbic acid and FGF7 to induce differentiation into primitive gut tube cells; and c) culturing the primitive gut tube cells in a third culture media containing retinoic acid and BMP2 or BMP4 in acidic conditions to induce differentiation into intestinal midgut endoderm cells. In particular embodiments, acidic conditions is culture with BLAR medium. The pH of the acidic culture can range from 6.8 to 7.2. In the embodiments of the invention, the intestinal midgut endoderm cells form a monolayer in culture. In embodiments, the monolayer of intestinal midgut endoderm cells is maintained in culture.

Another embodiment of the invention is a method of treating a patient suffering from or at risk of developing diabetes comprising differentiating human pluripotent stem cells to intestinal midgut endoderm cells, and administering the differentiated intestinal midgut endoderm cells in a patient with diabetes. In embodiments, diabetes is Type 1 or Type 2. In embodiments, administering the cells may be via implantation, injection or otherwise administration directly or indirectly to the site of treatment. In some embodiments, the intestinal midgut endoderm cells are implanted in the body, such as in subcutaneous space, omentum, liver, kidney, etc. Further embodiments encompass encapsulated delivery of the cells including encapsulation of macro- or micro-encapsulation devices.

A further embodiments of the invention is a method of producing intestinal midgut endoderm cells comprising inducing differentiation of definitive endoderm cells in culture to primitive gut tube cells. In embodiments, the definitive endoderm cells are cultured in culture media containing ascorbic acid and FGF7. In further embodiments, the primitive gut tube cells are cultured in culture media containing retinoic acid and BMP2 or BMP4. The primitive gut tube cells are differentiated to intestinal midgut endoderm cells. In some embodiments, primitive gut tube cells are differentiated to intestinal midgut endoderm cells in acidic conditions (acidic culture media). In particular embodiments, acidic conditions is culture with BLAR medium. The pH of the acidic culture can range from 6.8 to 7.2. In the embodiments, the intestinal midgut endoderm cells form and maintain a monolayer in culture.

In each of the embodiments discussed above, human pluripotent stem cells are human embryonic stem cells or induced pluripotent stem cells. In each of the embodiments above, the intestinal midgut endoderm cells express CDX2 and FOXA2. In all embodiments, the intestinal midgut endoderm cells express transcription factors selected from SOX9, PDX1, KLF5 and HOXC5. In the embodiments, the intestinal midgut endoderm cells do not express transcription factors selected from SOX2, ALB, PTF1A, HOXA13 and LGR5. In the embodiments above, the intestinal midgut endoderm cells express CDX2, FOXA2, SOX9, PDX1, KLF5 and HOXC5. In the embodiments above, the intestinal midgut endoderm cells do not express SOX2, ALB, PTF1A, HOXA13 and LGR5. In embodiments, greater than 50% of the differentiated cells express markers characteristic of intestinal midgut endoderm, preferably greater than 60% of the differentiated cells express markers characteristic of intestinal midgut endoderm, more preferably greater than 70%, greater than 80%, and greater than 90% express markers characteristic of intestinal midgut endoderm. In embodiments, differentiated cells express markers characteristic of intestinal midgut endoderm are intestinal midgut endoderm cells. In embodiments, the intestinal midgut endoderm cells express CDX2 and FOXA2. In embodiments, the intestinal midgut endoderm cells express transcription factors selected from SOX9, PDX1, KLF5 and HOXC5. In embodiments, the intestinal midgut endoderm cells do not express transcription factors selected from SOX2, ALB, PTF1A, HOXA13 and LGR5. In the embodiments, intestinal midgut endoderm cells do not express HAND1.

In the embodiments discussed above, the population of intestinal midgut endoderm cells is substantially intestinal midgut endoderm cells. In some embodiments, the population of intestinal midgut endoderm cells comprises greater than 70% intestinal midgut endoderm cells, preferably greater than 80%, greater than 90%, and greater than 95% of intestinal midgut endoderm cells. In some embodiments, the population of intestinal midgut endoderm cells comprises less than 20% mesenchymal cells, preferably less than 15%, more preferably less than 10%, less than 5%, less than 2%, less than 1%, less than 0.5%. In embodiments, intestinal midgut endoderm cells lack expression of HAND1.

In some embodiments of the invention described above, differentiation is induced in vitro. In other embodiments, intestinal midgut endoderm cells differentiate further in vivo. Another embodiment relates to the intestinal midgut endoderm cells further differentiating into enteroendocrine cells in vivo. The enteroendocrine cells express or secrete incretin hormones. In embodiments, the incretin hormones are GLP1 and GIP.

In a further embodiment, intestinal midgut endoderm cells serve as starting material for the identification of small molecules that promote at high efficiency the in vitro differentiation of intestinal midgut endoderm cells into, first, enteroendocrine precursors, and ultimately, incretin expressing or secreting enteroendocrine cells.

BRIEF DESCRIPTION OF THE DRAWINGS

Figure 1A:
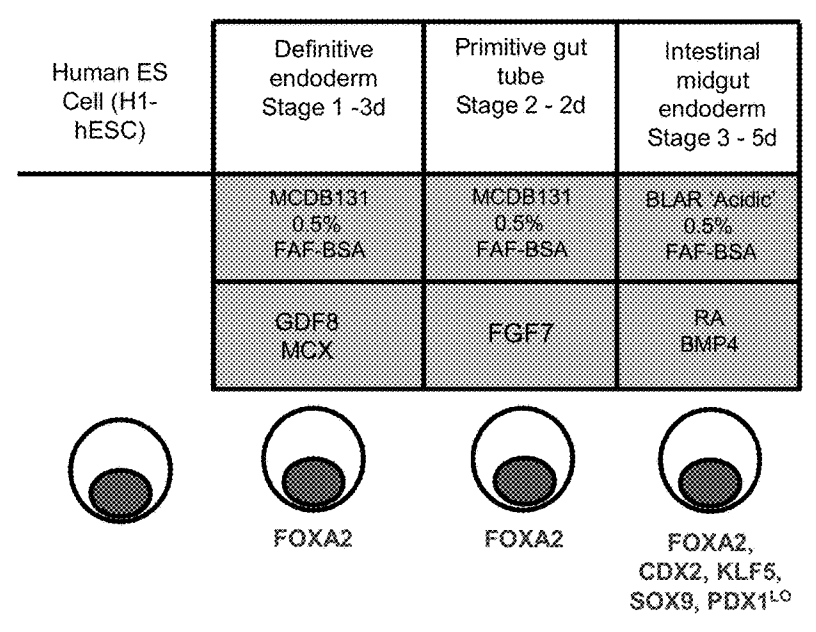

FIGS. 1A-1D depict a differentiation method for intestinal midgut endoderm cells. FIG. 1A is a summary of the differentiation method, including medium components, growth factors and small molecules added to each stage, and key stage-specific markers of the differentiating intestinal midgut endoderm cells (FOXA2, forkhead box A2; CDX2, caudal type homeobox 2; KLF5, Kruppel-like factor 5; SOX9, SRY (sex determining region Y)-box 9; PDX1, pancreatic and duodenal homeobox 1; LO, low expression and protein presence). Compared to the neutral pH noted at S2D2 (7.35±0.04), cells were exposed to slightly acidic conditions in BLAR medium (used interchangeably with "BLAR acidic medium"), during stage 3 (pH; S3D1, 6.98±0.05; S3D2, 7.02±0.04; S3D5, 7.18±0.03) (FIG. 1B), and as a result of lower sodium bicarbonate levels in BLAR medium. FIG. 1C depicts representative phase-contrast images of a S3D5 monolayer (left), and human epithelial colon adenocarcinoma cell line ("Caco-2") (right), which was used as a benchmark for characterization of differentiation. A uniform morphology at S3D5 was consistently observed. Characterization of cell number using the Nucleocounter® NC-100 (Chemometec, Alleroed, Denmark, Catalog No. 900-004) shows that one hESC differentiated into 4.56±2.60 S3D5 intestinal midgut endoderm cells (FIG. 1D).

FIGS. 2A-2D demonstrate the differentiation method, utilizing Bone morphogenic protein-4 (BMP4), generates intestinal midgut endoderm cells in monolayer, comprising both CDX2 and FOXA2 on transcript and protein levels. FIG. 2A (bottom) shows that 90.0±5.85 percent of S3D5 cells were co-present for both CDX2 and FOXA2 protein, similar to percentage seen in Caco-2 cells (86.0±6.67). Conversely, definitive endoderm (DE-S1D3) cells were devoid of CDX2 and FOXA2 co-presence (2.3±1.2). Gene expression analysis shows that CDX2 was induced (FIG. 2B), and FOXA2 maintained (FIG. 2C) during Stage 3. FIG. 2D shows that the induction of CDX2 protein levels and CDX2/FOXA2 protein co-presence after the establishment of the FOXA2-positive primitive gut endoderm stage, S2D2 (FIG. 2D-i), progressively increased through S3D2 (FIG. 2D-ii), and at S3D5 (FIG. 2D-iii) reached similar levels as seen in Caco-2 cells (FIG. 2D-iv). CDX2 protein is depicted on the bottom row, and FOXA2 protein is depicted on the top row. Each image was taken using the same parameters to allow for quantitative analysis. Protein expression was assessed by FACS; gene expression was assessed by qPCR.

FIG. 3A (bottom) demonstrates that 98.7±0.25 percent of cells were co-present for both CDX2 and SOX9 at S3D5. Strong induction of SOX9 gene expression to levels seen in Caco-2 cells (FIG. 3B), and protein presence as assessed by immunofluorescence (IF)-analysis were observed (FIG. 3C). 69.4±14.2 percent of cells were co-positive for both CDX2 and PDX1 (FIG. 3D-bottom). PDX1 gene expression was induced at low levels, when compared to pancreas-biased S4D3 cells (See, e.g., US2014/0242693) (FIG. 3E), and low to absent protein levels was reflected in the IF-analysis (FIG. 3F). Anterior endoderm TF SOX2 was not observed in S3D5 cells, as 1.45±0.15 of S3D5 cells exhibited SOX2 and CDX2 co-presence (FIG. 3G—bottom; FIG. 3Q demonstrates that HOXA13, a marker of the intestinal hindgut endoderm, was not induced in S3D5 cells (FIG. 3P). Gene expression was assessed by qPCR.

FIGS. 4A-4B characterize the proliferative profile of differentiating S3D5 cells. FIG. 4A depicts Caco-2 cells, where most of CDX2-protein positive cells were in active cell cycle (as indicated by the co-expression with KI67 protein) (left), and the proliferative index of the H1-hESC-derived cells during Stage 3 that decreased over time (S3D2—middle; S3D5—right). CDX2 (top row) and KI67 (bottom row) protein levels are depicted as single channel images. The percentage KI67-protein positive cells of total S3D5 cells (total cells are >90% CDX2-positive), assessed by FACS, was 16.8±3.12, in contrast with percentage seen at S1D3 (97.3±1.3), and in Caco-2 cells (99.2±0.2) (FIG. 4B).

FIGS. 5A-5C demonstrate use of BMP2 as an alternative to BMP4, during Stage 3 to achieve a monolayer of intestinal midgut endoderm cells with CDX2 and FOXA2 protein co-presence. FIG. 5A summarizes the differentiation method, including the medium components, growth factors and small molecules that were added to each stage, and stage-specific markers of the differentiating intestinal midgut endoderm cells (FOXA2, CDX2, KLF5, SOX9, and PDX1$^{LO}$). Compared to the neutral pH noted at S2D2 (7.35±0.04), cells were exposed to slightly acidic conditions in BLAR medium, during the entirety of stage 3 (pH; S3D1, 6.92; S3D2, 7.01; S3D5, 7.22) (FIG. 5B), and as a result of lower sodium bicarbonate levels in BLAR medium. FIG. 5C depicts representative phase-contrast images of a S3D5 monolayer (left), and Caco-2 cells (right); a uniform morphology at S3D5 was observed.

FIG. 6A (bottom) shows that 94 percent of S3D5 cells were co-present for both CDX2 and FOXA2 protein, similar to or greater than the percentage seen in Caco-2 cells (86.0±6.67). Gene expression analysis shows CDX2 induced (FIG. 6B), and FOXA2 maintained (FIG. 6C) during Stage 3. FIG. 6U demonstrates that HOXA13, a marker of the intestinal hindgut endoderm, was not induced in S3D5 cells (FIG. 6U).

FIG. 7 characterizes the proliferative profile of differentiating S3D5 cells. Compared to Caco-2 cells, where most of CDX2-protein positive cells were in active cell cycle (as indicated by the co-expression with KI67 protein) (left), the proliferative index of the H1-hESC-derived cells during Stage 3 was lower (S3D5—right). CDX2 (top row) and KI67 (bottom row) protein levels are depicted as single channel images. The percentage KI67-protein positive cells of total S3D5 cells (total cells are >90% CDX2-positive), assessed by FACS, was 14.1 percent, in contrast with percentage seen at S1D3 (97.3±1.3), and in Caco-2 cells (99.2±0.2).

FIGS. 8A-8F demonstrate the induction of a heterogeneous population of CDX2$^+$ cells. FIG. 8A is a summary of the differentiation methods, including medium components, growth factors and small molecules added to each stage, and key stage-specific markers of the differentiating intestinal mid-/hindgut endoderm cells (HAND1). FIG. 8B shows phase-contrast images of H1-hESC cells (top row, left), post-Stage 1 cells conditioned two days with 500 ng/ml FGF4 and 3 µM Chiron99021 (top row, middle), post-Stage 1 cells conditioned two days with 500 ng/ml FGF4 and 500 ng/ml WNT3A (top row, right), a S3D5 monolayer conditioned by RA/BMP4 (bottom row, left), and a S3D5 monolayer conditioned by RA/BMP2 (bottom row, right). The induction of gene expression after two days of conditioning is shown for CDX2 at low levels (FIG. 8C), is maintained for the endoderm marker FOXA2 (FIG. 8D), and is induced for the mesoderm/mesenchyme marker HAND1 (FIG. 8F). KLF5 was not induced (FIG. 8E).

DETAILED DESCRIPTION OF THE INVENTION

Figures 1C, 1D:
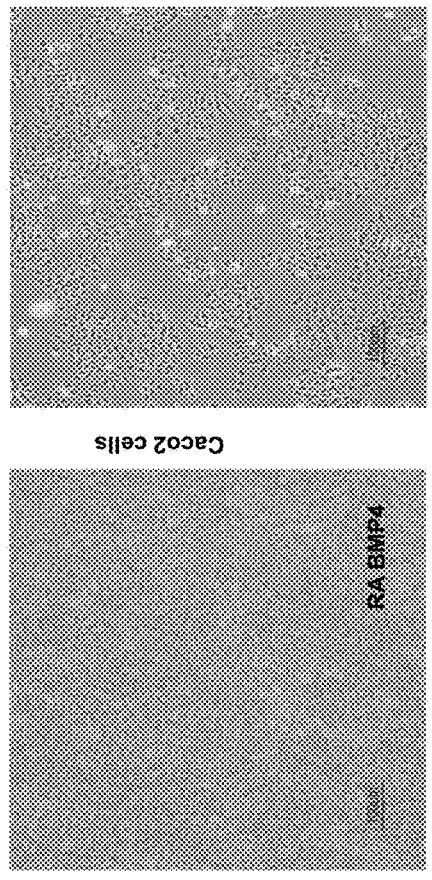

It is to be understood that this invention is not limited to particular methods, reagents, compounds, compositions or biological systems, which can, of course, vary. It is also to be understood that the terminology used herein is for the purpose of describing particular embodiments only, and is not intended to be limiting.

The present invention pertains to the generation of intestinal midgut endoderm cells. The cells were generated using a specific culturing sequence. Accordingly, the present invention provides an in vitro cell culture for differentiating cells derived from pluripotent stem cells into cells expressing markers characteristic of the intestinal midgut endoderm cell lineage, such as expression of CDX2 and FOXA2. The invention further provides a method for obtaining and maintaining such cells in a monolayer via an in vitro cell culture.

In certain embodiments, the invention is based on the discovery that the inclusion of retinoic acid and BMP4 or BMP2 or analogues thereof, act to induce CDX2 and maintain FOXA2 protein expression in differentiating cells to facilitate differentiation towards intestinal midgut endoderm cells. CDX2 is not expressed at the protein level at definitive endoderm (Stage 1) or primitive gut tube (Stage 2). Accordingly, the present invention provides methods of differentiating pluripotent stem cells to generate intestinal midgut endoderm cells that express CDX2 and FOXA2.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent are able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. Induced pluripotent stem cells (iPS cells) are adult cells that are converted into pluripotent stem cells. (Takahashi et al., Cell, 2006; 126(4):663-676; Takahashi et al., Cell, 2007; 131:1-12). An embryonic stem cell is a pluripotent cell from the inner cell mass of a blastocyst-stage embryo. A fetal stem cell is one that originates from fetal tissues or membranes.

Embryonic tissue is typically defined as tissue originating from the embryo (which in humans refers to the period from fertilization to about six weeks of development). Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as an intestinal cell or pancreatic cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e. which cells it came from and what cells it can give rise to. The lineage of a cell places the cell within a hereditary scheme of development and differentiation.

In a broad sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

"Markers", as used herein, are nucleic acid or polypeptide molecules that are differentially expressed in a cell of interest. In this context, differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is sufficiently detected in the cell. Similarly, the cell is "negative for" a specific marker, or "negative" when the specific marker is not sufficiently detected in the cell. In particular, positive by fluorescence-activated flow cytometry (FACS) is usually greater than 2%, whereas the negative threshold by FACS is usually less than 1%.

As used herein, positive by real-time PCR (RT-PCR) had less than 28 cycles (Cts), and using Taqman® Low Density Array (TLDA) had less than 33 Cts; whereas negative by Open Array® is more than 28.5 cycles and negative by TLDA is more than 33.5 Cts.

To differente pluripotent stem cells into functional intestinal midgut endoderm cells in static in vitro cell culture, the differentiation process is often viewed as progressing through consecutive stages. Here, the differentiation process to intestinal midgut endoderm occurs through three stages In this step-wise progression, "Stage 1" refers to the first step in the differentiation process, the differentiation of pluripotent stem cells into cells expressing markers characteristic of definitive endoderm cells (hereinafter referred to alternatively as "Stage 1 cells"). "Stage 2" refers to the second step, the differentiation of cells expressing markers characteristic of definitive endoderm cells into cells expressing markers characteristic of primitive gut tube cells (hereinafter referred to alternatively as "Stage 2 cells"). "Stage 3" refers to the third step, the differentiation of cells expressing markers characteristic of gut tube cells into cells expressing markers characteristic of intestinal midgut endoderm cells (hereinafter referred to alternatively as "Stage 3 cells").

However, it should be noted that not all cells in a particular population progress through these stages at the same rate. Consequently, it is not uncommon in in vitro cell cultures to detect the presence of cells that have progressed less, or more, down the differentiation pathway than the majority of cells present in the population, particularly at the later differentiation stages. For purposes of illustrating the present invention, characteristics of the various cell types associated with the above-identified stages are described herein.

"Definitive endoderm cells," as used herein, refers to cells which bear the characteristics of cells arising from the epiblast during gastrulation and which form the gastrointestinal tract and its derivatives. Definitive endoderm cells express at least one of the following markers: FOXA2 (also known as hepatocyte nuclear factor 3-β ("HNF3β")), GATA4, SOX17, CXCR4, Brachyury, Cerberus, OTX2, goosecoid, C-Kit, CD99, and MIXL1. Markers characteristic of the definitive endoderm cells include CXCR4, FOXA2 and SOX17. Thus, definitive endoderm cells may be characterized by their expression of CXCR4, FOXA2 and SOX17. In addition, depending on the length of time cells are allowed to remain in Stage 1, an increase in HNF4α may be observed.

"Primitive gut tube cells," as used herein, refers to endoderm cells derived from definitive endoderm that can give rise to all endodermal organs, such as lungs, liver, pancreas, stomach, and intestine. Primitive gut tube cells may be characterized by their substantially increased expression of HNF4α over that expressed by definitive endoderm cells.

"Foregut endoderm cells," as used herein, refers to endoderm cells that give rise to the esophagus, lungs, stomach, liver, pancreas, gall bladder, and the most anterior portion of the duodenum. Foregut endoderm cells may be characterized by their expression of SOX2, PDX1, ALB, SOX17 and FOXA2, among others.

"Intestinal midgut endoderm cell," as used herein, refers to endoderm cells that give rise to small intestine. Intestinal midgut endoderm cells may be characterized by their expression of CDX2, FOXA2, and low expression of PDX1 ($PDX1^{LO}$). The expression of certain HOX genes can distinguish between midgut and hindgut endoderm. For example, HOXC5 is preferentially expressed in midgut endoderm cells.

"Hindgut endodermal cell" as used herein, refers to endoderm cells that give rise to large intestine. Hindgut endoderm cells may be characterized by their expression of CDX2, FOXA2, HOXA13 and HOXD13.

"Mesenchyme cell," as used herein, refers to mesoderm cells that give rise to connective tissues, such as bones, cartilage, lymphatic, and circulatory systems. Expression of HAND1 and FOXF1 define mesenchyme cells.

The term "patient" or "subject" or "host" refers to animals, including mammals, preferably humans, who are treated with compositions or pharmaceutical compositions, or in accordance with the methods described herein.

The term "effective amount" or equivalents thereof refers to an amount of an agent or compound including but not limited to a growth factor, which is sufficient to promote and differentiate human pluripotent stem cells to a differentiated cell population, for example, to a definitive endoderm, foregut endoderm, intestinal midgut endoderm, hindgut endoderm, pancreatice endoderm and the like.

The terms "administering" and "administration" are used interchangeably herein and mean the cells may be implanted, injected, transplanted or otherwise administered directly or indirectly to the site of treatment. When cells are administered in semi-solid or solid devices, implantation is a suitable means of delivery, particularly surgical implantation into a precise location in the body, such as into subcutaneous space, omentum, liver, kidney (kidney capsule). Liquid or fluid pharmaceutical compositions may be administered to a more general location.

As used in this specification and the appended claims, the singular forms "a", "an" and "the" include plural referents unless the content clearly dictates otherwise. Thus, for example, reference to "a cell" includes a combination of two or more cells, and the like.

As used herein, the term "about" when referring to a measurable value such as an amount, a temporal duration, and the like, is meant to encompass variations of between ±20% and ±0.1%, preferably ±20% or ±10%, more preferably ±5%, even more preferably ±1%, and still more preferably ±0.5%, ±0.1%. 0.05% or 0.01% of the specified value, as such variations are appropriate to perform the disclosed methods.

The following abbreviations may appear throughout the specification and claims:

ABCG2—ATP-Binding Cassette, Sub-Family G, Member 2;
ALB—albumin;
BMP—bone morphogenic protein;
CDX2—caudal type homeobox 2;
CXCR4—C—X—C chemokine receptor type 4;
FAF-BSA—Fatty-acid Free Bovine Serum Albumin
FGF—fibroblast growth factor;
FOXA2—Forkhead Box A2;
GATA4—GATA binding protein 4;
GDF—growth differentiation factor;
GIP—glucose-dependent insulinotropic polypeptide;
GLP-1—glucagon-like peptide 1;
GSK3B—Glycogen synthase kinase 3 beta;
HAND1—heart and neural crest derivatives expressed 1;
HOX—homeobox;
hTERT—human telomerase reverse transcriptase;
KLF—Kruppel-like factor;
LGR5—leucine rich repeat containing G protein coupled receptor 5;
MIXL1—Mix Paired-Like Homeobox-1;
OCT4—octamer-binding transcription factor 4;
OTX2—orthodenticle homeobox 2;
PDX1—pancreatic and duodenal homeobox 1;
PTF1A—pancreas specific transcription factor, 1a;
SOX—sex determining region Y (SRY)-box;
TRA1-60—T cell receptor alpha-1-60;
UTF1—Undifferentiated embryonic cell transcription factor 1;
WNT3A—wingless-type MMTV integration site family, member 3A; and
ZFP42—zinc finger protein 42.

DETAILED DESCRIPTION

Pluripotent stem cells have the potential to differentiate into cells of all three germinal layers: endoderm, mesoderm, and ectoderm tissues. Exemplary types of pluripotent stem cells that may be used include established lines of pluripotent cells, including pre-embryonic tissue (such as, for example, a blastocyst), embryonic tissue, or fetal tissue taken any time during gestation, typically but not necessarily, before approximately 10 to 12 weeks gestation. Non-limiting examples are established lines of human embryonic stem cells or human embryonic germ cells, such as, for example the human embryonic stem cell lines H1, H7, and H9 (WiCell Research Institute, Madison, Wis., USA). Cells taken from a pluripotent stem cell population already cultured in the absence of feeder cells are also suitable. iPS, or reprogrammed pluripotent cells, derived from adult somatic cells using forced expression of a number of pluripotent related transcription factors, such as OCT4, NANOG, SOX2, KLF4, and ZFP42 (*Annu Rev Genomics Hum Genet* 2011, 12:165-185; see also iPS, *Cell*, 126(4): 663-676) may also be used. The human embryonic stem cells used in the methods of the invention may also be prepared as described by Thomson et al. (U.S. Pat. No. 5,843,780; *Science*, 1998, 282:1145-1147; *Curr Top Dev Biol* 1998, 38:133-165; *Proc Natl Acad Sci U.S.A.* 1995, 92:7844-7848). Mutant human embryonic stem cell lines, such as, BG01v (BresaGen, Athens, Ga.), or cells derived from adult human somatic cells, such as, cells disclosed in Takahashi et al., *Cell* 131: 1-12 (2007) may also be used. In certain embodiments, pluripotent stem cells suitable for use in the present invention may be derived according to the methods described in: Li et al. (*Cell Stem Cell* 4: 16-19, 2009); Maherali et al. (*Cell Stem Cell* 1: 55-70, 2007); Stadtfeld et al. (*Cell Stem Cell* 2: 230-240); Nakagawa et al. (*Nature Biotechnol* 26: 101-106, 2008); Takahashi et al. (*Cell* 131: 861-872, 2007); and U.S. Patent App. Pub. No. 2011/0104805. In certain embodiments, the pluripotent stem cells may be of non-embryonic origins. All of these references, patents, and patent applications are herein incorporated by reference in their entirety, in particular, as they pertain to the isolation, culture, expansion and differentiation of pluripotent cells.

Pluripotent stem cells differentiate through various stages each of which may be characterized by the presence or absence of particular markers. Differentiation of the cells into these stages is achieved by the specific culturing conditions, including the presence or lack of certain factors added to the culture media. In general, this differentiation may involve differentiation of pluripotent stem cells into definitive endoderm cells, referred to herein as Stage 1. These definitive endoderm cells may then be further differentiated into primitive gut tube cells, referred to herein as Stage 2. Primitive gut tube cells in turn may then be differentiated into intestinal midgut endoderm cells, referred to herein as Stage 3.

Differentiation of Pluripotent Stem Cells into Cells Expressing Markers Characteristic of Intestinal Midgut Endoderm Cells Characteristics of pluripotent stem cells are well known to those skilled in the art, and additional characteristics of pluripotent stem cells continue to be identified. Pluripotent stem cell markers include, for example, the expression of one or more of the following: ABCG2; Cripto; FOXD3;

CONNEXIN43; CONNEXIN45; OCT4; SOX2; NANOG; hTERT; UTF1; ZFP42; SSEA-3; SSEA-4; TRA-1-60; and TRA-1-81.

Exemplary pluripotent stem cells include the human embryonic stem cell line H1 (NIH code: WA01), the human embryonic stem cell line H9 (NIH code: WA09), the human embryonic stem cell line H7 (NIH code: WA07), and the human embryonic stem cell line SA002 (Cellartis, Sweden). Also suitable are cells that express at least one of the following markers characteristic of pluripotent cells: ABCG2, Cripto, CD9, FOXD3, CONNEXIN43, CONNEXIN45, OCT4, SOX2, NANOG, hTERT, UTF1, ZFP42, SSEA-3, SSEA-4, TRA-1-60, and TRA-1-81.

Also suitable for use in the present invention is a cell that expresses at least one of the markers characteristic of the definitive endoderm lineage. In one embodiment of the invention, a cell expressing markers characteristic of the definitive endoderm lineage is a primitive streak precursor cell. In an alternate embodiment, a cell expressing markers characteristic of the definitive endoderm lineage is a mesendoderm cell. In an alternate embodiment, a cell expressing markers characteristic of the definitive endoderm lineage is a definitive endoderm cell.

Also suitable for use in the present invention is a cell that expresses at least one of the markers characteristic of the intestinal midgut endoderm lineage. In one embodiment of the present invention, a cell expressing markers characteristic of the intestinal endoderm lineage is an intestinal midgut endoderm cell in which the cell expresses FOXA2 and CDX2. In some embodiments, the cell does not express SOX2, ALB, PTF1A, HOXA13 or LGR5. In embodiments, a cell expressing markers characteristic of the intestinal endoderm lineage is an intestinal midgut endoderm cell in which the cell expresses each of FOXA2, CDX2, SOX9, PDX1, KLF5 and HOXC5. In embodiments, a cell expressing markers characteristic of the intestinal midgut endoderm lineage is an intestinal midgut endoderm cell in which the cell does not express any of SOX2, ALB, PTF1A, HOXA13 and LGR5.

The invention provides for staged, directed differentiation of pluripotent stem cells toward intestinal midgut endoderm cells using cell culture conditions and media. In embodiments of the invention, to arrive at a cell expressing markers characteristic of intestinal midgut endoderm cell, a protocol starting with pluripotent stem cells, such as embryonic stem cells and induced pluripotent cells, is employed. This protocol includes the following stages.

Stage 1: Pluripotent stem cells, such as embryonic stem cells obtained for cell culture lines, are treated with appropriate factors to induce differentiation into cells expressing markers characteristic of definitive endoderm cells.

Stage 2: Cells resulting from Stage 1 are treated with appropriate factors to induce further differentiation into cells expressing markers characteristic of primitive gut tube cells.

Stage 3: Cells resulting from Stage 2 are treated with appropriate factors to induce further differentiation into cells expressing markers characteristic of intestinal midgut endoderm cells.

Methods for assessing expression of protein and nucleic acid markers in cultured or isolated cells are standard in the art. These methods include RT-PCR, Northern blots, in situ hybridization (see, e.g., Current Protocols in Molecular Biology (Ausubel et al., eds. 2001 supplement)), and immunoassays (such as immunohistochemical analysis of sectioned material), Western blotting, and for markers that are accessible in intact cells, FACS (see, e.g., Harlow and Lane, Using Antibodies: A Laboratory Manual, New York: Cold Spring Harbor Laboratory Press (1998)). The efficiency of differentiation may be determined by exposing a treated cell population to an agent (such as an antibody) that specifically recognizes a protein marker expressed by cells expressing markers characteristic of the cell type of interest.

1. Differentiation of Pluripotent Stem Cells Into Cells Expressing Markers Characteristic of Definitive Endoderm Cells Pluripotent stem cells may be differentiated into cells expressing markers characteristic of definitive endoderm cells by any suitable method known in the art, or by any method proposed in this invention. In one embodiment of the invention, pluripotent stem cells are treated with a medium, such as MCDB-131 medium (Life Technologies, Carlsbad, Calif.) supplemented with factors including GDF8 and a GSK3β inhibitor (such as the cyclic aniline-pyridinotriazine compounds disclosed in U.S. Patent App. Pub. No. 2010/0015711; incorporated herein by reference in its entirety) to induce differentiation into cells expressing markers characteristic of definitive endoderm cells. There is a broad range of GSK3β inhibitors, such as staurosporine, and the preferred GSK3β inhibitor (14-Prop-2-en-1-yl-3,5,7,14, 17,23,27-heptaazatetracyclo [19.3.1.1~2,6~0.1~8,12~]heptacosa-1(25),2(27),3,5,8(26),9,11,21,23-nonaen-16-one, referred to herein as "MCX Compound". Treatment may involve contacting pluripotent stem cells with a medium supplemented with about 10 ng/ml to 1000 ng/ml, preferably 50 ng/ml to about 150 ng/ml, alternatively about 75 ng/ml to about 125 ng/ml, alternatively about 100 ng/ml of GDF8. The treatment may also involve contacting the cells with about 0.1 to 10 µM, preferably about 0.1 to 5 alternatively about 0.5 to about 2.5 preferable about 1.5 µM or about 1.0 µM of MCX compound. Other components of the medium may include: Sodium bicarbonate at about 2.7 g/1000 ml to 3.6 g/1000 ml, preferably 2.7 g/1000 ml; FAF-BSA at about 0.1% to 2.0%, preferably about 0.5%; GlutaMAX™ (Life Technologies Corporation, Carlsbad, Calif.) at 1:100 dilution ("1× concentration"); and D-Glucose at a concentration range of about 2 mM to 20 mM, preferably 4.5 mM to obtain a concentration of 10 mM D-Glucose.

The pluripotent cells may be cultured for approximately two to five days, preferably about three to four days, to facilitate their differentiation into definitive endoderm cells. In one embodiment, the pluripotent cells are cultured in the presence of an effective amount of TGFβ signaling molecule and/or GSK3β inhibitor, for example, an effective amount of GDF8 and MCX compound for one day, followed by culturing in the presence of GDF8 and a lower concentration of MCX compound for one day, followed by culturing in the presence of GDF8 for one day in the absence of the MCX compound. In particular, the cells may be cultured in the presence of GDF8 and about 1.5 µM of MCX compound for one day, followed by culturing in the presence of GDF8 and about 0.1 µM MCX compound for one day, followed by culturing in the presence of GDF8 for one day in the absence of the MCX compound. In an alternate embodiment, the cells may be cultured in the presence of GDF8 and about 1.5 µM of MCX compound for one day, followed by culturing in the presence of GDF8 and about 0.1 µM MCX compound for one day.

Generation of cells expressing markers characteristic of definitive endoderm cells may be determined by testing for the presence of the markers before and after following a particular protocol. Pluripotent stem cells typically do not express such markers. Thus, differentiation of pluripotent cells can be detected when the cells begin to express markers characteristic of definitive endoderm cells, such as CXCR4, FOXA2 and SOX17. In the embodiments, cells expressing markers characteristic of definitive endoderm cells are definitive endoderm cells.

2. Differentiation of Cells Expressing Markers Characteristic of Definitive Endoderm Cells Into Cells Expressing Markers Characteristic of Primitive Gut Tube Cells The cells expressing markers characteristic of definitive endoderm cells may be further differentiated into cells expressing markers characteristic of primitive gut tube cells. In one embodiment, the formation of cells expressing markers characteristic of primitive gut tube cells includes culturing cells expressing markers characteristic of definitive endoderm cells with a medium, such as MCDB-131, containing FGF7 to differentiate these cells. For example, the culture medium may include from about 10 ng/ml to 100 ng/ml, preferably about 25 ng/ml to about 75 ng/ml, alternatively from about 30 ng/ml to about 60 ng/ml, alternatively about 50 ng/ml of FGF7. The cells may be cultured under these conditions for about two to three days, preferably about two days.

In another embodiment, differentiation into cells expressing markers characteristic of primitive gut tube cells includes culturing cells expressing markers characteristic of definitive endoderm cells with FGF7 and ascorbic acid (vitamin C). The culture medium, such as MCDB-131, may include from about 0.1 mM to about 1.0 mM ascorbic acid, preferably about 0.1 mM to about 1.0 mM, alternatively from about 0.2 mM to about 0.4 mM, alternatively about 0.25 mM of ascorbic acid. The culture medium may also include from about 10 ng/ml to 100 ng/ml, preferably about 10 ng/ml to about 50 ng/ml, alternatively from about 15 ng/ml to about 30 ng/ml, alternatively about 50 ng/ml or about 25 ng/ml of FGF7. For example, the culture medium may include about 0.25 mM ascorbic acid and about 50 ng/ml FGF7. Other components of the medium may include: sodium bicarbonate at about 2.7 g/1000 ml to 3.6 g/1000 ml, preferably 2.7 g/1000 ml; FAF-BSA at about 0.1% to 2.0%, preferably about 0.5%; GlutaMAX™ at 1:100 dilution ("1× concentration"); and D-Glucose at a concentration range of about 2 mM to 20 mM, preferably 4.5 mM to obtain a concentration of 10 mM D-Glucose. In one embodiment, cells expressing markers characteristic of definitive endoderm cells are treated for 2 days with FGF7 and ascorbic acid. Differentiation of definitive endoderm cells can be detected when the cells begin to express markers characteristic of primitive gut tube cells, such as expression of FOXA2 and increased expression of HNF4α. In the embodiments, cells expressing markers characteristic of primitive gut tube cells are primitive gut tube cells.

3. Differentiation of Cells Expressing Markers Characteristic of Primitive Gut Tube Cells Into Cells Expressing Markers Characteristic of Intestinal Midgut Endoderm Cells Cells expressing markers characteristic of primitive gut tube cells may be further differentiated into cells expressing markers characteristic of intestinal midgut endoderm cells. In one embodiment, primitive gut tube cells are further differentiated into intestinal midgut endoderm cells by culturing the primitive gut tube cells in a culture medium, such as BLAR medium (Life Technologies, Corporation, Carlsbad, Calif.), supplemented with retinoic acid and a BMP4 or BMP2. In a preferred embodiment, the medium is supplemented with from about 0.5 µM to about 5 µM of retinoic acid, preferably about 1 and from about 10 ng/ml to about 100 ng/ml BMP4 or BMP2, preferably about 50 ng/ml of BMP4 or BMP2. Other supplements to the medium may include: FAF-BSA at about 0.1% to 2.0%, preferably about 0.5%; GlutaMAX™; and D-Glucose at a concentration range of about 2 mM to 20 mM, preferably 4.5 mM to obtain a concentration of 10 mM D-Glucose. In one embodiment, cells expressing markers characteristic of primitive gut cells are treated for 3 to 5 days, preferably for 5 days with BMP4 or BMP2 and retinoic acid. The pH of the culture can range from 6.8 to 7.2 during the 5-day Stage 3 conditioning period (compared to normal pH at S2D2 being 7.3 or more).

The invention relates to a method of producing a population of intestinal midgut endoderm cells by culturing human pluripotent stem cells in selected culture media for generating intestinal midgut endoderm cells. In embodiments, the method induces differentiation of human pluripotent stem cell to intestinal midgut endoderm cells in a staged process. In embodiments, a population of intestinal midgut endoderm cells is produced. In some embodiments, a population of substantially intestinal midgut endoderm cells is produced. In the embodiments, the intestinal midgut endoderm cells form and maintain a monolayer on planar culture. In embodiments, the intestinal midgut endoderm cells are stable as a monolayer in culture. Cells stable as a monolayer, or remain stable as a monolayer, herein refers to a monolayer of cells that do not form spheroids in culture.

In embodiments, greater than 50% of the differentiated cells express markers characteristic of intestinal midgut endoderm. In embodiments, greater than 60%, greater than 70%, greater than 80%, greater than 90% or greater than 95% of the differentiated cells express markers characteristic of intestinal midgut endoderm. In embodiments, differentiated cells express markers characteristic of intestinal midgut endoderm are intestinal midgut endoderm cells. In embodiments, the intestinal midgut endoderm cells express CDX2 and FOXA2 as determined by FACS analysis and qPCR. In some embodiments, intestinal midgut endoderm cells express transcription factors selected from SOX9, PDX1, KLF5 and HOXC5 as determined by IF analysis and qPCR. In embodiments, the intestinal midgut endoderm cells do not express transcription factors selected from SOX2, ALB, PTF1A as determined by IF analysis and qPCR, and HOXA13 and LGR5 as determined by qPCR.

A further embodiment of the invention is a method of producing intestinal midgut endoderm cells comprising inducing differentiation of definitive endoderm cells in culture to primitive gut tube cells. In embodiments, the definitive endoderm cells are cultured in culture media containing ascorbic acid and FGF7. In further embodiments, the primitive gut tube cells are cultured in culture media containing retinoic acid and BMP2 or BMP4. The primitive gut tube cells are differentiated to intestinal midgut endoderm cells. In some embodiments, primitive gut tube cells are differentiated to intestinal midgut endoderm cells in acidic conditions (acidic culture media). In particular embodiments, acidic conditions is culture in BLAR media. The pH of the acidic culture can range from 6.8 to 7.2 during the 5-day differentiation conditioning period from primitive gut tube cells to intestinal midgut endoderm cells (compared to normal pH at S2D2 being 7.3 or more). In the embodiments, the intestinal midgut endoderm cells form and maintain a monolayer in culture.

In each of the embodiments discussed herein, human pluripotent stem cells are human hESC or iPS cells. In each of the embodiments above and herein, the intestinal midgut endoderm cells express CDX2 and FOXA2 as determined by FACS analysis and qPCR. In all embodiments, the intestinal midgut endoderm cells express transcription factors selected from SOX9, PDX1, KLF5 and HOXC5 as determined by IF analysis and qPCR. In the embodiments above and herein, the intestinal midgut endoderm cells do not express transcription factors selected from SOX2, ALB, PTF1A as determined by IF analysis and qPCR, and HOXA13 and LGR5 as determined by qPCR. In the embodiments above and herein, the intestinal midgut endoderm cells express CDX2, FOXA2, SOX9, PDX1, KLF5 and HOXC5 by IF analysis and qPCR. In each of the embodiments, the intestinal midgut endoderm cells do not express SOX2, ALB and PTF1A as determined by IF analysis and qPCR, and HOXA13 and LGR5 as determined by qPCR.

As a result of the differentiation protocol described above and herein, using specific culture components and culture conditions, in particular acidic culture condition, such as culture in BLAR medium, a culture of cells expressing markers for intestinal midgut endoderm cells is generated; the cells lack expression of HAND1 as determined by qPCR, a marker of mesoderm/mesenchymal lineage. Varying the differentiation protocol to induce pluripotent stem cells to midgut/hindgut endoderm lineage, such as inducing stem cells at definitive endoderm stage 1 rather than primitive gut tube cell stage 2, results in a mixed population of endoderm-mesenchyme CDX2+mid-/hindgut cells that express HAND1 as determined by qPCR.

In certain embodiments, the population of intestinal midgut endoderm cells is substantially intestinal midgut endoderm cells. In some embodiments, the population of intestinal midgut endoderm cells comprises greater than 70% intestinal midgut endoderm cells, preferably greater than 80%, greater than 90%, and greater than 95% of intestinal midgut endoderm cells. In some embodiments, the population of intestinal midgut endoderm cells comprises less than 20% mesenchymal cells, preferably less than 15%, more preferably less than 10%, less than 5%, less than 2%, less than 1%, less than 0.5%. In embodiments, intestinal midgut endoderm cells lack expression of HAND1.

Use of Differentiated Intestinal Midgut Endoderm Cells

In another embodiment of the invention, the differentiated intestinal midgut endoderm cells may be used for treating a patient suffering from or at risk of developing diabetes alone or in combination with differentiated or mature endocrine cells, for example, enteroendocrine cells. In such embodiments, differentiated intestinal midgut endoderm cells, or mixtures thereof, may be administered to a patient having diabetes, for example Type 1 or Type 2 diabetes. In embodiments, intestinal midgut endoderm cells differentiate and mature to enteroendocrine cells. In embodiments, intestinal midgut endoderm cells differentiate and mature to enteroendocrine cells, and the enteroendocrine cells express or secrete incretin type hormones. In embodiments, incretin hormones include GLP1 and GIP. Administration of the cells may be via implantation or injection in the body, in particular implantation into subcutaneous space, omentum, liver, kidney, etc.

In some embodiments of the invention described above, differentiation of intestinal midgut endoderm cells is induced in vitro. In other embodiments, intestinal midgut endoderm cells further differentiate and mature in vivo. Another embodiment relates to the intestinal midgut endoderm cells further differentiating into enteroendocrine cells in vivo or in a mixture with enteroendocrine cells in vivo. Such enteroendocrine cells express or secrete incretin hormones. In embodiments, the enteroendocrine cell-secreted incretin hormones include GLP1 and GIP.

In a further embodiment, intestinal midgut endoderm cells serve as starting material for the identification of small molecules that promote at high efficiency the in vitro differentiation of intestinal midgut endoderm cell type into, first, enteroendocrine precursors, and then to incretin expressing or secreting enteroendocrine cells.

Cells and cell populations and mixtures such as those described herein may be micro- or macro-encapsulated and subsequently transplanted into a mammalian host. Encapsulated cells or cells alone may be transplanted (administered) subcutaneously or anywhere else in the body whereby the cells may be vascularized and differentiate and mature in vivo.

EXAMPLES

The invention can be further understood in view of the following non-limiting examples.

Example 1

Method of Producing an Intestinal Midgut Endoderm Cell Population With CDX2 and FOXA2 Co-presence/Co-expression The following example describes a directed-based method to generate intestinal midgut endoderm cells from human embryonic stem cell ("hESC"). "Intestinal midgut endoderm" refers to a corresponding in vivo or in situ cell type which is CDX2-positive and FOXA2-positive endoderm cells present at about embryonic day 8.5 ("E8.5") during mouse development, or at about the 3-4 week time point during human embryonic development.

Materials and Methods

Cell culture: Cells of the human embryonic stem cell line H1 ("H1-hESC") (WA01 cells, WiCell Research Institute, Madison, Wis. cultured with EZ8 media (Cat #A1516901 Gibco, Thermo Fisher Scientific) at passage 28 were seeded as single cells at $0.094 \times 10^6$ cells/cm$^2$ on MATRIGEL™, at a 1:30 dilution, (Corning Incorporated, Corning, N.Y., Catalog #356231) coated dishes in a media of Dulbecco's Modified Eagle's Medium Nutrient mixture F-12 ("DMEM-F12") (Life Technologies Corporation, Carlsbad, Calif., Catalog No. 11330-032), with the following:

| | |
|---|---|
| GlutaMAX ™ | 1:100 dilution |
| (Life Technologies Corporation, Carlsbad, California, Catalog No. 35050-079) | ("1X concentration") |
| Ascorbic acid | 0.25 mM |
| (Sigma Aldrich Co. LLC, St. Louis, Missouri, Catalog No. A4544) | |
| FGF2 | 100 ng/ml |
| (R & D Systems Inc., Minneapolis, Minnesota, Catalog No. 233-FB-025) | |
| Transforming Growth Factor beta ("TGFβ") | 1 ng/ml |
| (R & D Systems Inc., Minneapolis, Minnesota, Catalog No. 240-B-002) | |
| insulin-transferrin-selenium-ethanolamine ("ITS-X") | 1:200 dilution |
| (Life Technologies, Carlsbad, California, Catalog No. 51500056) at a 1:100 dilution | |
| FAF-BSA | 2% |
| (Proliant, Inc., Boone, Idaho, Catalog No. 68700) | |
| Insulin-like Growth Factor-1 ("IGF-1") | 20 ng/ml |
| (R & D Systems Inc., Minneapolis, Minnesota, Catalog No. 291-G1-200) | |
| Rock Inhibitor Y-27632 ("Y-compound") | 10 μM |
| (Sigma Aldrich Co. LLC, St. Louis, Missouri, Catalog No. Y-0503) | |

About forty-eight hours post-seeding, the cultures were washed in incomplete PBS (phosphate buffered saline without magnesium or calcium) (Life Technologies, Carlsbad, Calif., Catalog No. 14190). Rock Inhibitor Y-27632 (Y compound) was used only for the first 24 hours of culture.

Differentiation: The cultures were differentiated using the following protocol. During Stages 1 through 3 of the protocol, cultures were maintained on planar adherent cultures. Others, however, have described differentiation using suspension culture including US US2014/0242693, which is incorporated by reference in its entirety; the protocol described herein can be modified and performed in suspension, which provides for scalability of manufacturing. The following nomenclature, S#D#, specifies exact time during Stages 1 through 3. For example, S1D3 is stage 1 day 3. Briefly, each stage defines differentiation towards definitive endoderm (stage 1), primitive gut tube (stage 2), and intestinal midgut endoderm (stage 3).

a. Stage 1 (3 days): Cells were cultured for one day in the following Stage 1 media:

| | |
|---|---|
| MCDB-131 medium (Life Technologies, Carlsbad, California, Catalog No. ME120219L2) | |
| Sodium bicarbonate (Sigma-Aldrich Co. LLC, St. Louis, Missouri, Catalog No. 5761) | 2.7 g/1000 ml |
| FAF-BSA | 0.5% |
| GlutaMAX ™ | 1:100 dilution ("1X concentration") |
| D-Glucose (Sigma-Aldrich Co. LLC, St. Louis, Missouri, Catalog No. G8769) | 4.5 mM to obtain a concentration of 10 mM D-Glucose |
| GDF8 (Peprotech, Rocky Hill, New Jersey, Catalog No. 120-00) | 100 ng/ml |
| 14-Prop-2-en-1-yl-3,5,7,14,17,23,27-heptaazatetracyclo [19.3.1.1~2,6~.1~8,12~]heptacosa-1(25),2(27),3,5,8(26),9,11,21,23-nonaen-16-one ("MCX compound"). | 1.5 μM |

Cells were then cultured for an additional day in the following media:

| | |
|---|---|
| MCDB-131 medium | |
| Sodium bicarbonate | 2.7 g/1000 ml |
| FAF-BSA | 0.5% |
| GlutaMAX ™ | 1X concentration |
| D-Glucose | 4.5 mM to obtain a concentration of 10 mM D-Glucose |
| GDF8 | 100 ng/ml |
| MCX compound | 0.1 μM |

Cells were then cultured for an additional day in the same media as day 2 above but without MCX compound.

b. Stage 2 (2 days): Cells were treated for two days with the following medium:

| | |
|---|---|
| MCDB-131 medium | |
| Sodium bicarbonate | 2.7 g/1000 ml |
| FAF-BSA | 0.5% |
| GlutaMAX ™ | 1X concentration |
| D-Glucose | 4.5 mM to obtain a concentration of 10 mM D-Glucose |
| Ascorbic Acid | 0.25 mM |
| FGF7 (R&D Systems, Inc., Minneapolis, Minnesota, Catalog No. 251-K | 50 ng/ml | c. Stage 3 (5 days): Cells were treated for five day with BLAR 001 custom medium:

| | |
|---|---|
| BLAR medium (custom manufactured by Life Technologies, Corporation, Carlsbad, California, Catalog No. ME120123L2, components listed on Table I) | |
| FAF-BSA | 0.5% |
| GlutaMAX ™ | 1X concentration |
| D-Glucose | 4.5 mM to obtain a concentration of 10 mM D-Glucose |
| Retinoic Acid (Sigma Aldrich, St. Louis, Missouri, Catalog No. R2625) | 1 μM |
| BMP4 compound (R&D Systems, Inc., Minneapolis, Minnesota, Catalog No. 314-BP OR BMP2 compound (R&D Systems, Inc., Minneapolis, Minnesota, Catalog No. 355-BM), | 50 ng/ml |

Either BMP4 or BMP2 can be used during Stage 3 in this method to achieve intestinal midgut endoderm cells in monolayer with CDX2 and FOXA2 protein co-presence, as illustrated in FIGS. 1A-4B (BMP4-based), and FIGS. 5A-7 (BMP2-based).

TABLE I

List of components of BLAR medium.

| Amino Acids | Concentration (mM) |
|---|---|
| Glycine | 3.00E−02 |
| Alanine | 3.00E−02 |
| Arginine | 3.00E−01 |
| Aspargine | 1.00E−01 |
| Aspartic Acid | 1.00E−01 |
| Cysteine | 1.99E−01 |
| Glutamic acid | 3.00E−02 |
| Histidine | 1.10E−01 |
| Isoleucine | 1.00E−02 |
| Leucine | 9.00E−02 |
| Lysine hydrochloride | 1.50E−01 |
| Methiane | 3.00E−02 |
| Phenylalanine | 3.00E−02 |
| Proline | 1.00E−01 |
| Serine | 1.00E−01 |
| Theronine | 3.00E−02 |
| Tryptophan | 2.00E−03 |
| Tyrosine disodium | 1.00E−02 |
| Valine | 3.00E−02 |
| Vitamins | |
| Biotin | 3.00E−05 |
| Choline chloride | 5.00E−03 |
| D-Calcium pantothenate | 1.50E−03 |
| Folinic Acid Calcium salt | 2.30E−03 |
| Niacinamide | 4.90E−03 |
| Pyridoxine hydrochloride | 9.70E−04 |
| Riboflavin | 1.00E−05 |
| Thiamine hydrochloride | 3.00E−03 |
| Vitamin B12 | 3.70E−06 |
| i-Inositol | 2.80E−03 |
| Salts/Minerals | |
| Calcium Chloride (CaCl$_2$—2H$_2$O) | 3.00E−01 |
| Cupric sulfate (CuSO$_4$—5H$_2$O) | 4.80E−06 |
| Ferric sulfate (FeSO$_4$—7H$_2$O) | 1.00E−03 |
| Magnesium Sulfate (MgSO$_4$—7H$_2$O) | 4.10E−01 |
| Potassium Chloride (KCl) | 3.80E+00 |
| Sodium Bicarbonate (NaHCO$_3$) | 1.40E+01 |
| Sodium Chloride (NaCl) | 1.10E+02 |

TABLE I-continued

List of components of BLAR medium.

| Amino Acids | Concentration (mM) |
|---|---|
| Sodium Phosphate dibasic ($Na_2HPO_4$—$7H_2O$) | 5.00E−01 |
| Zinc Sulfate ($ZnSO4$—$H2O$) | 1.00E−04 |
| Other | |
| Adenine | 1.00E−03 |
| D-Glucose (Dextrose) | 5.00E+00 |
| Lipoic Acid | 1.20E−05 |
| Phenol Red | 1.00E−02 |
| Sodium Pyruvate | 1.00E+00 |
| Thymidine | 9.80E−05 |

Quantification of differentiated cells: For quantification of protein presence co-localization, S3D5 cells were harvested and analyzed by FACS. FACS staining was conducted as described in *Nature Biotechnology*, 2014 (32) 11, 1121-1133, incorporated herein by reference in its entirety, and using the antibodies listed in Table II. In brief, differentiated cells were incubated in TrypLE™ Express (Life Technologies, Carlsbad, Calif., Catalog No. 12604) for 5-10 minutes at 37° C., released into a single-cell suspension, after which they were washed twice with a staining buffer of PBS containing 0.2% BSA (BD Biosciences, San Jose, Calif., Catalog No. 554657). Intracellular antibody staining was accomplished by utilizing the LIVE/DEAD Violet Fluorescent reactive dye (Life Technologies, Carlsbad, Calif., Catalog No. L34955) at 4° C. for 30 minutes followed by a single wash in cold PBS. Fixing of cells was in 300 μl of Cytofix/Cytoperm Buffer (BD Biosciences, San Jose, Calif., Catalog No. 554723) followed by two washes in Perm/Wash Buffer (BD Biosciences, San Jose, Calif., Catalog No. 554722). Cells were then incubated with the appropriate antibodies at 4° C. for 30 minutes (for unconjugated antibodies) or 1 hour (for conjugated antibodies), and then washed twice prior to analysis on the BD FACS Canto II using BD FACS Diva Software with at least 30,000 events being acquired. Non-viable cells were excluded during FACS analysis, and gating was determined by using isotype antibodies ("IgG"). IgG FACS data is shown as the top panel for each FACS experiment presented. Antibodies were tested for specificity using positive controls, such as Caco-2 cells, or negative controls, such as S1D3 definitive endoderm ("DE") cells.

TABLE II

List of antibodies used for FACS analysis.

| Antigen | Species | Source/Catalog Number | Dilution |
|---|---|---|---|
| PE IgG1, κ Isotype control | Mouse | BD Cat# 555749 | 1:5 |
| Alexa Fluor 647 IgG1, κ Isotype control | Mouse | BD Cat# 557732 | Neat |
| PE anti-Human FOXA2 | Mouse | BD Cat# 561589 | Neat |
| PE Anti-human CDX2 | Mouse | BD Cat# 563428 | Neat |
| Alexa Fluor 647 anti-CDX2 | Mouse | BD Cat# 560395 | Neat |
| Alexa Fluor 647 anti-KI67 | Mouse | BD Cat# 561126 | Neat |
| PE anti-PDX1 | Mouse | BD Cat# 562161 | Neat |
| PE anti-SOX2 | Mouse | BD Cat# 560291 | Neat |
| Anti-Mouse IgG(H + L) Secondary Antibody, Alexa Fluor 647 conjugate | Goat | Life technology Cat# A21235 | 1:4000 |
| F(ab')2 anti-rabbit IgG(H + L) Secondary | Goat | Life technology Cat# A10542 | Neat |

TABLE II-continued

List of antibodies used for FACS analysis.

| Antigen | Species | Source/Catalog Number | Dilution |
|---|---|---|---|
| Antibody, RPE conjugate | | | |
| Anti-SOX9 | Rabbit | Millipore Cat# AB5535 | 1:10 |
| Anti-CDX2 [CDX2-88] | Mouse | BioGenex Cat# MU392A-UC | 1:10 |

For quantification of protein co-localization at various stages, Caco-2, S2D2, S3D2 and S3D5 cells were harvested as a monolayer and analyzed by immunofluorescence ("IF"). Note that the morphology seen in IF images was caused by the method of cell scraping from the monolayer of adherent cultures. H1-hESC-derived cells were prepared and stained as described in *Nature Biotechnology*, 2014 (32) 11, 1121-1133, and using the antibodies listed in Table III. For cryosectioning, cells were rinsed with PBS followed by overnight fixation in 4% PFA (Sigma Aldrich, St. Louis, Mo., Catalog No. 158127) at 4° C. Following fixation, 4% PFA was removed, cells rinsed twice with PBS, and incubated overnight at 4° C. in 30% sucrose solution (Amresco, Solon, Ohio, Catalog No. 0335). The samples were cryopreserved in OCT solution (Sakura Finetek USA Inc., Torrance, Calif., Catalog No. 4583), and 5 μm sections placed on Superfrost plus slides (VWR International, LLC, Radnor, Pa., Catalog No. 48311-703). For IF-staining, primary antibodies were added at appropriate dilutions overnight at 4° C., while secondary antibodies were added for 30 min at room temperature followed by rinsing with PBS and adding Vectastain mounting reagent with DAPI (Vector Laboratories Inc., Burlingame, Calif., Catalog No. H-1200). The sections were visualized using a Nikon Ti fluorescence microscope (Nikon Instruments, Inc., Melville, N.Y.).

TABLE III

List of antibodies used for IF analysis.

| Antigen | Species | Source | Dilution |
|---|---|---|---|
| CDX2 | Mouse | BioGenex (Catalog No. MU392A-UC) | 1:50 |
| FOXA2 | Rabbit | Seven Hills (Catalog No. WRAB 1200) | 1:500 |
| SOX9 | Rabbit | Millipore EMD (Catalog No. AB5535) | 1:100 |
| PDX1 | Goat | R&D Systems (Catalog No. AF2419) | 1:33 |
| SOX2 | Goat | Sigma (Catalog No. sc-17320) | 1:50 |
| KLF5 | Rabbit | Abcam (Catalog No. ab24331) | 1:150 (Tyramide amplification - Perkin Elmer, Waltham, MA, NEL744001KT) |
| ALB | Rabbit | Sigma (Catalog No. A0433) | 1:250 |
| KI67 | Rabbit | Abcam (Catalog No. ab16667) | 1:100 |
| Donkey anti-mouse IgG (H + L) Secondary | Mouse | Life Technologies | 1:100 |

TABLE III-continued

List of antibodies used for IF analysis.

| Antigen | Species | Source | Dilution |
|---|---|---|---|
| antibody, Alexa Fluor 488 | | (Catalog No. A21202) | |
| Donkey anti-rabbit IgG (H + L) Secondary Antibody, Alexa Fluor 546 | Rabbit | Life Technologies (Catalog No. A10040) | 1:200 |
| Donkey anti-goat IgG (H + L) Secondary Antibody, Alexa Fluor 546 | Goat | Life Technologies (Catalog No. A11056) | 1:50-1:100 |
| Goat anti-rabbit IgG, HRP-Labeled | Rabbit | Perkin Elmer, Waltham, MA (Catalog No. NEF812001) | 1:250 |

For quantification of gene expression at various stages, Caco-2, H1-hESC, S1D3, S2D2, S3D2 and S3D5 cells were harvested, as described in *Nature Biotechnology*, 2014 (32) 11, 1121-1133. Briefly, gene expression was assessed in cells using custom Taqman® Arrays (Applied Biosystems, Foster City, Calif.); Open Array® (OA) was used for CDX2, FOXA2, SOX2, SOX9, PDX1, ALB, PTF1A, and Taqman® Low Density Array (TLDA) was used for KLF5, HOXC5, and LGR5, with housekeeping gene GAPDH used for both tests. Data were analyzed using Sequence Detection Software (Applied Biosystems, Foster City, Calif.), and normalized using GAPDH as a housekeeping gene to undifferentiated H1-hESC using the ΔΔCt method. Primer details are outlined in Table IV.

TABLE IV

List of RT-qPCR primers.

| | Gene | Assay ID |
|---|---|---|
| 1 | ALB | Hs00609411_m1 |
| 2 | CDX2 | Hs00230919_m1 |
| 3 | FOXA2 | Hs00232764_m1 |
| 4 | GAPDH | Hs99999905_m1 |
| 5 | PDX1 | Hs00236830_m1 |
| 6 | PTF1A | Hs00603586_g1 |
| 7 | SOX2 | Hs01053049_s1 |
| 8 | SOX9 | Hs00165814_m1 |
| 9 | HOXC5 | Hs00232747_m1 |
| 10 | KLF5 | Hs00156145_m1 |
| 11 | LGR5 | Hs00969422_m1 |
| 12 | HOXA13 | Hs00426284_ml |
| 13 | HAND1 | Hs00231848_ml |

Results

A summary of a differentiation method, including the important medium components, growth factors and small molecules that were added to each stage, and key stage-specific markers of the differentiating intestinal midgut endoderm cells (FOXA2; CDX2; KLF5; SOX9; PDX1$^{LO}$) is depicted in FIG. 1A. As compared to the neutral pH noted for S2D2 (7.35±0.04), cells were exposed to slightly acidic conditions in the BLAR medium, during the entirety of stage 3 (pH; S3D1, 6.98±0.05; S3D2, 7.02±0.04; S3D5, 7.18±0.03) (FIG. 1B), and as a result of lower sodium bicarbonate levels in BLAR medium. The pH of the culture can range from about 6.8 to 7.2 during the five days of stage 3. FIG. 1C depicts representative phase-contrast images of a S3D5 monolayer (left), and human epithelial colon adenocarcinoma cell line ("Caco-2") (right), which was used as a benchmark for characterization of differentiation. A uniform morphology at S3D5 was observed. Characterization of cell number using the Nucleocounter® NC-100 (Chemometec, Alleroed, Denmark, Catalog No. 900-004) shows that one hESC differentiated into 4.56±2.60 S3D5 hindgut endoderm cells (FIG. 1D).

Figure 2C:
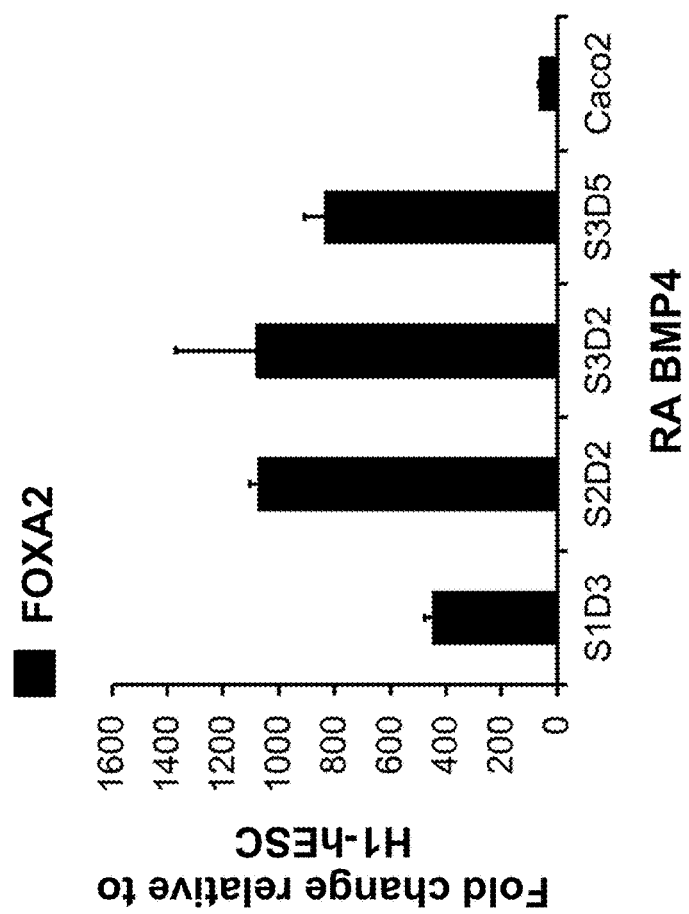
Figure 2D:
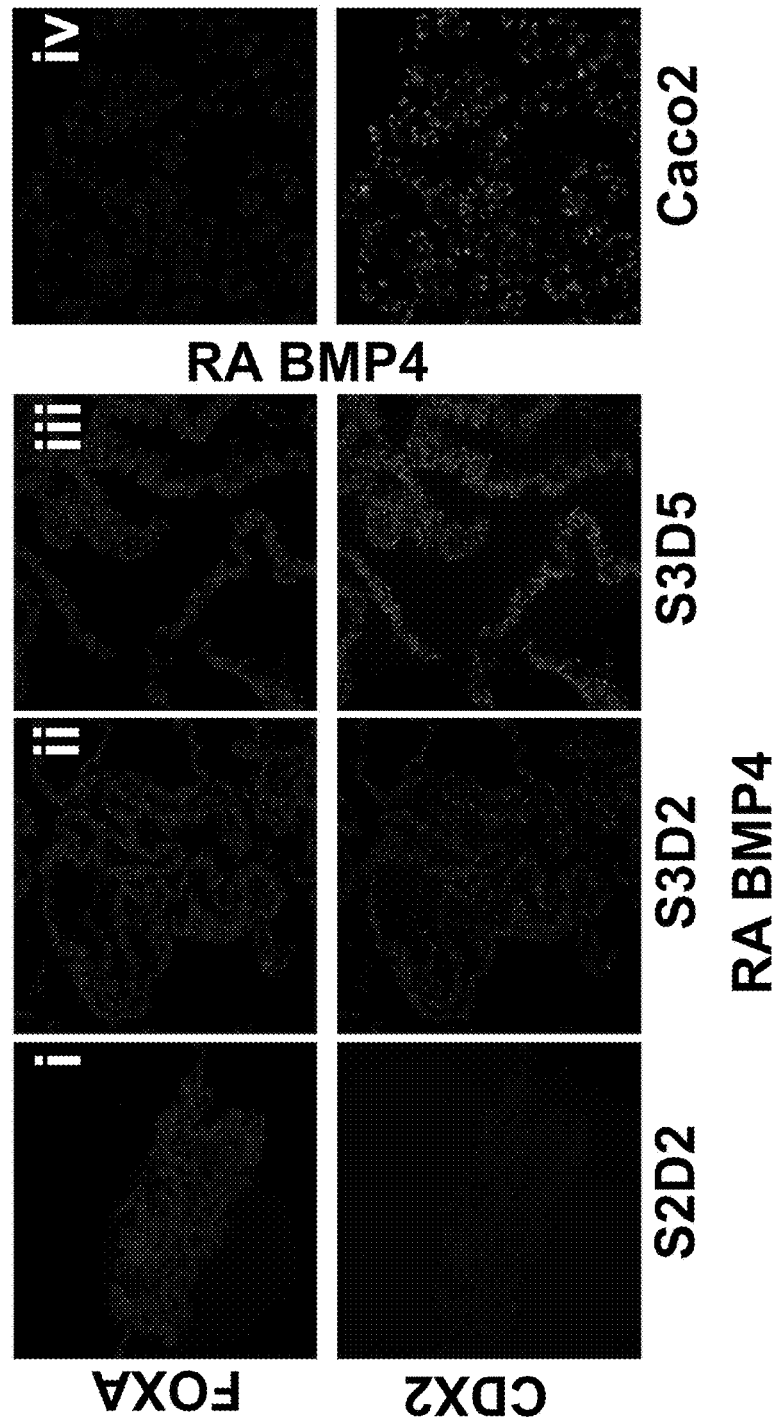

The differentiation method, utilizing BMP4, efficiently generates and maintains intestinal midgut endoderm cells in monolayer, each comprising both CDX2 and FOXA2 on transcript and protein levels. FIG. 2A (bottom) shows that 90.0±5.85 percent of S3D5 cells were co-present for both CDX2 and FOXA2 protein, similar to percentage observed in Caco-2 cells (86.0±6.67). Conversely, definitive endoderm (DE-S1D3) cells were devoid of CDX2 and FOXA2 co-presence (2.3±1.2). Gene expression analysis shows CDX2 induced (FIG. 2B), and FOXA2 maintained (FIG. 2C) during Stage 3. FIG. 2D shows that the induction of CDX2 protein levels and CDX2/FOXA2 protein co-presence after the establishment of the FOXA2-positive primitive gut endoderm stage, S2D2 (FIG. 2D-i), progressively increased through S3D2 (FIG. 2D-ii), and at S3D5 (FIG. 2D-iii) reached similar levels as seen in Caco-2 cells (FIG. 2D-iv). CDX2 protein is depicted on the bottom row, and FOXA2 protein is depicted on the top row.

Transcript and protein levels of additional TFs are found at S3D5, which constitute robust intestinal midgut endoderm induction. FIGS. 3A-3P show that proper intestinal midgut endoderm was achieved. In addition to CDX2 and FOXA2 co-presence, S3D5 cells also exhibited co-presence of SOX9, PDX1, KLF5, HOXC5, but did not express SOX2, ALB, PTF1A, and LGR5. The protein presence of all TFs is depicted in separate single channel images. FIG. 3A (bottom) shows that 98.7±0.25 percent of cells were co-present for both CDX2 and SOX9 at S3D5. Strong induction of SOX9 gene expression was comparable to levels observed in Caco-2 cells (FIG. 3B), and protein presence as assessed by IF-analysis were observed (FIG. 3C). 69.4±14.2 percent of cells were co-positive for both CDX2 and PDX1 (FIG. 3D—bottom). PDX1 gene expression was induced at low levels, as compared to pancreas-biased S4D3 cells (See, e.g., US2014/0242693) (FIG. 3E), and this was reflected low to absent protein levels in the IF-analysis (FIG. 3F).

Figure 3L:
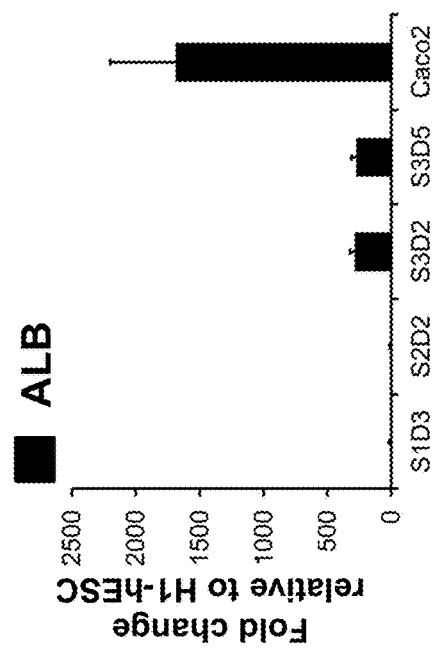
FIGS. 3A-3Q demonstrate the induction by S3D5 of transcript and protein levels of additional transcription factors (TF) that constitute robust intestinal midgut endoderm induction; proper intestinal midgut endoderm was achieved. In addition to CDX2 and FOXA2 co-expression, S3D5 cells also exhibited co-expression of SOX9, PDX1, KLF5, HOXC5 (homeobox C5), but not SOX2 (SRY-box 2), ALB (albumin), PTF1A (pancreas specific transcription factor, 1a), and LGR5(leucine rich repeat containing G protein coupled receptor 5). The protein presence of all TFs is depicted in separate single channel images.
FIG. 3I), and gene expression was below levels seen in hESC and Caco-2 cells (FIG. 3H). The gene expression of KLF5, essential for proper development of intestinal mid-/hindgut endoderm, was upregulated at S3D5 (FIG. 3J). Protein co-presence of KLF5within CDX2-positive cells at S3D5 was observed (FIG. 3K). ALB gene expression (FIG. 3L), and protein presence (FIG. 3M) was not observed in S3D5 cells. The gene expression of pancreas lineage allocating TF, PTF1A, was not induced in S3D5 cells, unlike pancreas-biased S4D3 cells (FIG. 3N). The homeobox gene, HOXC5, present in the embryonic midgut endoderm was induced in S3D5 cells (FIG. 3O).
FIG. 3P demonstrates that LGR5, a marker of embryonic intestinal endoderm beginning at mid-gestation in the mouse, was not induced in S3D5 cells.
Figure 3M:
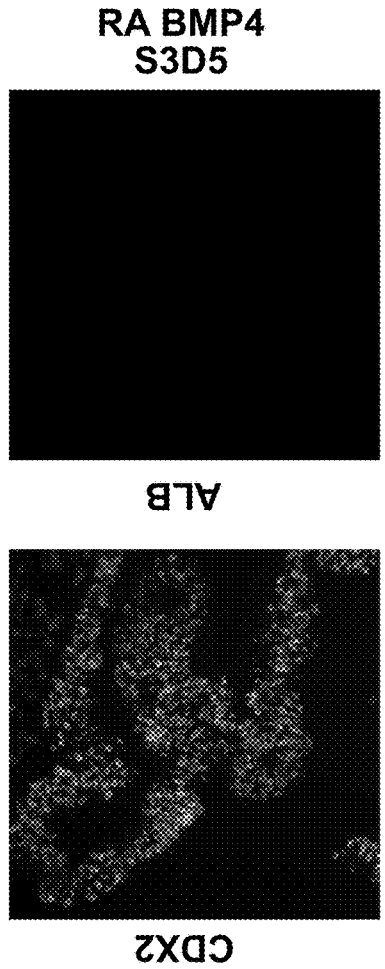
Figure 3N:
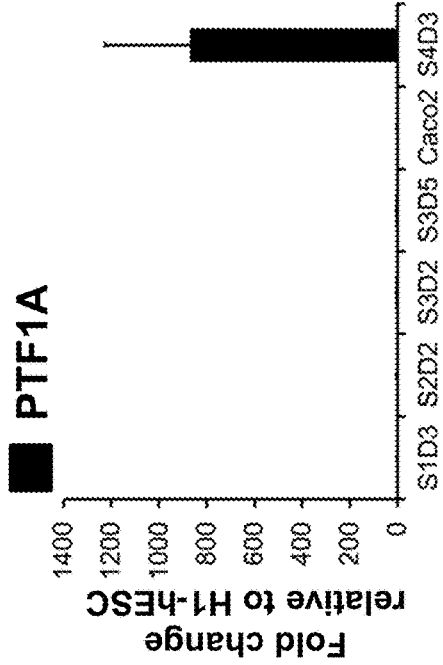
Figure 3O:
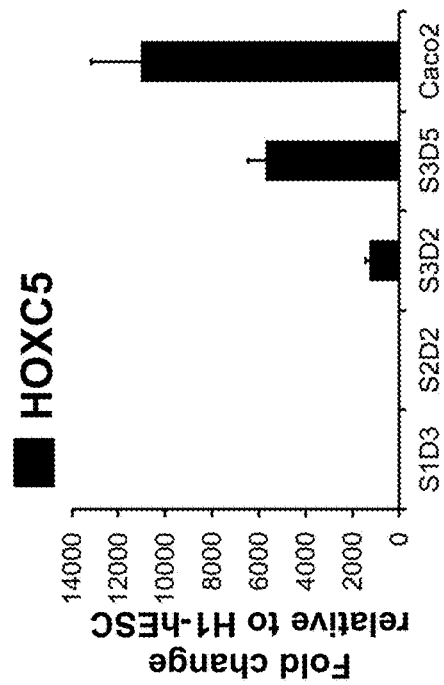

S3D5 cells did not express the anterior endoderm TF SOX2, and only 1.45±0.15 of S3D5 cells exhibited SOX2 and CDX2 co-presence (FIG. 3G—bottom; 3I), and gene expression was below levels seen in hESC and Caco-2 cells (FIG. 3H). Gene expression of KLF5, essential for proper development of hindgut endoderm, was upregulated at S3D5 (FIG. 3J). Protein co-presence of KLF5 within CDX2-positive cells at S3D5 was observed (FIG. 3K). ALB gene expression (FIG. 3L), and protein presence (FIG. 3M) was not observed in S3D5 cells. Similarly, the gene expression of PTF1A, a pancreas lineage marker, was not induced in S3D5 cells, as compared to pancreas-biased S4D3 cells (FIG. 3N). The homeobox gene, HOXC5, present in the embryonic intestinal midgut endoderm was strongly induced in S3D5 cells (FIG. 3O). FIG. 3P shows that LGR5, a marker of embryonic intestinal endoderm beginning at mid-gestation in the mouse, was not induced in S3D5 cells (FIG. 3P). FIG. 3Q shows that HOXA13, a marker of the intestinal hindgut endoderm, was not induced in S3D5 cells (FIG. 3P).

Figure 4A:
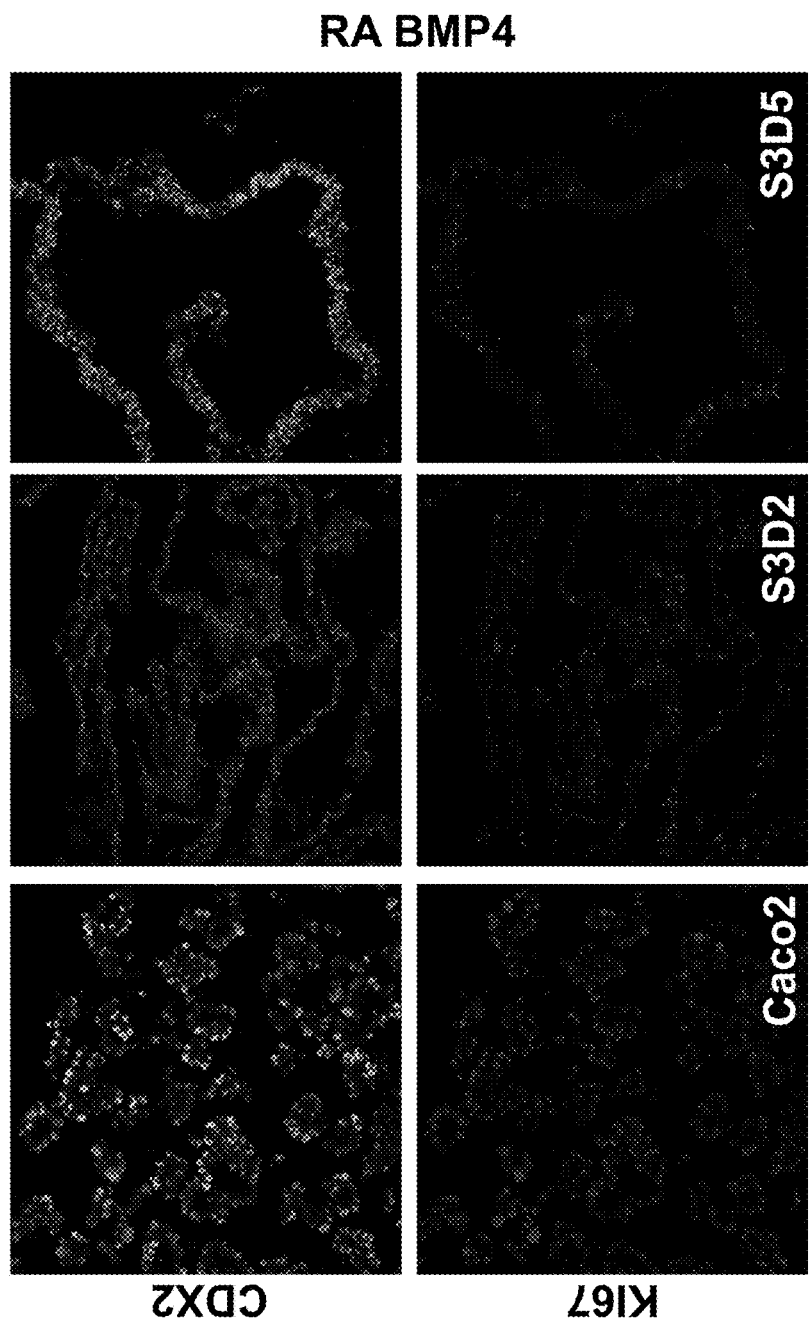

FIGS. 4A-4B illustrate the proliferative profile of differentiating S3D5 cells. FIG. 4A depicts Caco-2 cells, where most of CDX2-protein positive cells were in active cell cycle (as indicated by the co-expression with KI67 protein) (left), and the proliferative index of the H1-hESC-derived cells during Stage 3 that decreased over time (S3D2—middle; S3D5—right). CDX2 (top row) and KI67 (bottom row) protein levels are depicted as single channel images. The percentage KI67-protein positive cells of total S3D5 cells (total cells are >90% CDX2-positive), assessed by FACS, was 16.8±3.12, in contrast with percentage seen at S1D3 (97.3±1.3), and in Caco-2 cells (99.2±0.2) (FIG. 4B).

Figure 5C:
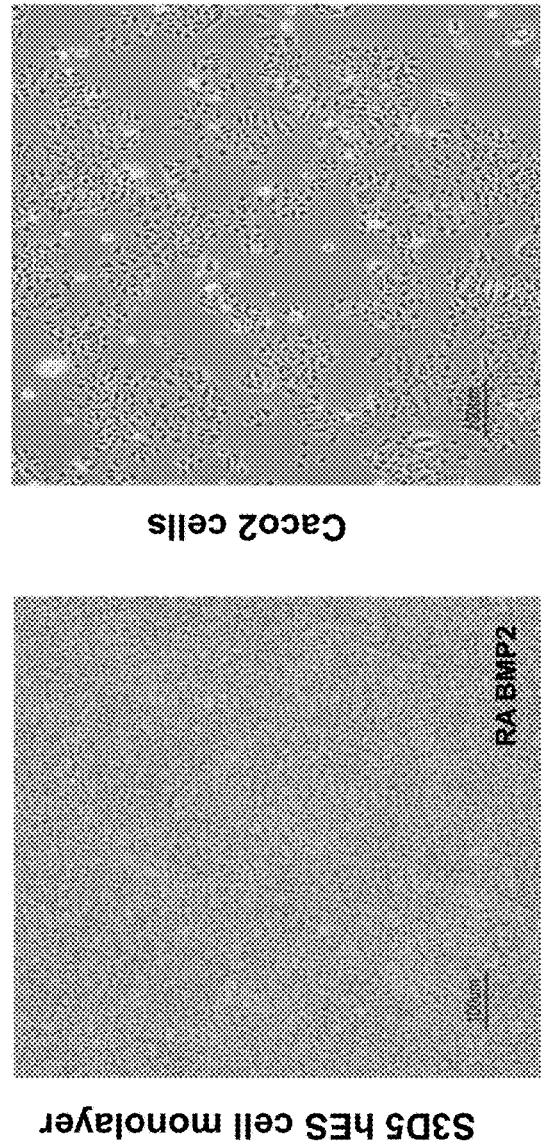

BMP2 can be used as an alternative to BMP4, during Stage 3 in this method to produce a monolayer of intestinal midgut endoderm cells with CDX2 and FOXA2 protein co-presence. FIG. 5A depicts a summary of a differentiation method, including the medium components, growth factors and small molecules that were added to each stage, and key stage-specific markers of the differentiating intestinal midgut endoderm cells (FOXA2, CDX2, KLF5, SOX9, and PDX1$^{LO}$). Compared to the neutral pH noted at S2D2 (7.35±0.04), cells were exposed to slightly acidic conditions in BLAR medium, during the entirety of stage 3 (pH; S3D1, 6.92; S3D2, 7.01; S3D5, 7.22) (FIG. 5B), and as a result of lower sodium bicarbonate levels in BLAR acidic medium. FIG. 5C depicts representative phase-contrast images of a S3D5 monolayer (left), and Caco-2 cells (right). A uniform morphology at S3D5 was observed.

Figure 6C:
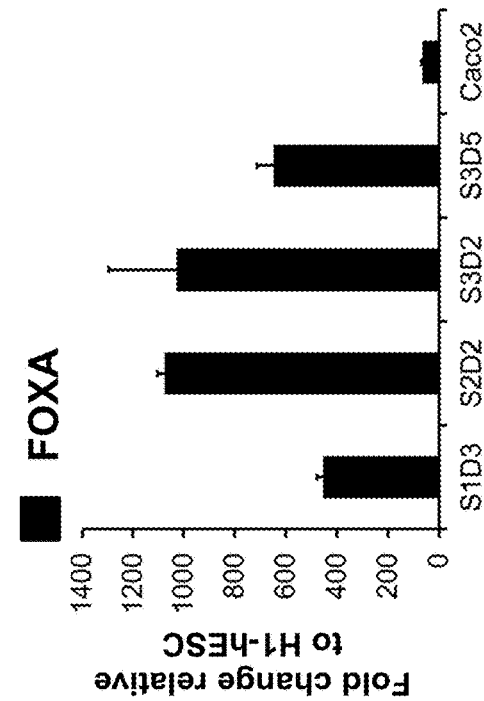
FIGS. 6A-6U demonstrate generation of proper intestinal midgut endoderm cells in monolayer, each comprising of CDX2, FOXA2, KLF5, SOX9, PDX1$^{LO}$ and HOXC5 on transcript and protein levels. For IF-images, all TF protein levels are depicted as single channel images.
FIG. 6D shows CDX2 protein levels and complete CDX2/FOXA2 protein co-presence induced at S3D5, reaching similar levels as seen in Caco-2 cells (FIG. 2D-iv).
FIG. 6E (bottom) demonstrates that 99.8 percent of cells were co-present for both CDX2 and SOX9 at S3D5. Strong induction of SOX9 gene expression to levels seen in Caco-2 cells (FIG. 6F), and protein presence as assessed by IF-analysis were observed (FIG. 6G). 45.5 percent of cells were co-positive for both CDX2 and PDX1 (FIG. 6H—bottom). PDX1 gene expression was induced at low levels compared to pancreas-biased S4D3 cells (FIG. 6I; low to absent protein levels was reflected in the IF-analysis (FIG. 6J). Anterior endoderm TF SOX2 was not observed in S3D5 cells, as 0.8 percent of S3D5 cells exhibited SOX2 and CDX2 co-presence (FIG. 6K—bottom.
FIG. 6M), and gene expression was below levels seen in hESC and Caco-2 cells (FIG. 6L). Gene expression of KLF5, essential for proper development of intestinal mid-/hindgut endoderm, was upregulated at S3D5 (FIG. 6N). Protein co-presence of KLF5within CDX2-positive cells was observed at S3D5 (FIG. 6O). ALB gene expression (FIG. 6P), and protein presence (FIG. 6Q) was not observed in S3D5 cells. Gene expression of pancreas lineage allocating TF, PTF1A, was not induced in S3D5 cells, unlike pancreas-biased S4D3 cells (FIG. 6R). The homeobox gene HOXC5, present in the embryonic intestinal midgut endoderm, was induced in S3D5 cells (FIG. 6S).
FIG. 6T demonstrates that LGR5, a marker of embryonic intestinal endoderm beginning at mid-gestation, was not induced in S3D5 cells.
Figure 6B:
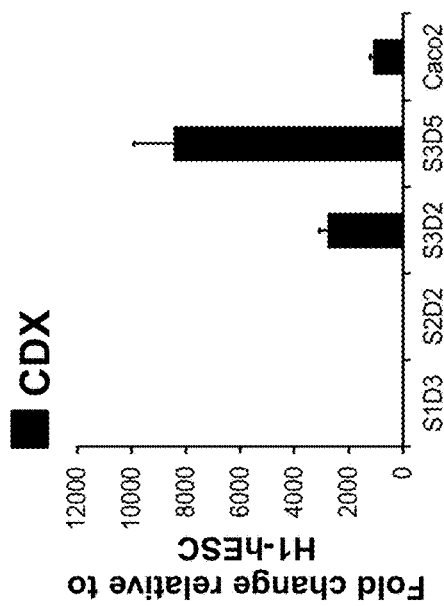
Figure 6P:
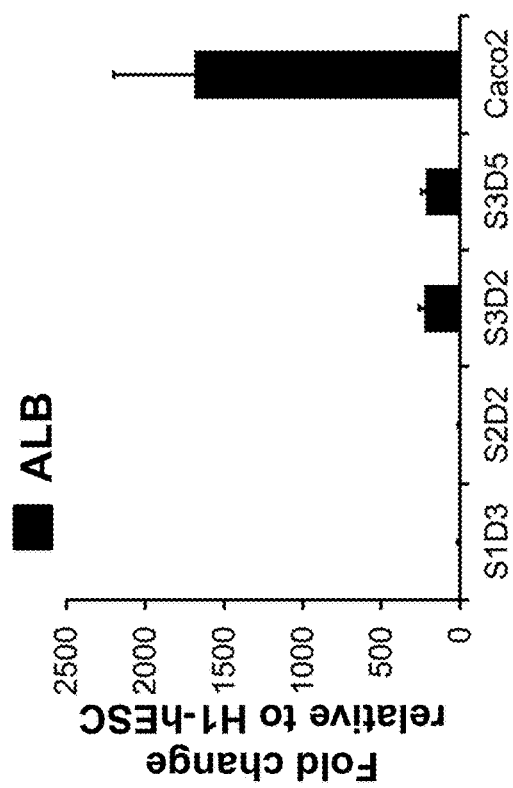
Figure 6Q:
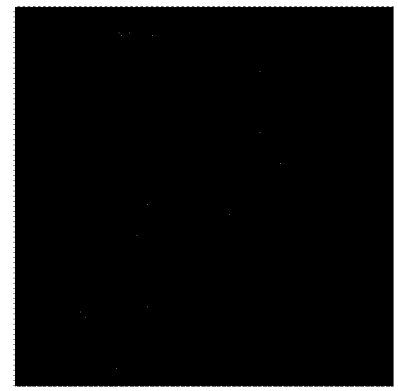
Figure 6R:
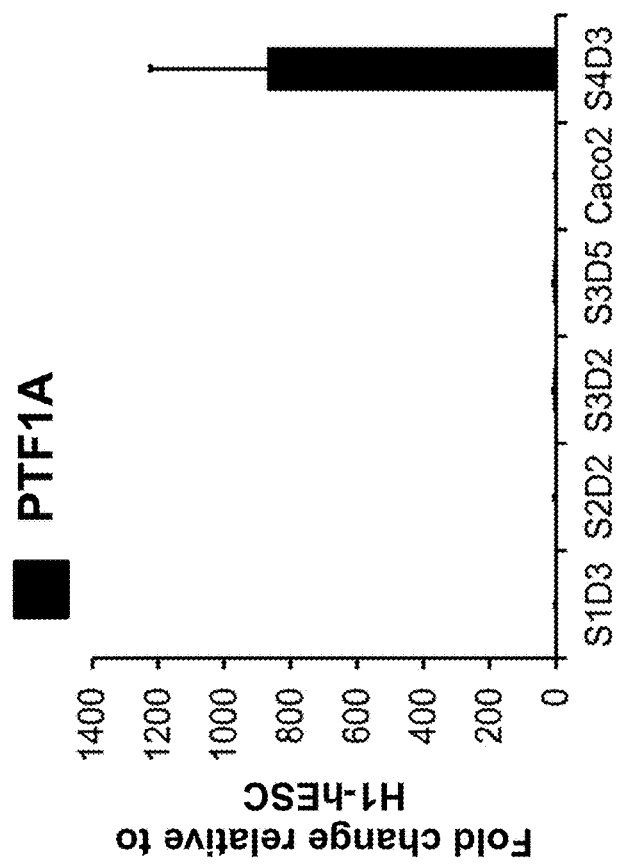
Figure 6T:
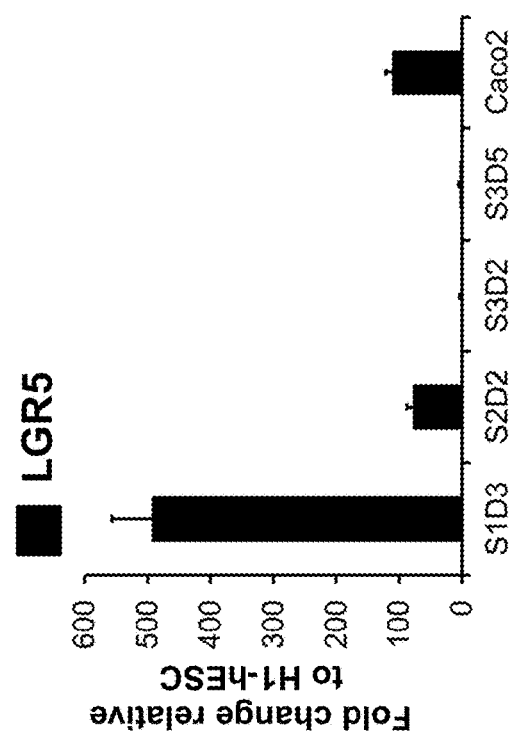

The differentiation method generates and maintains proper intestinal midgut endoderm cells in monolayer, each comprising of CDX2, FOXA2, KLF5, SOX9, PDX1$^{LO}$ and HOXC5 on transcript and protein levels. All TF protein levels are depicted as single channel IF images. FIG. 6A (bottom) shows that 94 percent of S3D5 cells were co-present for both CDX2 and FOXA2 protein, similar to percentage seen in Caco-2 cells (86.0±6.67). Gene expression analysis shows that CDX2 was induced (FIG. 6B), and FOXA2 maintained (FIG. 6C) during Stage 3. FIG. 6D shows that CDX2 protein levels and complete CDX2/FOXA2 protein co-presence were induced at S3D5 (FIG. 6D), which is comparable to levels observed in Caco-2 cells (FIG. 2D-iv). FIG. 6E (bottom) shows that 99.8 percent of cells were co-present for both CDX2 and SOX9 at S3D5. Strong induction of SOX9 gene expression was observed similar to levels in Caco-2 cells (FIG. 6F), and protein presence as assessed by IF-analysis was observed (FIG. 6G). 45.5 percent of cells were co-positive for both CDX2 and PDX1 (FIG. 6H—bottom). PDX1 gene expression was induced at low levels, when compared to pancreas-biased S4D3 cells (FIG. 6I), and low to absent protein levels was reflected in the IF-analysis (FIG. 6J). Anterior endoderm TF SOX2 was not observed in S3D5 cells, as 0.8 percent of S3D5 cells exhibited SOX2 and CDX2 co-presence (FIG. 6K—bottom; 6M), and gene expression was below levels seen in hESC and Caco-2 cells (FIG. 6L). The gene expression of KLF5, an essential marker for demonstrating proper development of hindgut endoderm, was strongly upregulated at S3D5 (FIG. 6N). Protein co-presence of KLF5 within CDX2-positive cells at S3D5 was observed (FIG. 6O). ALB gene expression (FIG. 6P), and protein presence (FIG. 6Q) was not observed in S3D5 cells. The gene expression of pancreas lineage allocating TF, PTF1A, was not induced in S3D5 cells, as compared to pancreas-biased S4D3 cells (FIG. 6R). The homeobox gene HOXC5, present in the embryonic intestinal midgut endoderm, was strongly induced in S3D5 cells (FIG. 6S). FIG. 6T demonstrates that LGR5, a marker of embryonic intestinal endoderm beginning at mid-gestation, was not induced in S3D5 cells. FIG. 6U demonstrates that HOXA13, a marker of the intestinal hindgut endoderm, was not induced in S3D5 cells (FIG. 6U).

FIG. 7 characterizes the proliferative profile of differentiating S3D5 cells, showing Caco-2 cells, where most of CDX2-protein positive cells were in active cell cycle (as indicated by the co-expression with KI67 protein) (left), compared to the proliferative index of the H1-hESC-derived cells during Stage 3 that was lower (S3D5—right). CDX2 (top row) and KI67 (bottom row) protein levels are depicted as single channel images. The percentage KI67-protein positive cells of total S3D5 cells (total cells are >90% CDX2-positive), as assessed by FACS, was 14.1 percent, in contrast with percentage seen at S1D3 (97.3±1.3), compared to Caco-2 cells (99.2±0.2) (FIG. 7; 4B).

Example 2

Intestinal Culturing Starting From the Definitive Endoderm, and Using FGF4 and WNT-agonists, Generates an Endoderm-mesenchyme Mixture of CDX2+Mid-/hindgut Cells This example demonstrates the endoderm-mesenchyme-mixed quality of the CDX2+mid-/hindgut cells generated from intestinal culturing beginning at the definitive endoderm stage using FGF4 and WNT-agonists (Spence et al., Nature, 2011; 470:105-109; Watson et al. Nature Med, 2014; 11:1310-1314). To examine the induction to midgut/hindgut endoderm cells described in Spence et al., infra, hESCs were differentiated using the protocol below. Note that the differentiation conditions outlined in this Example differ from Example 1 by the following: (i) intestinal condition starting point begins at the definitive endoderm stage; (ii) different growth factors and small molecules are used than RA and BMP4 or BMP2; and (iii) acidic culture conditions are not used.

Materials and Methods

Cell culture: H1-hESC cells were cultured and maintained as described in Example 1.

Differentiation: The cultures were differentiated using the following protocol.

Stage 1-Mimic (3 days): Cells were cultured for one day in the following Stage 1 medium:

| | |
|---|---|
| RMPI 1640 medium | |
| (Thermo Fisher Scientific, Catalog No. 11875) | |
| Penicillin-Streptomycin | 1X concentration |
| (Thermo Fisher Scientific, Catalog No. 15140122) | (1:100 dilution from stock concentration) |
| L-Glutamine | 2 mM |
| (Thermo Fisher Scientific, Catalog No. 25030081) | |
| Activin A | 100 ng/ml |
| (R&D Systems, Inc., Minneapolis, Minnesota, Catalog No. 338-AC) | |

Cells were then cultured for an additional day in the following media:

| | |
|---|---|
| RMPI 1640 medium | |
| Penicillin-Streptomycin | 1X concentration |
| | (1:100 dilution from stock concentration) |
| L-Glutamine | 2 mM |
| Activin A | 100 ng/ml |
| Defined Fetal Bovine Serum (FBS) | 0.2% |
| (Hyclone, Catalog No. SH30070.02) | |

Cells were then cultured for an additional day in the following media:

| RMPI 1640 medium | |
|---|---|
| Penicillin-Streptomycin | 1X concentration |
| | (1:100 dilution from |
| | stock concentration) |
| L-Glutamine | 2 mM |
| Activin A | 100 ng/ml |
| Defined FBS | 2.0% |

Post-Stage 1 (2 days): For example, pS1d1 is post-Stage 1 day 1 and pS1d2 is post-Stage 1 day 2. Cells were cultured for two days in the following Post-Stage 1 medium:

| RMPI 1640 medium | |
|---|---|
| Penicillin-Streptomycin | 1X concentration |
| | (1:100 dilution from |
| | stock concentration) |
| L-Glutamine | 2 mM |
| FGF4 | 500 ng/ml |
| (R&D Systems, Inc., Minneapolis, Minnesota, | |
| Catalog No. 235-F4) | |
| Defined Fetal Bovine Serum (FBS) | 2.0% |
| WNT3A | 500 ng/ml |
| (R&D Systems, Inc., Minneapolis, Minnesota, | |
| Catalog No. 5036-WN) | |
| OR | |
| Chiron99201 | 3 µM |
| (Stemgent, Catalog No. 0400041) | |

Quantification: Phase contrast imaging and quantification of gene expression followed the procedures in Example 1.

Results

Figure 8A:
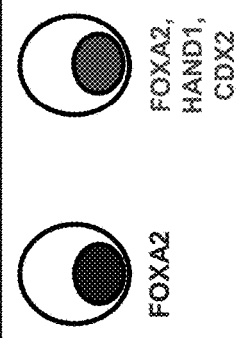
Figure 8B:
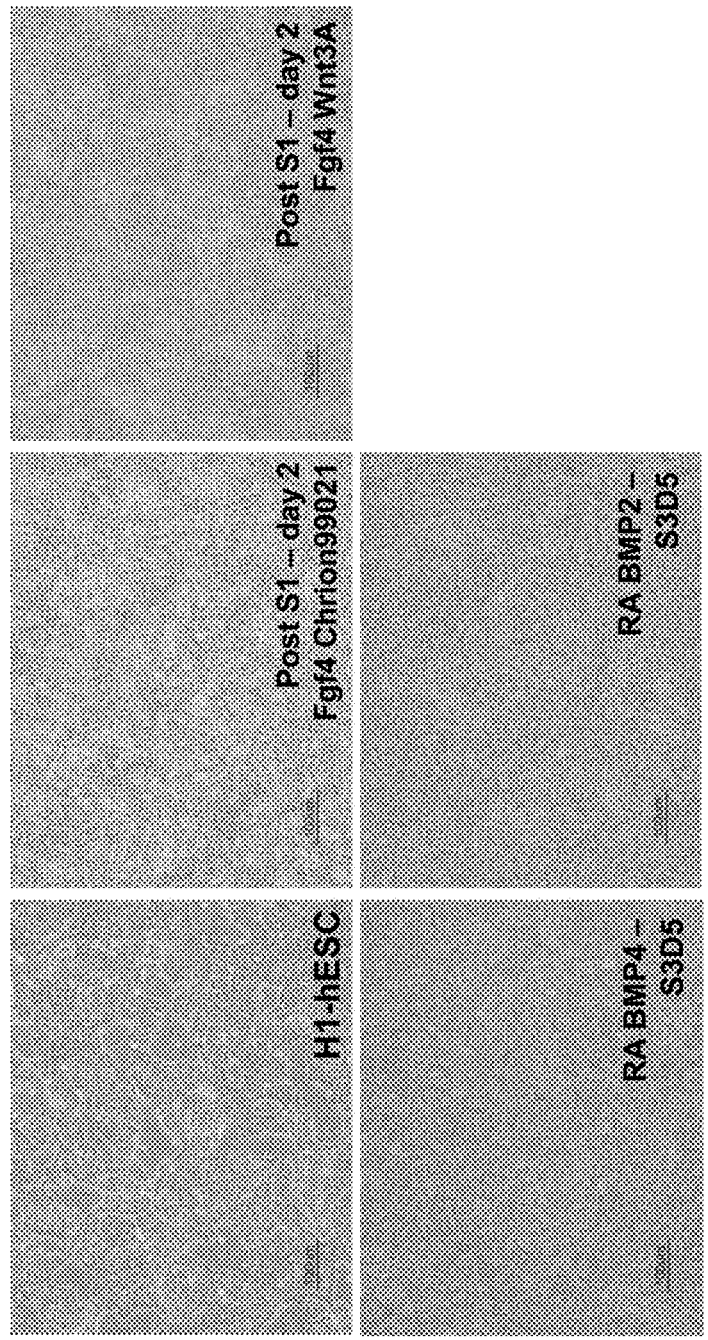

A summary of the differentiation methods, including medium components, growth factors and small molecules added to each stage, and signature or key stage-specific markers of the differentiating intestinal mid-/hindgut endoderm cells (HAND1) is depicted in FIG. 8A. Intestinal conditioning (post-Stage 1), started at the definitive endoderm stage, with 500 ng/ml FGF4, and either 3 µM Chiron99021 (Watson et al.), or 500 ng/ml Wnt3A (Spence et al.). The term "Stage 1-mimic" refers to the definitive endoderm differentiation protocol in this example that differs from the "S1D3-Original" that refers to Stage 1 conditioning described in Example 1. FIG. 8B shows phase-contrast images of H1-hESC cells (top row, left), post-Stage 1 cells conditioned two days with 500 ng/ml FGF4 and 3 µM Chiron99021 (top row, middle), post-Stage 1 cells conditioned two days with 500 ng/ml FGF4 and 500 ng/ml Wnt3A (top row, right), along with a S3D5 monolayer conditioned by RA/BMP4 (bottom row, left), and a S3D5 monolayer conditioned by RA/BMP2 (bottom row, right) (from Example 1).

Figure 8C:
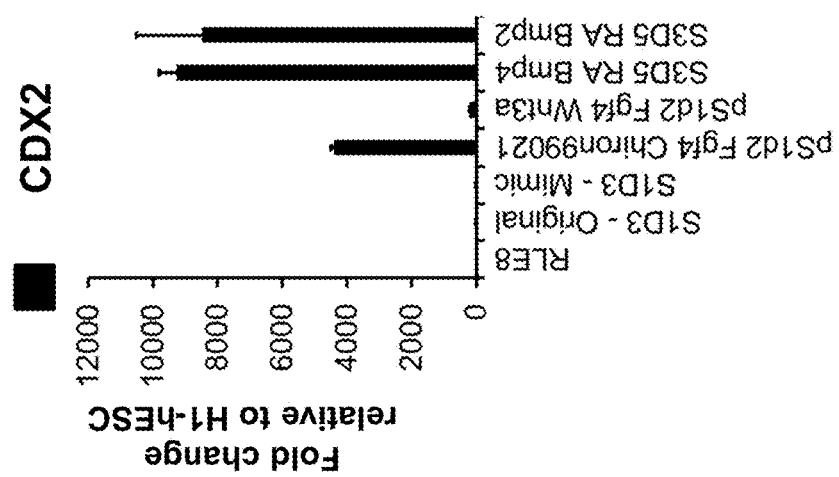
Figure 8E:
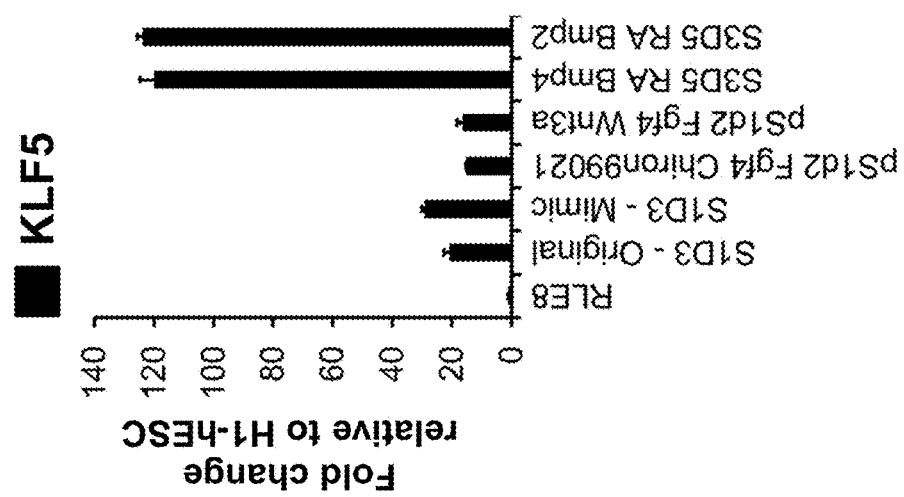

Induction of CDX2 gene expression was achieved after two days of conditioning, but at much lower levels compared to RA/BMP2 or RA/BMP4 S3D5 (FIG. 8C). However, the gene expression of the endoderm marker FOXA2 was maintained (FIG. 8D), and mesoderm/mesenchyme marker HAND1 was strongly induced (FIG. 8F). Also, KLF5 was not induced at the two day time point unlike by RA/BMP4 and RA/BMP2 conditioning (FIG. 8E). As conclusively shown in FIG. 8F, this gene expression pattern is reflective of the heterogeneous cell population seen in Watson et al. and Spence et al. containing not only a CDX2$^+$ FOXA2$^+$ endodermal population, but also a significant mesenchymal CDX2$^+$ cell population. In contrast, RA/BMP4 or RA/BMP2 post-Stage 2 (primitive gut tube cell) conditioning did not induce the mesoderm/mesenchyme marker HAND1; only endodermal CDX2$^+$ FOXA2$^+$ population was induced.

In describing the present invention and its various embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

We claim:

1. A method of producing a population of intestinal midgut endoderm cells, comprising:
   culturing human pluripotent stem cells in a first culture media containing GDF-8 and a GSK3β inhibitor compound to definitive endoderm cells;
   culturing the definitive endoderm cells in a second culture media containing ascorbic acid and FGF7 to primitive gut tube cells; and
   culturing the primitive gut tube cells in a third culture media containing retinoic acid and BMP2 or BMP4 to intestinal midgut endoderm cells,
   wherein a population of substantially intestinal midgut endoderm cells is produced.

2. A method of producing a population of intestinal midgut endoderm cells, comprising:
   culturing human pluripotent stem cells in a first culture media containing GDF-8 and a GSK3β inhibitor compound to definitive endoderm cells;
   culturing the definitive endoderm cells in a second culture media containing ascorbic acid and FGF7 to primitive gut tube cells; and
   culturing the primitive gut tube cells in a third culture media containing retinoic acid and BMP2 or BMP4 to intestinal midgut endoderm cells,
   wherein the intestinal midgut endoderm cells form and remain stable as a monolayer.

3. The method of claim 1 or claim 2, wherein the intestinal midgut endoderm cells express CDX2 and FOXA2.

4. The method of claim 1 or claim 2, wherein the intestinal midgut endoderm cells express transcription factors selected from the group consisting of SOX9, PDX1, KLF5 and HOXC5.

5. The method of claim 1 or claim 2, wherein the intestinal midgut endoderm cells do not express transcription factors selected from the group consisting of SOX2, ALB, PTF1A, HOXA13 and LGR5.

6. The method of claim 1, wherein the intestinal midgut endoderm cells form and maintain a monolayer in culture.

7. The method of claim 1 or claim 2, wherein the population of substantially intestinal midgut endoderm cells does not include mesenchymal cells.

8. The method of claim 1 or claim 2, wherein the population of substantially intestinal midgut endoderm cells does not express HAND1.

9. The method of claim 1 or claim 2, wherein the culturing steps are performed in vitro.

* * * * *